(12) United States Patent
Parker et al.

(10) Patent No.: US 8,071,778 B2
(45) Date of Patent: Dec. 6, 2011

(54) SUBSTITUTED HETEROCYCLIC ETHERS AND THEIR USE IN CNS DISORDERS

(75) Inventors: Michael F. Parker, Higganum, CT (US); Joanne J. Bronson, Durham, CT (US); Mark V. Silva, Centereach, NY (US); Kevin W. Gillman, Madison, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 353 days.

(21) Appl. No.: 12/019,994

(22) Filed: Jan. 25, 2008

(65) Prior Publication Data

US 2009/0030040 A1     Jan. 29, 2009

Related U.S. Application Data

(63) Continuation-in-part of application No. 11/782,045, filed on Jul. 24, 2007.

(60) Provisional application No. 60/833,652, filed on Jul. 27, 2006.

(51) Int. Cl.
*C07D 211/22*    (2006.01)
*A61K 31/4545*    (2006.01)

(52) U.S. Cl. ......... 546/194; 544/242; 544/333; 514/318

(58) Field of Classification Search ................. 546/194, 546/208, 236; 544/242, 333; 514/256, 318
See application file for complete search history.

(56) References Cited

U.S. PATENT DOCUMENTS

| | | |
|---|---|---|
| 5,620,989 A | 4/1997 | Harrison et al. |
| 5,760,018 A | 6/1998 | Baker et al. |
| 7,098,203 B2 | 8/2006 | Wu et al. |
| 7,138,423 B2 | 11/2006 | Wu et al. |
| 2006/0019944 A1 | 1/2006 | Wu et al. |
| 2006/0019992 A1 | 1/2006 | Wu et al. |
| 2006/0223830 A1 | 10/2006 | De Nanteuil et al. |
| 2007/0249607 A1 | 10/2007 | Degnan et al. |

FOREIGN PATENT DOCUMENTS

| | | |
|---|---|---|
| EP | 0 337 167 B1 | 8/1994 |
| WO | WO 03/078376 A1 | 9/2003 |
| WO | WO 2004/004722 A1 | 1/2004 |
| WO | WO 2004/022539 A1 | 3/2004 |
| WO | WO2004/083171 A2 | 9/2004 |

OTHER PUBLICATIONS

George A. Patani "Bioisosterism: A Rational Approach in Drug Design" Chemical Reviews 1996, 96, 3147-3176.*
Wermuth, Camille G. "Molecular Variation Based on Isosteric Replacements" in Chapter 13, The Practice of Medicinal Chemistry, Academic: 1996.*
Nakamura, Toshio "Imidazole derivatives as new potent and selective 20-HETE synthase inhibitors." Bioorganic & Medicinal Chemistry Letters 2004, 14, 333-336.*
Li, Bing et. al. "N-(Arylacetyl)-biphenylalanines as Potent VLA-4 Antagonists" Bioorganic & Medicinal Chemistry Letters 2002, 12, 2141-2144.*
Gentsch, C., et al., "Anxiolytic effect of NKP608, a NK-1-receptor antagonist, in the social investigation test in gerbils", *Behavioural Brain Research*, 133 (2002) 363-368.
Kramer, M.S., et al., "Distant Mechanism for Antidepressant Activity by Blockade of Central Substance P Receptors", *Science*, 281 (1998) 1640-1645.
Papp, M., et al., "The NK-1 receptor antagonist NKP608 has an antidepressant-like effect in the chronic mild stress model of depression in rats", *Behavioural Brain Research*, 115 (2000) 19-23.
Rosen, T.J., et al., "Synthesis and structure-activity relationships of CP-122,721, a second-generation NK-1 receptor antagonist", *Bioorganic Med. Chem. Lett.*, 8 (1998) 281-284.
Stevenson, G.I., et al., "4,4-Disubstituted Piperidines: A New Class of $NK_1$ Antagoinists", *J. Med. Chem.*, 38 (1995) 1264-1266.
Stevenson, G.I., et al., "4,4-Disubstituted Piperidine High-Affinity $NK_1$ Antagoinists: Structure-Activity Relationships and in Vivo Activity", *J. Med. Chem.*, 41 (1998) 4623-4635.
Varty, G.B., et al., "The Gerbil Elevated Plus-mase II: Anxiolytic-like Effects of Selective Neurokinin NK1 Receptor Antagonists", *Neuropsychopharmacology*, 27 (2002) 371-379.

\* cited by examiner

*Primary Examiner* — David K O'Dell
(74) *Attorney, Agent, or Firm* — James Epperson

(57) ABSTRACT

The invention encompasses compounds of Formula I, including pharmaceutically acceptable salts, their pharmaceutical compositions, and their use in treating CNS disorders.

10 Claims, No Drawings

SUBSTITUTED HETEROCYCLIC ETHERS AND THEIR USE IN CNS DISORDERS

CROSS REFERENCE TO RELATED APPLICATIONS

This application claims the benefit of U.S. provisional application No. 60/833,652, filed Jul. 27, 2006 and U.S. nonprovisional application Ser. No. 11/782,045, filed Jul. 24, 2007.

BACKGROUND OF THE INVENTION

Tachykinins are a group of naturally occurring peptides found widely distributed throughout mammals, both within the central nervous system and in the peripheral nervous and circulatory systems. The three known mammalian tachykinins are Neurokinin-1 (NK-1, substance P), Neurokinin A, and Neurokinin B. These compounds act as neurotransmitters and immunomodulators and may contribute to the pathophysiology of a wide variety of human diseases.

Receptors for tachykinins have been identified and include neurokinin-1 (NK-1 or Substance P-preferring), NK-2 (Neurokinin A-preferring) and NK-3 (Neurokinin B-preferring). NK-1 receptor antagonists are being developed for the treatment of physiological conditions associated with an excess or imbalance of tachykinins, particularly substance P. Such conditions include affective disorders such as anxiety, depression, obsessive compulsive disorder, bulimia, and panic disorder. See Gentsch et al. *Behav. Brain Res.* 2002, 133, 363; Varty et al. *Neuropsychopharmacology* 2002, 27, 371; Papp et al. *Behav. Brain Res.* 2000, 115, 19; Kramer et al. *Science* 1998, 281, 1640; and Rosen et al. *Bioorg. Med. Chem. Lett.* 1998, 8, 281. Robust antidepressant activity has been reported for two NK-1 antagonists, MK-869 (M. S. Kramer, et al., Science 1998, 281 1640) and CP-122,721 (T. J. Rosen, et al., Bioorganic and Medicinal Chemistry Letters 1998, 8, 28 and CNS Drug News, December, 2000, 24).

Selective serotonin reuptake inhibitors (SSRI's) have proven to be effective in treating depression, but have the disadvantages of delayed onset of antidepressant activity, limited efficacy, and significant side effects. See Novel strategies for pharmacotherapy of depression, K. A. Maubach, N. M. J. Rupniak, M. S. Kramer, and R. G. Hill, Current Opinion in Chemical Biology 1999, 3, 491-499. Selective serotonin reuptake inhibitors (SSRIs) in combination with other agents can be useful for the treatment of depression and other disorders and combination SERT/NK1 compounds should also be useful for these conditions. For example, the combination of SSRIs with dopamine reuptake inhibitors such bupropion and modafanil have shown clinical benefit relative to SSRIs alone, primarily due to superior side effect profiles (Bodkin et al, 1997, J Clin Psychiatry, 58: 137-145; Kennedy et al, 2002, J Clin Psychiatry, 63:181-186). Additionally, the combination of SSRIs with 5-HT1A antagonists such as pindolol have shown improved clinical response relative to SSRIs alone (Artigas F et al, 1994, Arch Gen Psychiatry 51:248-251; Blier P and Bergeron R, 1995, J Clin Psychopharmacol 15:217-222). Finally, combining SSRIs with antipsychotics, such as fluoxetine plus olanzapine, has provided superior profiles in certain depressed populations including psychotic depression and bipolar depression (Corya et al, 2003, J Clin Psychiatry, 64:1349-1356; Rothschild et al, 2004, J Clin Psychopharmacol, 24:365-373).

NK-1 antagonists are believed to modulate 5-HT function via noradrenergic pathways and have been shown to attenuate presynaptic $5\text{-}HT_{1A}$ receptor function. NK-1 antagonists offer an alternative approach for treating depression in patients that respond poorly to the SSRI's and other available drugs and the combination of serotonin reuptake inhibition with NK-1 antagonism may lead to new classes of drugs with improved characteristics.

DESCRIPTION OF THE INVENTION

The invention encompasses compounds of Formula I and related compound and compositions, including pharmaceutically acceptable salts, and their use in treating CNS disorders related to levels of tachykinins or serotonin or both.

One aspect of the invention are compounds of Formula I

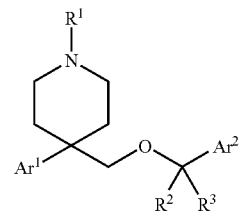

where:
$R^1$ is hydrogen or alkyl;
$R^2$ is hydrogen or alkyl;
$R^3$ is hydrogen or alkyl;
$R^4$ is azetidinyl, pyrrolidinyl, piperidinyl, piperazinyl, morpholinyl, thiomorpholinyl, or pyrrolinyl and is substituted with 0-3 substituents selected from the group consisting of halo, alkyl, haloalkyl, cyano, amino, alkylamino, dialkylamino, pyrrolidinyl, and piperidinyl;
$R^5$ is hydrogen or alkyl;
$Ar^1$ is phenyl or pyridinyl and is substituted with 0-3 substituents selected from the group consisting of halo, alkyl, haloalkyl, and cyano;
$Ar^2$ is pyridinyl or pyrimidinyl and is substituted with 0-3 substituents selected from the group consisting of halo, alkyl, cycloalkyl, (cycloalkyl)alkyl, haloalkyl, alkoxy, haloalkoxy, cyano, amino, alkylamino, dialkylamino, $R^4$, and $Ar^3$; and
$Ar^3$ is phenyl, pyridinyl, furanyl, thienyl, pyrrolyl, isoxazolyl, isothiazolyl, pyrazolyl, oxazolyl, thiazolyl, imidazolyl, oxadiazolyl, thiadiazolyl, triazolyl, or tetrazolyl and is substituted with 0-3 substituents selected from the group consisting of halo, alkyl, haloalkyl, alkoxy, haloalkoxy, cyano, and $CO_2R^5$;
or a pharmaceutically acceptable salt thereof.

Another aspect of the invention is a compound of formula I where:
$R^1$ is hydrogen or alkyl;
$R^2$ is hydrogen or alkyl;
$R^3$ is hydrogen or alkyl;
$Ar^1$ is phenyl substituted with 0-2 substituents selected from the group consisting of halo, alkyl, haloalkyl, and cyano;
$Ar^2$ is pyridinyl or pyrimidinyl and is substituted with 0-3 substituents selected from the group consisting of halo, alkyl, haloalkyl, alkoxy, haloalkoxy, cyano, amino, alkylamino, dialkylamino, pyrrolidinyl, piperidinyl, piperazinyl, (alkyl)piperazinyl, morpholinyl, thiomorpholinyl, and $Ar^3$; and
$Ar^3$ is phenyl or pyridinyl and is substituted with 0-3 substituents selected from the group consisting of halo, alkyl, haloalkyl, alkoxy, haloalkoxy, and cyano;
or a pharmaceutically acceptable salt thereof.

Another aspect of the invention are compounds of Formula I where $R^1$ is hydrogen.

Another aspect of the invention are compounds of Formula I where $R^1$ is methyl.

Another aspect of the invention are compounds of Formula I where $R^2$ and $R^3$ are hydrogen.

Another aspect of the invention are compounds of Formula I where $R^2$ is methyl and $R^3$ is hydrogen.

Another aspect of the invention are compounds of Formula I where $Ar^1$ is phenyl.

Another aspect of the invention is a compound of formula I where $Ar^2$ is pyridinyl or pyrimidinyl and is substituted with 2 substituents selected from the group consisting of halo, alkyl, haloalkyl, alkoxy, haloalkoxy, cyano, amino, alkylamino, dialkylamino, pyrrolidinyl, piperidinyl, piperazinyl, (alkyl)piperazinyl, morpholinyl, thiomorpholinyl, and $Ar^3$.

Another aspect of the invention is a compound of formula I where $Ar^2$ is pyridinyl or pyrimidinyl and is substituted with 2 substituents in a 1,3,5 substitution pattern (meta, meta substitution) selected from the group consisting of halo, alkyl, haloalkyl, alkoxy, haloalkoxy, cyano, amino, alkylamino, dialkylamino, pyrrolidinyl, piperidinyl, ($R^1$)-piperazinyl, morpholinyl, thiomorpholinyl, and $Ar^3$.

Another aspect of the invention are compounds of Formula I where $Ar^2$ is pyridinyl and is substituted with 0-3 substituents selected from the group consisting of halo, alkyl, cycloalkyl, (cycloalkyl)alkyl, haloalkyl, alkoxy, haloalkoxy, cyano, amino, alkylamino, dialkylamino, $R^4$, and $Ar^3$.

Another aspect of the invention are compounds of Formula I where $Ar^2$ is 2-pyridinyl and is substituted with 0-3 substituents selected from the group consisting of halo, alkyl, cycloalkyl, (cycloalkyl)alkyl, haloalkyl, alkoxy, haloalkoxy, cyano, amino, alkylamino, dialkylamino, $R^4$, and $Ar^3$.

Another aspect of the invention are compounds of Formula I where $Ar^2$ is pyrimidinyl and is substituted with 0-3 substituents selected from the group consisting of halo, alkyl, cycloalkyl, (cycloalkyl)alkyl, haloalkyl, alkoxy, haloalkoxy, cyano, amino, alkylamino, dialkylamino, $R^4$, and $Ar^3$.

Another aspect of the invention are compounds of Formula I where $Ar^3$ is phenyl substituted with 1-3 substituents selected from the group consisting of halo, alkyl, haloalkyl, alkoxy, haloalkoxy, cyano, and $CO_2R^5$.

Any scope of a substituent, including $R^1$, $R^2$, $R^3$, $R^4$, $Ar^1$, $Ar^2$, and $Ar^3$, can be used independently with the scope of any other instance of a substituent.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some Formula I compounds contain at least one asymmetric carbon atom, an example of which is shown below. The invention includes all stereoisomeric forms of the compounds, both mixtures and separated isomers. Mixtures of stereoisomers can be separated into individual isomers by methods known in the art.

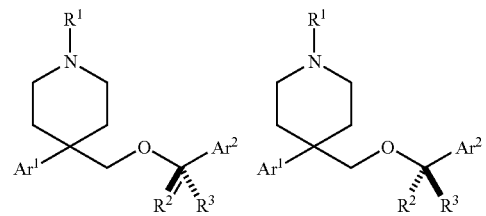

Synthetic Methods

Compounds of Formula I can be made according to methods known in the art and those illustrated in the schemes below and in the specific embodiments section. The compounds can be made by reasonable variations known in the art. The variables describing general structural formulas and features in the synthetic schemes are distinct from and should not be confused with the variables in the claims or the rest of the specification. These variables are meant only to illustrate how to make some of the compounds of this invention. For this section, a benzene ring with an H in the middle can represent a phenyl or heteroaryl moiety, for example pyridinyl or pyrimidinyl.

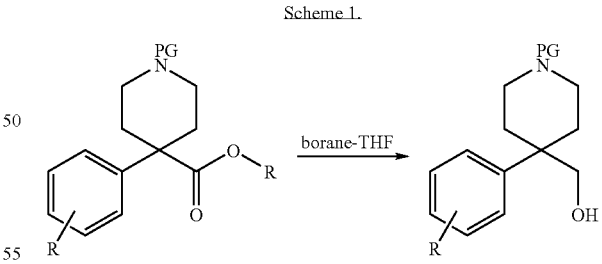

Scheme 1.

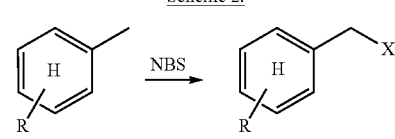

Scheme 2.

Scheme 3.
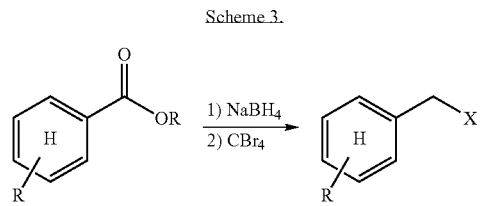
Scheme 4.
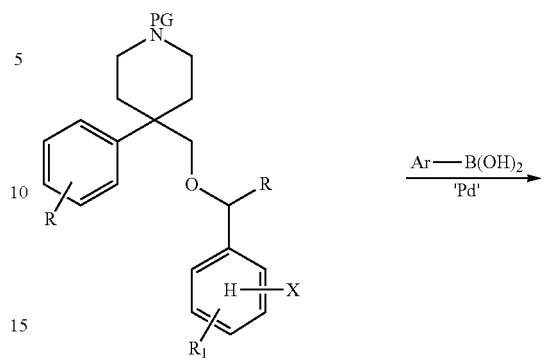
Scheme 5.
Scheme 6.

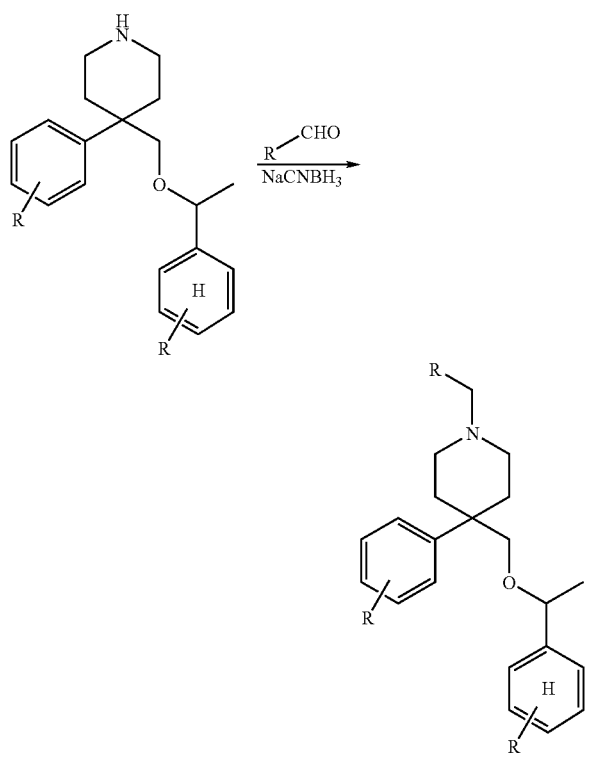

Scheme 7.

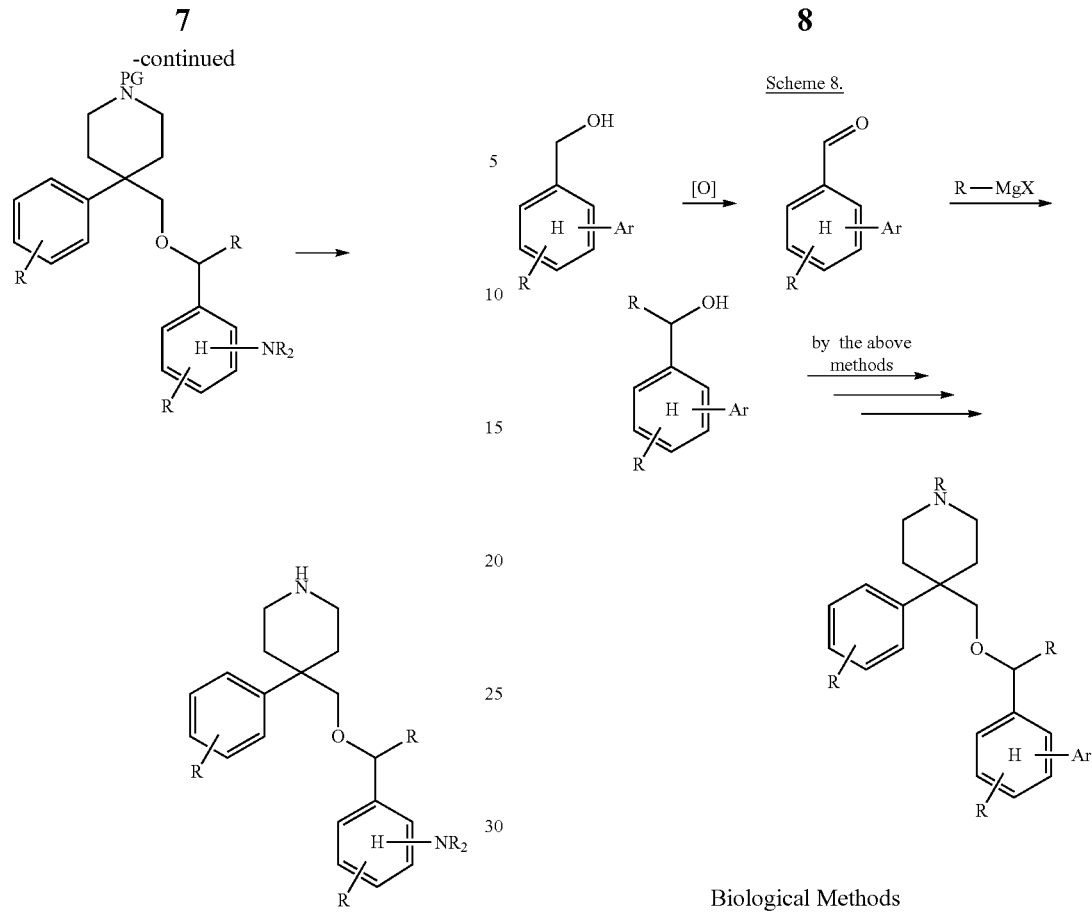

Scheme 8.

Biological Methods

NK-1 Binding assay. Crude membrane suspensions were prepared for the NK1 and SERT radioligand binding assays from U373 cells or recombinant HEK-293 cells expressing hSERT, respectively. Cells were harvested from T-175 flasks as follows. The medium is removed from the flasks and the cells rinsed with HBSS without Ca and without Mg. The cells are then incubated for 5-10 minutes in 10 mM Tris-Cl, pH 7.5, 5 mM EDTA before the cells are lifted with a combination of pipetting and scraping, as needed. To prepare membranes, the cell suspension is collected into centrifuge bottles and homogenized for 30 seconds with a Polytron homogenizer. The suspension is centrifuged for 30 min 32,000×g, 4° C., then the supernatant is decanted and the pellet resuspended and homogenized in 50 mM Tris-Cl, pH 7.5, 1 mM EDTA for 10 seconds. The suspension is then centrifuged again for 30 min 32,000×g, 4° C. The supernatant is decanted and the pellet resuspended in 50 mM Tris-Cl, pH 7.5, 1 mM EDTA and briefly homogenized. A Bradford assay (Bio-rad) is performed and the membrane preparation diluted to 2 mg/ml with 50 mM Tris-Cl, pH 7.5, 1 mM EDTA. Aliquots are prepared, and then frozen and stored at −80° C.

NK1 radioligand binding assay. Compounds are dissolved in 100% DMSO at a concentration 100× the desired highest assay concentration, serially diluted 1:3 in 100% DMSO, and 0.6 ul/well of each solution is dispensed to a Nunc polypropylene, round bottom, 384 well plate. 100% inhibition is defined with 0.6 ul/well of 1 mM L-733,060 (Sigma L-137) dissolved in DMSO. 30 ul/well of a 2× U373 membrane preparation (267 ug/ml in 100 mM Tris-Cl, pH 7.5, 6 mM $MgCl_2$, 0.2% (v/v) Sigma mammalian protease inhibitor cocktail (Sigma P-8340), and 4 ug/ml chymostatin, Sigma C-7268) and 30 ul/well of a 2× radioligand solution (400 pM [$^{125}$I]Substance P (Perkin Elmer NEX-190) in 1% (w/v) BSA (Sigma A-2153), 0.1 mg/ml bacitracin, Sigma B-0125) are added to the well and the reaction incubated for 1 hour at room temperature. The contents of the assay plate are then transferred to a Millipore Multiscreen$_{HTS}$ GF/B filter plate which has been pretreated with 0.5% PEI for at least one hour. The plate is vacuum filtered and washed with 7 washes of 100 ul/well of 20 mM Tris-Cl, pH 7.5, 0.5% (w/v) BSA chilled to 4° C. The filtration and washing is completed in less than 90 s. The plates are air-dried overnight, 12 ul/well of MicroScint scintillation fluid added, and the plates counted in a Trilux.

SERT radioligand binding assay. Compounds are dissolved in 100% DMSO at a concentration 100× the desired highest assay concentration, serially diluted 1:3 in 100% DMSO, and 0.4 ul/well of each solution is dispensed to a Nunc polypropylene, round bottom, 384 well plate. 100% inhibition is defined with 0.4 ul/well of 1 mM fluoxetine (Sigma F-132) dissolved in DMSO. 20 ul/well of a 2×HEK-hSERT membrane preparation (15 ug/ml in 50 mM Tris-Cl, pH 7.5, 120 mM NaCl, 5 mM KCl) and 20 ul/well of a 2× radioligand solution (520 pM [$^{125}$I]RTI-55 (Perkin-Elmer NEX-272) in 50 mM Tris-Cl, pH 7.5, 120 mM NaCl, 5 mM KCl) are added to each well and the reaction incubated for 1 hour at room temperature. The contents of the assay plate are then transferred to a Millipore Multiscreen$_{HTS}$ GF/B filter plate which has been pretreated with 0.5% PEI for at least one hour. The plate is vacuum filtered and washed with 7 washes of 100 ul/well of 50 mM Tris-Cl, pH 7.5, 120 mM NaCl, 5 mM KCl chilled to 4° C. The filtration and washing is completed in less than 90 s. The plates are air-dried overnight, 12 ul/well of MicroScint scintillation fluid added, and the plates counted in a Trilux.

Data analysis. The raw data are normalized to percent inhibition using control wells defining 0% (DMSO only) and 100% (selective inhibitor) inhibition which are run on each plate. Each plate is run in triplicate, and the concentration response curve thus generated is fit using the four-parameter dose response equation, Y=Bottom+(Top-Bottom)/(1+10^((Log IC$_{50}$−X)*HillSlope)) in order to determine the IC$_{50}$ value for each compound. The radioligand concentration chosen for each assay corresponds to the K$_d$ concentration determined through saturation binding analysis for each assay. NK-1 and serotonin transporter binding results are shown in Table 1.

TABLE 1

| Example | Structure | NK-1 IC$_{50}$ (nM) | SERT IC$_{50}$ (nM) |
|---|---|---|---|
| 1 | 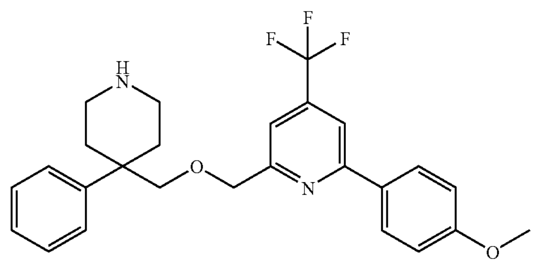 | A | A |
| 2 | 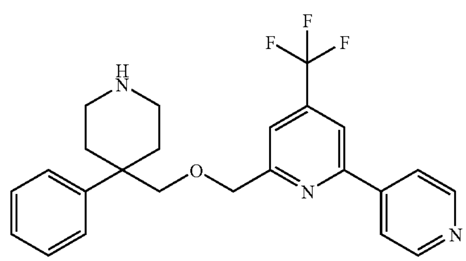 | A | A |
| 3 | 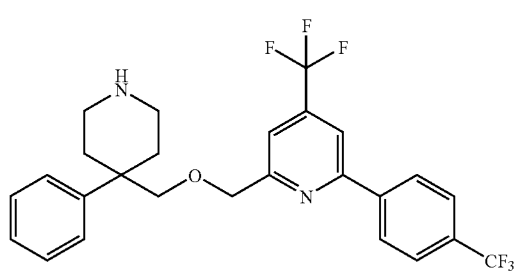 | C | B |

TABLE 1-continued

| Example | Structure | NK-1 IC$_{50}$ (nM) | SERT IC$_{50}$ (nM) |
|---|---|---|---|
| 4 | 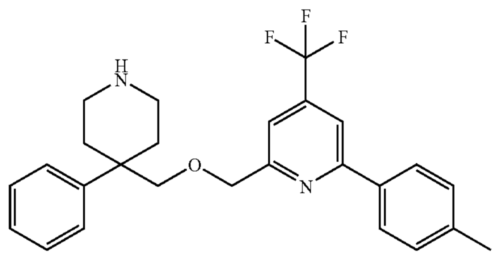 | A | A |
| 5 | 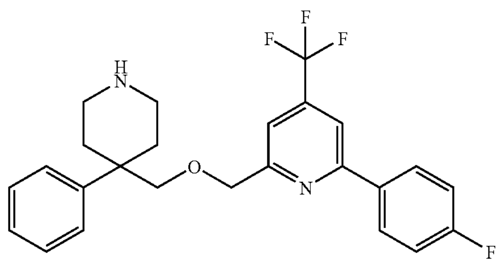 | A | A |
| 6 | 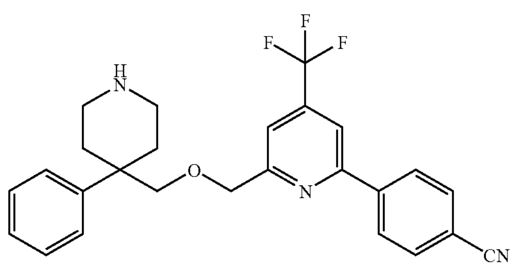 | A | A |
| 7 | 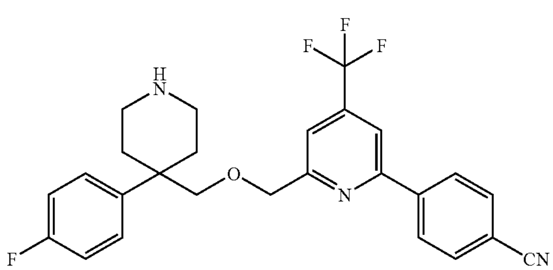 | A | A |
| 8 | 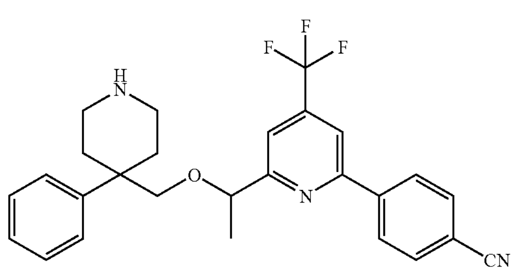 | A | A |
| 9 | 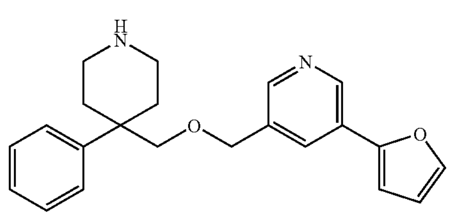 | C | A |

TABLE 1-continued
| Example | Structure | NK-1 IC$_{50}$ (nM) | SERT IC$_{50}$ (nM) |
|---|---|---|---|
| 10 | 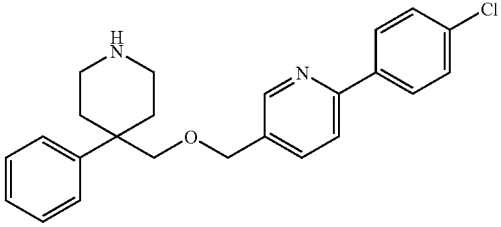 | C | A |
| 11 | 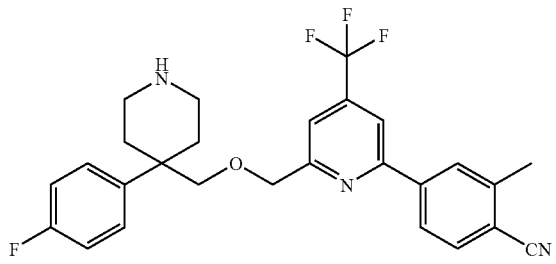 | A | A |
| 12 | 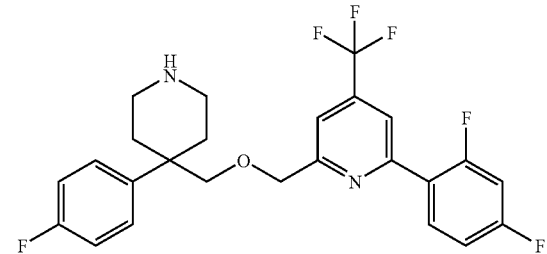 | A | A |
| 13 | 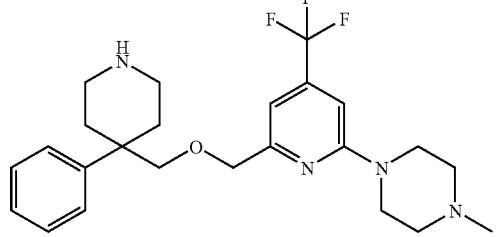 | C | A |
| 14 | 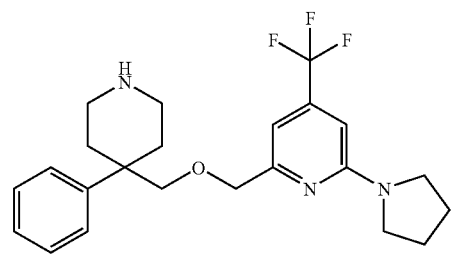 | A | A |
| 15 | 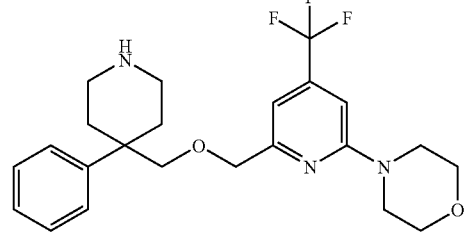 | A | B |

TABLE 1-continued

| Example | Structure | NK-1 IC$_{50}$ (nM) | SERT IC$_{50}$ (nM) |
| --- | --- | --- | --- |
| 16 | 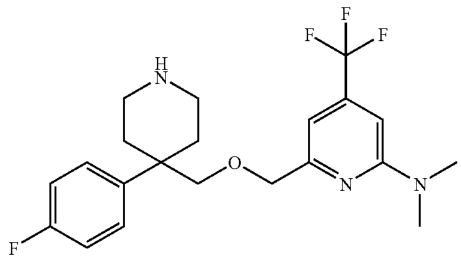 | A | A |
| 17 | 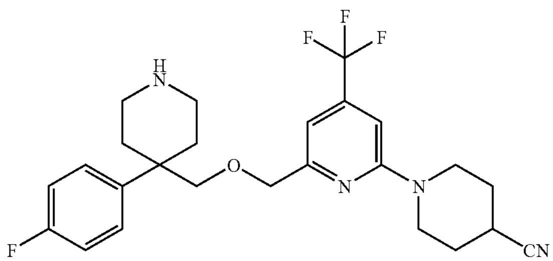 | A | A |
| 18 | 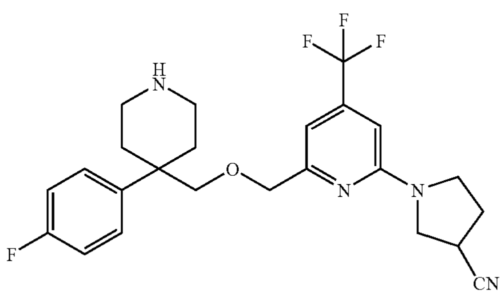 | A | A |
| 19 | 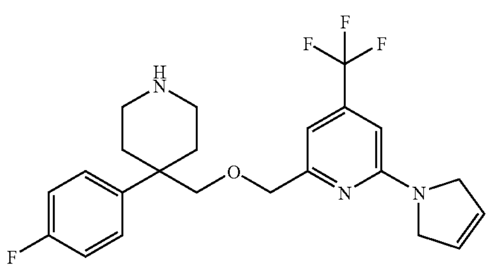 | A | A |
| 20 | 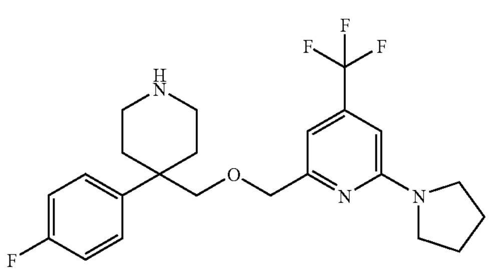 | A | A |

TABLE 1-continued
| Example | Structure | NK-1 IC$_{50}$ (nM) | SERT IC$_{50}$ (nM) |
|---|---|---|---|
| 21 | 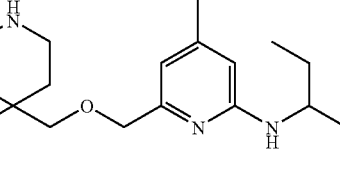 | A | A |
| 22 | 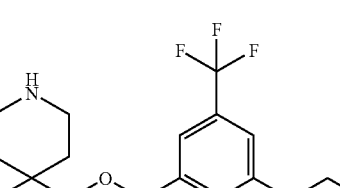 | A | A |
| 23 | 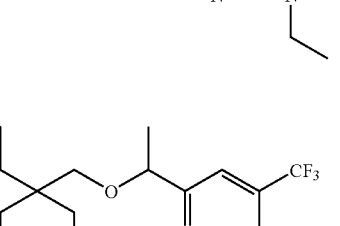 | A | A |
| 24 | 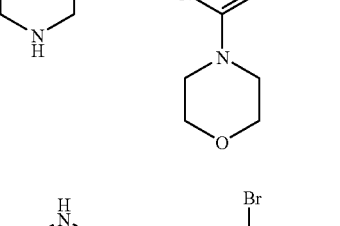 | C | A |
| 25 | 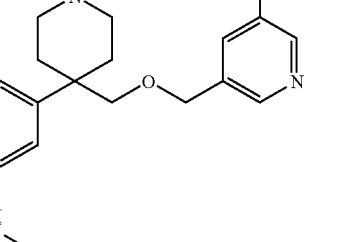 | C | A |
| 26 | 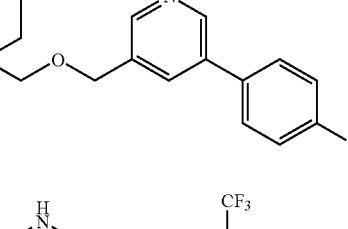 | A | A |

TABLE 1-continued

| Example | Structure | NK-1 IC$_{50}$ (nM) | SERT IC$_{50}$ (nM) |
|---|---|---|---|
| 27 | 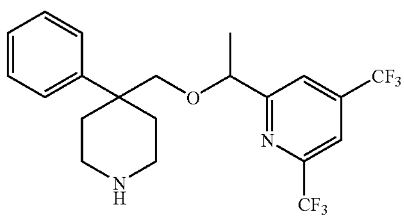 | A | A |
| 28 | 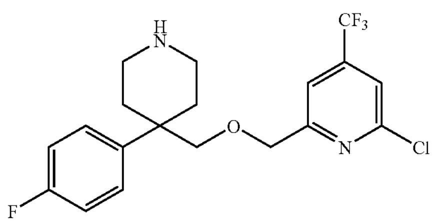 | A | A |
| 29 | 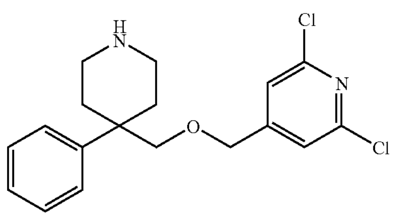 | A | A |
| 30 | 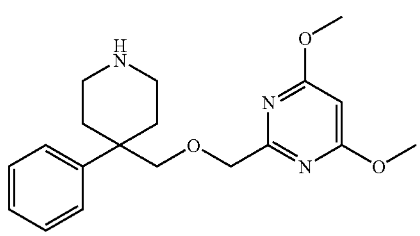 | C | B |
| 31 | 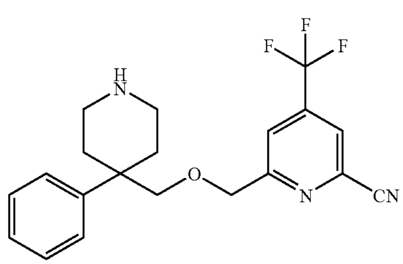 | C | A |
| 32 | 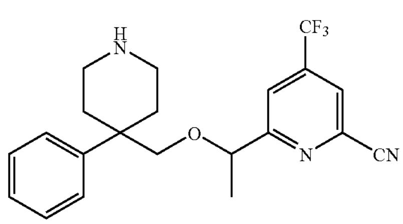 | A | A |

TABLE 1-continued

| Example | Structure | NK-1 IC$_{50}$ (nM) | SERT IC$_{50}$ (nM) |
| --- | --- | --- | --- |
| 33 | 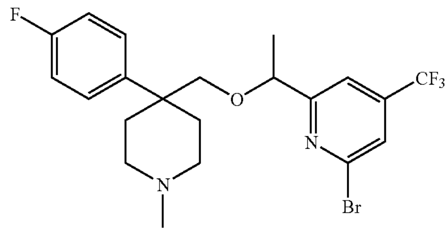 | A | A |
| 34 | 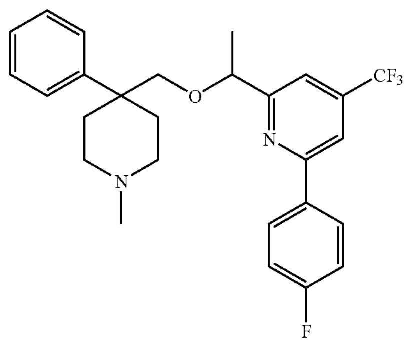 | A | A |
| 35 | 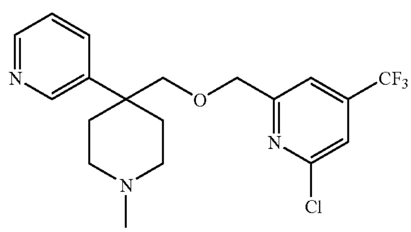 | C | A |
| 36 | 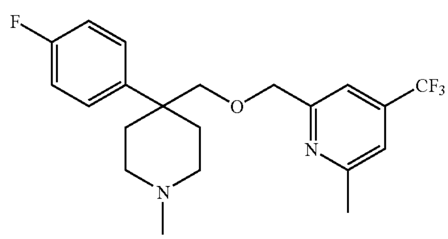 | A | A |
| 37 | 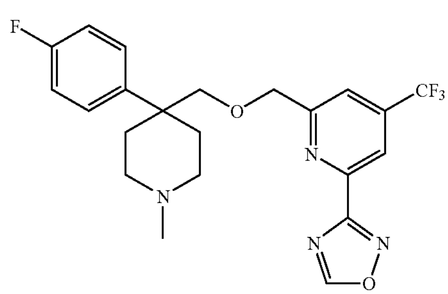 | B | A |

TABLE 1-continued

| Example | Structure | NK-1 IC$_{50}$ (nM) | SERT IC$_{50}$ (nM) |
| --- | --- | --- | --- |
| 38 | 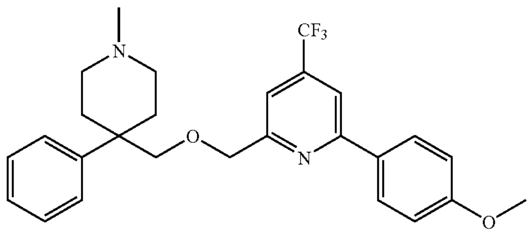 | A | A |
| 39 | 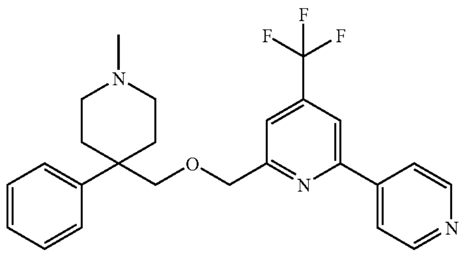 | A | A |
| 40 | 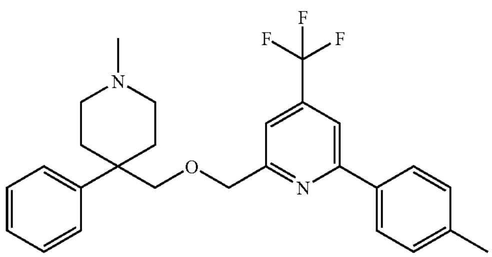 | A | A |
| 41 | 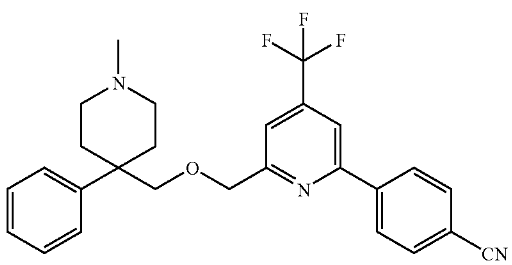 | A | A |
| 42 | 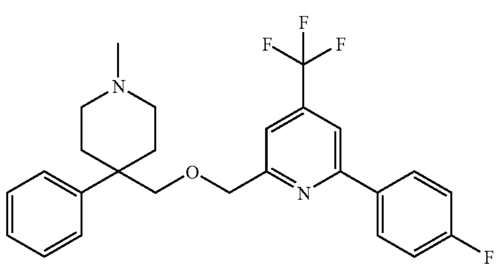 | A | A |
| 43 | 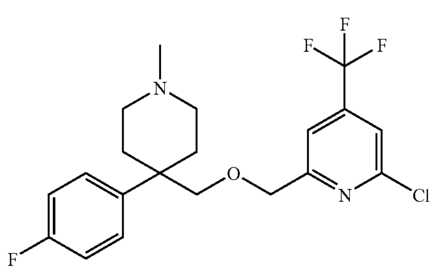 | A | A |

TABLE 1-continued

| Example | Structure | NK-1 IC$_{50}$ (nM) | SERT IC$_{50}$ (nM) |
|---|---|---|---|
| 44 | 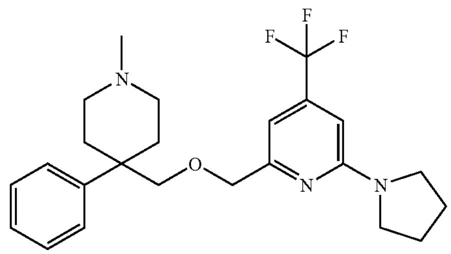 | A | A |
| 45 | 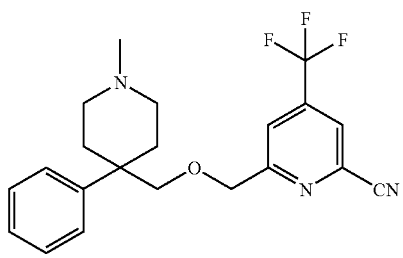 | C | A |
| 46 | 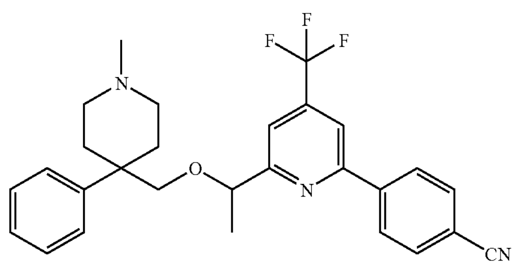 | A | A |
| 47 | 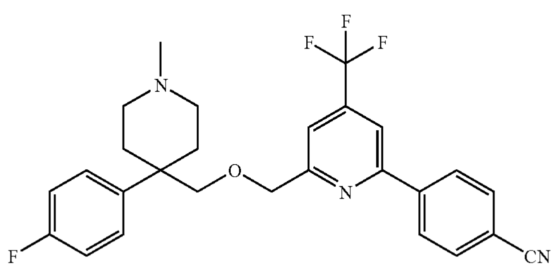 | A | A |
| 48 | 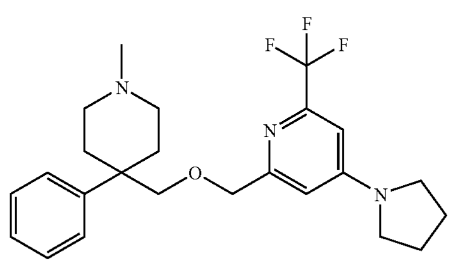 | A | A |
| 49 | 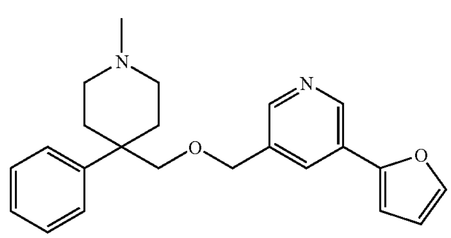 | C | A |

TABLE 1-continued

| Example | Structure | NK-1 IC$_{50}$ (nM) | SERT IC$_{50}$ (nM) |
|---|---|---|---|
| 50 | 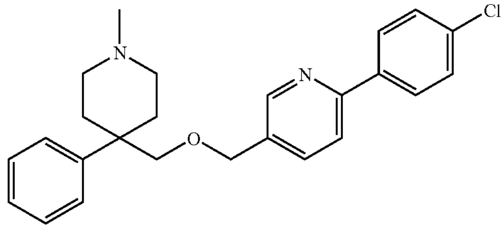 | C | A |
| 51 | 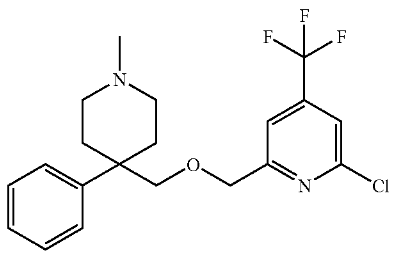 | A | A |
| 52 | 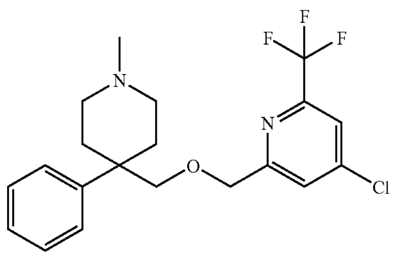 | A | A |
| 53 | 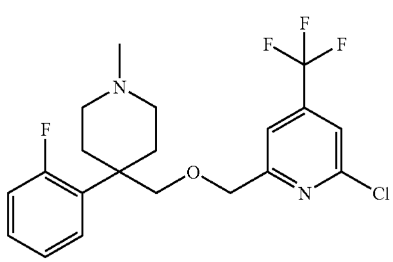 | A | A |
| 54 | 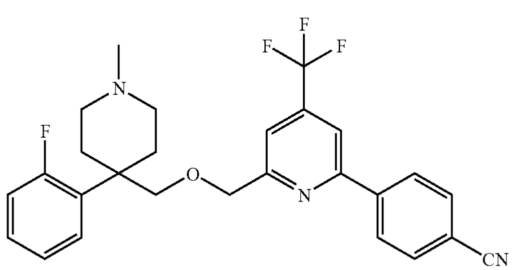 | A | B |
| 55 | 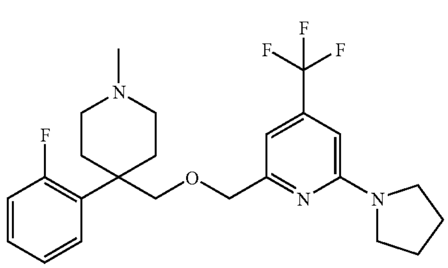 | A | A |

TABLE 1-continued

| Example | Structure | NK-1 IC$_{50}$ (nM) | SERT IC$_{50}$ (nM) |
| --- | --- | --- | --- |
| 56 | 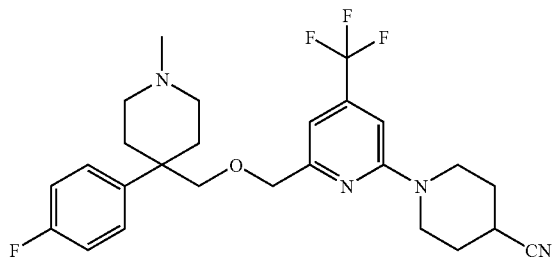 | A | A |
| 57 | 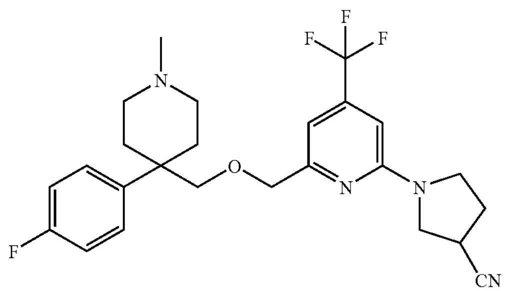 | A | A |
| 58 | 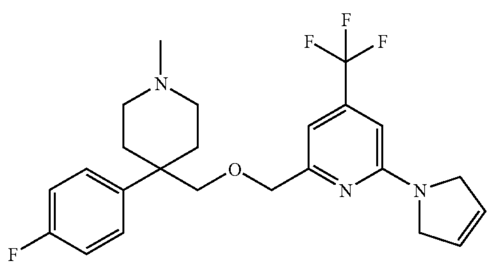 | A | A |
| 59 | 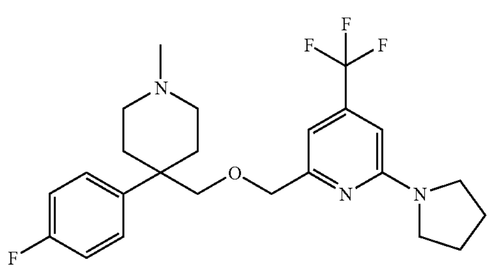 | A | A |
| 60 | 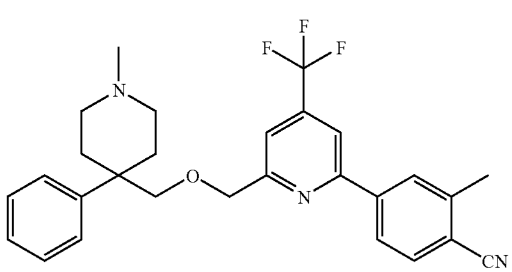 | A | A |

TABLE 1-continued

| Example | Structure | NK-1 IC$_{50}$ (nM) | SERT IC$_{50}$ (nM) |
|---------|-----------|---------------------|---------------------|
| 61 | 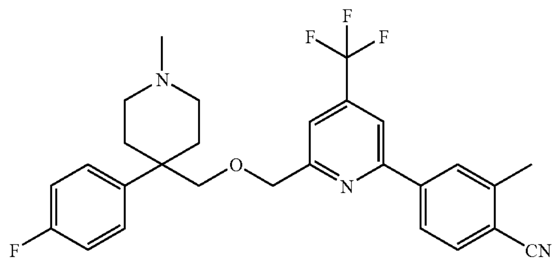 | A | A |
| 62 | 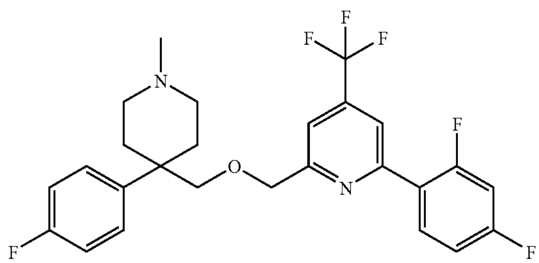 | A | A |
| 63 | 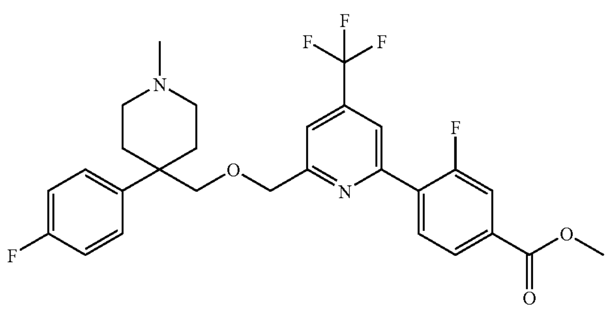 | A | A |
| 64 | 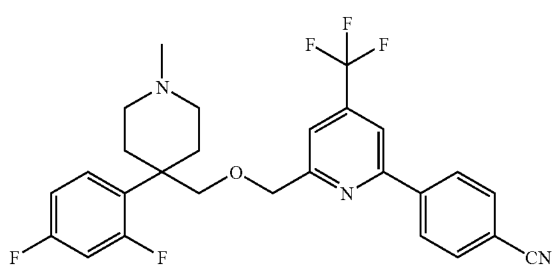 | A | B |
| 65 | 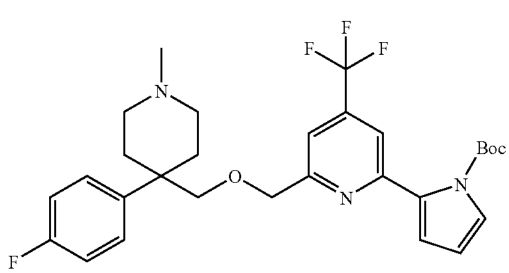 | A | B |

TABLE 1-continued

| Example | Structure | NK-1 IC$_{50}$ (nM) | SERT IC$_{50}$ (nM) |
|---------|-----------|---------------------|---------------------|
| 66 | 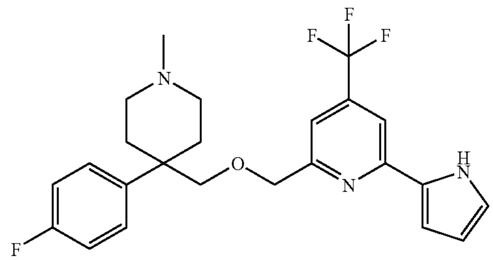 | A | A |
| 67 | 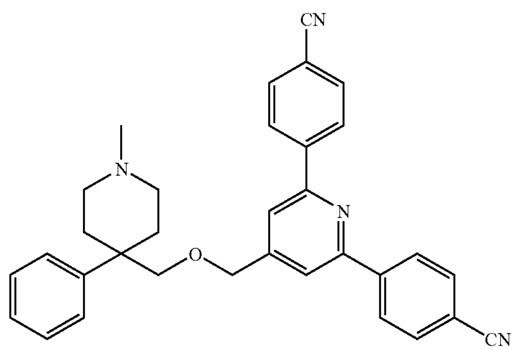 | C | B |
| 68 | 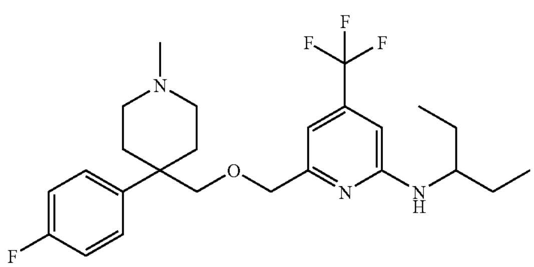 | A | A |
| 69 | 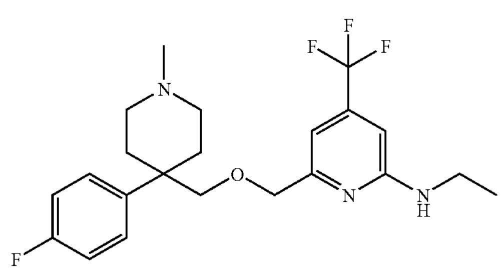 | C | A |
| 70 | 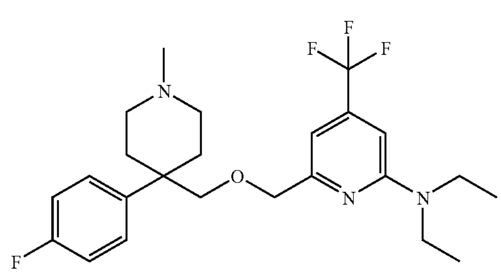 | A | A |

TABLE 1-continued

| Example | Structure | NK-1 IC$_{50}$ (nM) | SERT IC$_{50}$ (nM) |
|---|---|---|---|
| 71 | 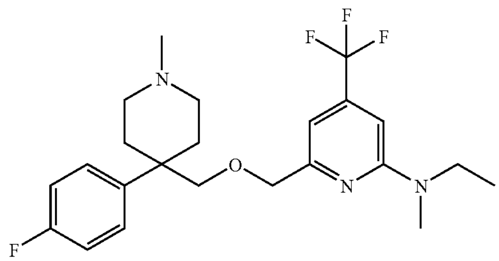 | A | A |
| 72 | 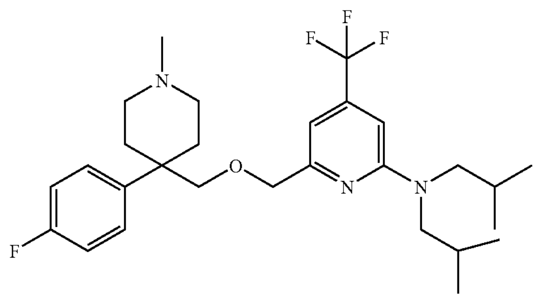 | B | B |
| 73 | 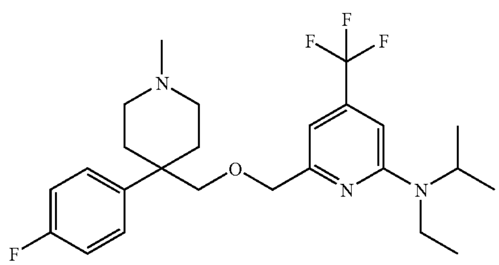 | A | A |
| 74 | 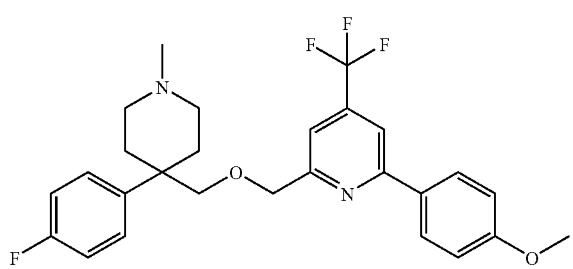 | A | A |
| 75 | 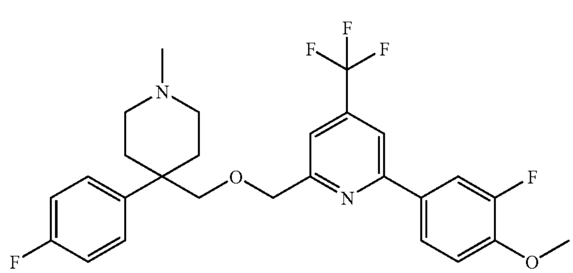 | A | A |

TABLE 1-continued

| Example | Structure | NK-1 IC$_{50}$ (nM) | SERT IC$_{50}$ (nM) |
|---|---|---|---|
| 76 | 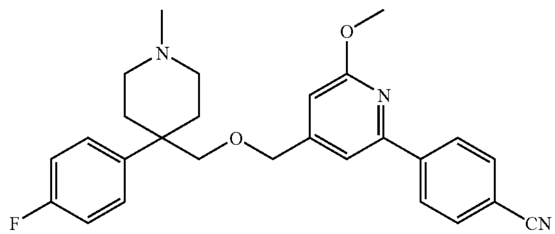 | A | A |
| 77 | 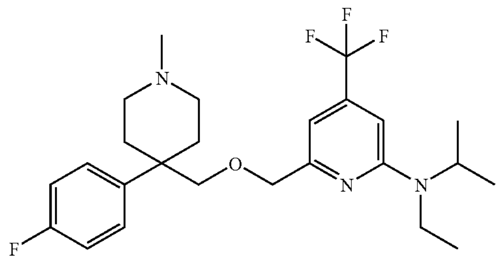 | A | A |
| 78 | 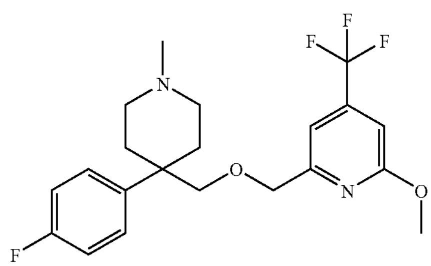 | A | A |
| 79 | 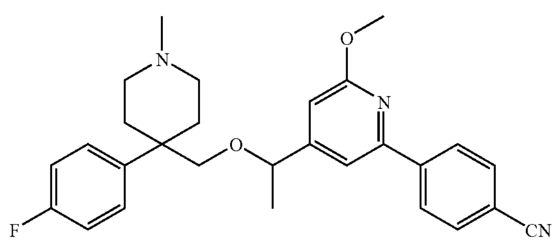 | A | A |
| 80 | 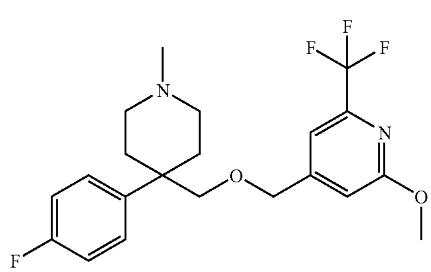 | A | A |

TABLE 1-continued

| Example | Structure | NK-1 IC$_{50}$ (nM) | SERT IC$_{50}$ (nM) |
|---|---|---|---|
| 81 | 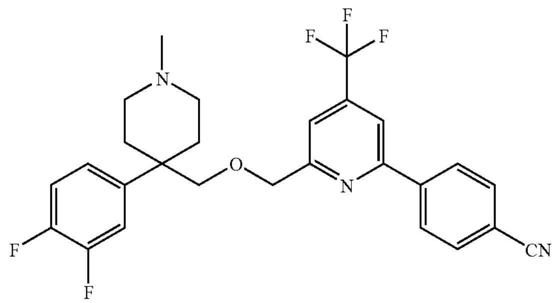 | A | A |
| 82 | 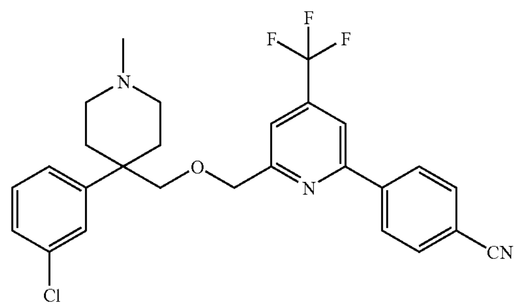 | A | A |
| 83 | 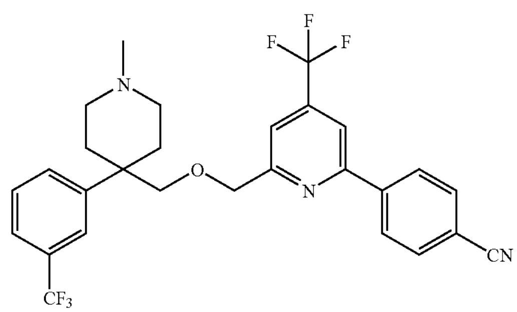 | A | B |
| 84 | 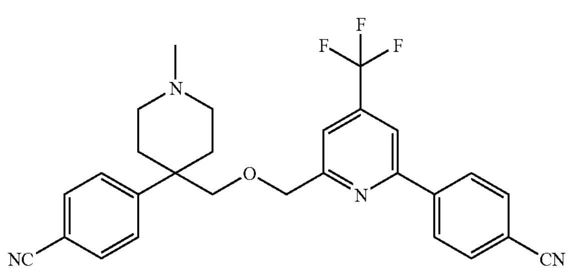 | A | A |
| 85 | 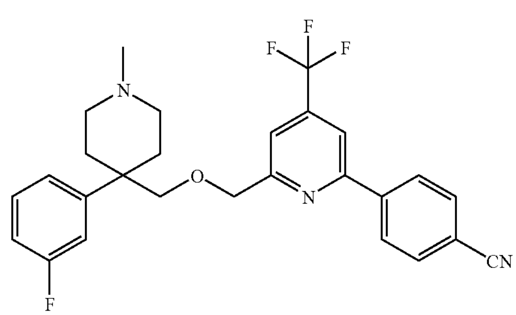 | A | A |

TABLE 1-continued

| Example | Structure | NK-1 IC$_{50}$ (nM) | SERT IC$_{50}$ (nM) |
| --- | --- | --- | --- |
| 86 | 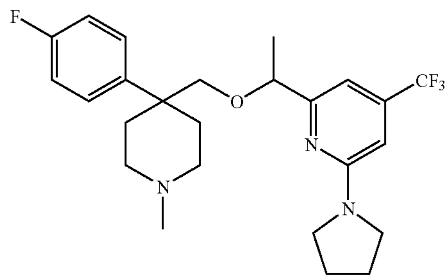 | A | A |
| 87 | 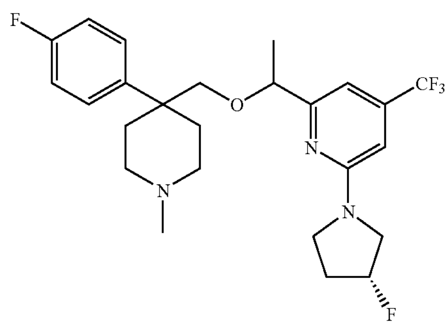 | A | A |
| 88 | 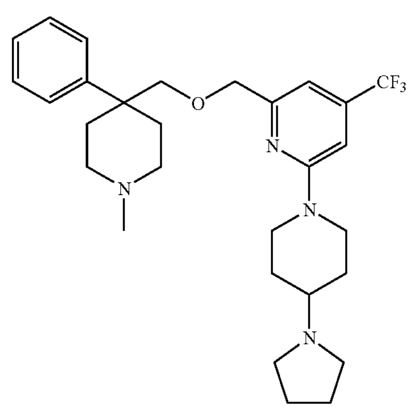 | C | A |
| 89 | 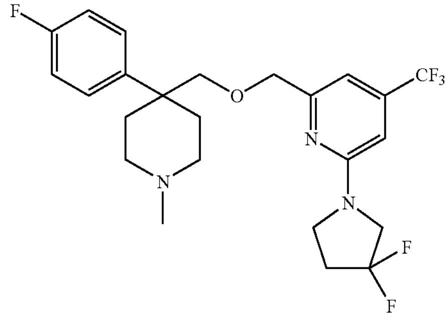 | A | A |

TABLE 1-continued
| Example | Structure | NK-1 IC$_{50}$ (nM) | SERT IC$_{50}$ (nM) |
|---|---|---|---|
| 90 | 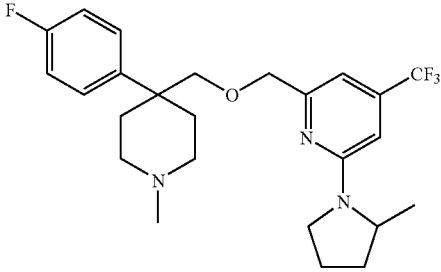 | A | A |
| 91 | 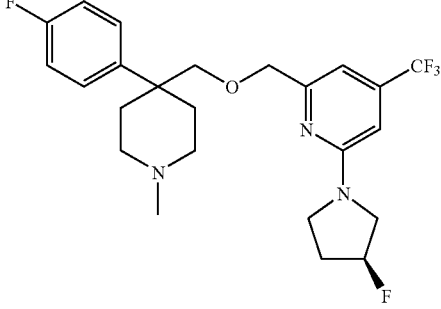 | A | A |
| 92 | 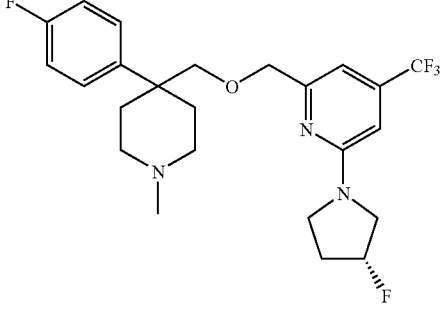 | A | A |
| 93 | 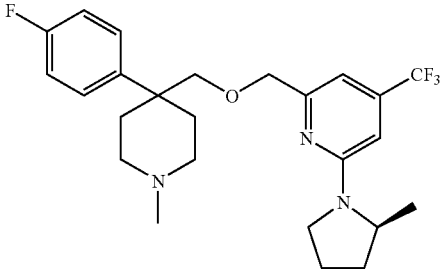 | A | A |
| 94 | 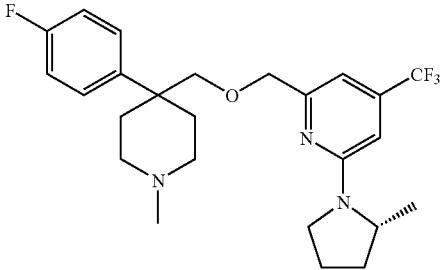 | A | A |

TABLE 1-continued

| Example | Structure | NK-1 IC$_{50}$ (nM) | SERT IC$_{50}$ (nM) |
|---|---|---|---|
| 95 | 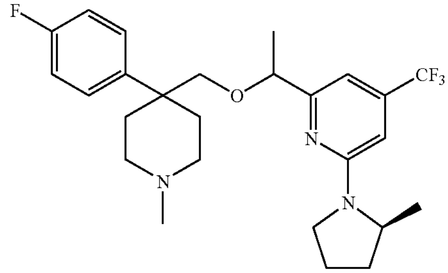 | A | A |
| 96 | 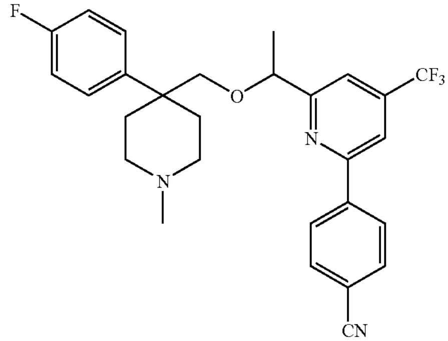 | A | A |
| 97 | 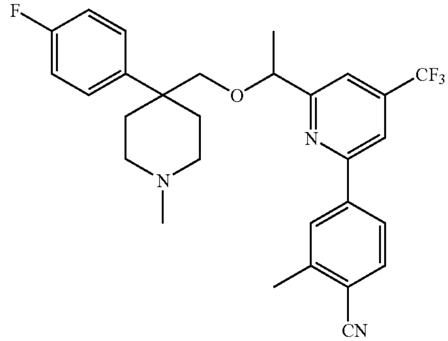 | A | B |
| 98 | 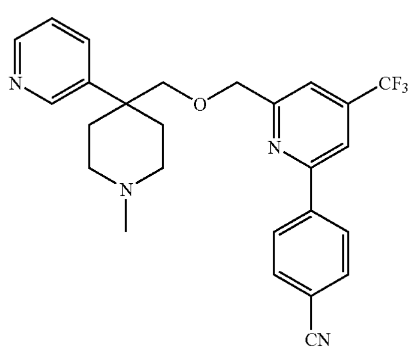 | A | A |

TABLE 1-continued
| Example | Structure | NK-1 IC$_{50}$ (nM) | SERT IC$_{50}$ (nM) |
|---|---|---|---|
| 99 | 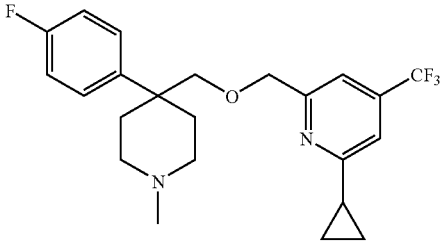 | A | A |
| 100 | 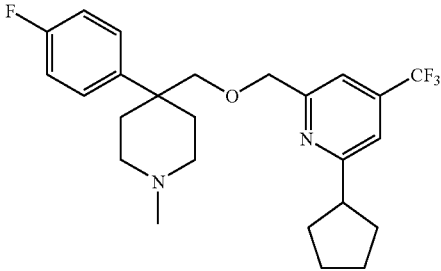 | A | A |
| 101 | 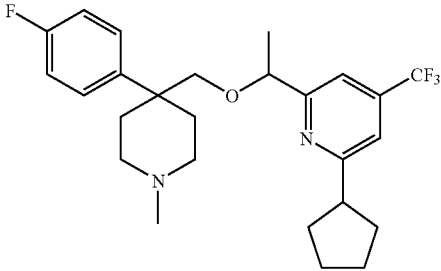 | A | A |
| 102 | 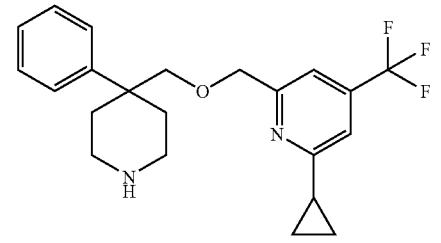 | A | A |
| 103 | 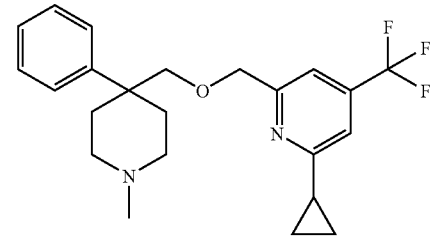 | A | A |
Values:
A = 0.01-100 nM;
B = 100-300 nM;
C >300 nM.

Pharmaceutical Composition and Methods of Use

The compounds of Formula I demonstrate inhibition of neurokinin-1 or serotonin reuptake or both. Inhibition of these receptors correlates with efficacy for affective disorders such as anxiety, depression, obsessive compulsive disorder, bulimia, and panic disorder. As such, the compounds of Formula I can be useful for the treatment of these disorders and other aspects of the invention are compositions and methods of using the compounds to treat these conditions and other conditions associated with aberrant levels of tachykinins or serotonin or both.

The compounds of this invention are generally given as pharmaceutical compositions comprised of a therapeutically effective amount of a compound of Formula I, or a pharmaceutically acceptable salt, and a pharmaceutically acceptable carrier and may contain conventional exipients. A therapeutically effective amount is the amount needed to provide a meaningful patient benefit as determined by practitioners in that art. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques and conventional excipients (such as binding and wetting agents) and vehicles (such as water and alcohols).

Solid compositions are normally formulated in dosage units providing from about 1 to about 1000 mg of the active ingredient per dose. Some examples of solid dosage units are 1 mg, 10 mg, 100 mg, 250 mg, 500 mg, and 1000 mg. Liquid compositions are generally in a unit dosage range of 1-100 mg/mL. Some examples of liquid dosage units are 1 mg/mL, 10 mg/mL, 25 mg/mL, 50 mg/mL, and 100 mg/mL. Generally, the dosage unit will be in a unit range similar to agents of that class used clinically, for example fluoxetine.

The invention encompasses all conventional modes of administration; oral and parenteral methods are preferred. Generally, the dosing regimen will be similar to agents of that class used clinically, for example fluoxetine. Typically, the daily dose will be 0.01-100 mg/kg body weight daily. Generally, more compound is required orally and less parenterally. The specific dosing regime, however, should be determined by a physician using sound medical judgement.

Tachykinin and serotonin modulators are associated with depression. Accordingly, another aspect of the invention are methods for treating depressive disorders including Major Depressive Disorders (MDD), bipolar depression, unipolar depression, single or recurrent major depressive episodes, recurrent brief depression, catatonic features, melancholic features including feeding disorders, such as anorexia, weight loss, atypical features, anxious depression, or postpartum onset. Other central nervous system disorders encompassed within the term MDD include neurotic depression, post-traumatic stress disorders (PTSD) and social phobia, with early or late onset dementia of the Alzheimer's type, with depressed mood, vascular dementia with depressed mood, mood disorders and tolerance induced by drugs such as alcohol, amphetamines, cocaine, inhalants, opioids, sedatives, anxiolytics and other substances, schizoaffective disorder of the depressed type, and adjustment disorder with depressed mood.

Tachykinin and serotonin modulators are also associated with the treatment or prevention of schizophrenic disorders. Accordingly, another aspect of the invention are methods for treating schizophrenic disorders including paranoid schizophrenia, disorganized schizophrenia, catatonic schizophrenia, undifferentiated schizophrenia, residual schizophrenia.

Tachykinin and serotonin modulators are also associated with the treatment or prevention of anxiety. Accordingly, another aspect of the invention are methods for treating anxiety disorders including panic disorders, agoraphobia, phobias, obsessive-compulsive disorder, stress disorders including post-traumatic stress disorders, generalized anxiety disorders, acute stress disorders and mixed anxiety-depression disorders.

Tachykinin and serotonin modulators are also associated with the treatment or prevention of cognitive disorders. Accordingly, another aspect of the invention are methods for treating cognitive disorders including dementia, and amnesia disorders. Tachykinin and serotonin modulators are also associated with the treatment or prevention of memory and cognition in healthy humans.

Tachykinin and serotonin modulators are also associated with use as analgesics. Accordingly, another aspect of the invention are methods for treating pain, including the treatment of traumatic pain such as postoperative pain, chronic pain such as arthritic pain such as occurring in osteo-, rheumatoid or psoriatic arthritis, neuropathic pain such as postherpetic neuralgia, trigeminal neuralgia, segmental or intercostal neuralgia, fibromyalgia, peripheral neuropathy, diabetic neuropathy, chemotherapy-induced neuropathy, AIDS-related neuropathy, various forms of headache such as migraine, acute or chronic tension headache, cluster headaches, maxillary sinus pain, cancer pain, pain of bodily origin, gastrointestinal pain, sport's injury pain, dysmennorrhoea, menstrual pain, meningitis, musculoskeletal pain, low back pain e.g. spinal stenosis, prolapsed disc, sciatica, angina, ankylosing spondyolitis, gout, burns, scar pain, itch and thalamic pain such as post stroke thalamic pain.

Tachykinin and serotonin modulators are also associated with the treatment or prevention of sleep disorders. Accordingly, another aspect of the invention are methods for treating sleep disorders including insomnia, sleep apnea, narcolepsy, and circadian rhymic disorders.

Tachykinin and serotonin modulators are also associated with the treatment or prevention of inflammation. Accordingly, another aspect of the invention are methods for treating inflammation, including the treatment of inflammation in asthma, influenza and chronic bronchitis, in the treatment of inflammatory diseases of the gastrointestinal tract such as Crohn's disease, ulcerative colitis, inflammatory bowel disease and non-steroidal anti-inflammatory drug induced damage, inflammatory diseases of the skin such as herpes and eczema, inflammatory diseases of the bladder such as cystitis and urge incontinence, and eye and dental inflammation.

Tachykinin and serotonin modulators are also associated with the treatment or prevention of allergic disorders. Accordingly, another aspect of the invention are methods for treating allergic disorders, in particular allergic disorders of the skin such as urticaria, and allergic disorders of the airways such as rhinitis.

Tachykinin and serotonin modulators are also associated with the treatment or prevention of emesis, nausea, retching and vomiting. Accordingly, another aspect of the invention are methods for treating these disorders.

Tachykinin and serotonin modulators are also associated with the treatment or prevention of premenstrual dysphoric disorder (PMDD), in chronic fatigue syndrome and multiple sclerosis. Accordingly, another aspect of the invention are methods for treating these disorders.

DESCRIPTION OF SPECIFIC EMBODIMENTS

The following experimental procedures describe the synthesis of some Formula I compounds. Standard chemistry conventions are used in the text unless otherwise noted. The experimental encompass reasonable variations known in the art.

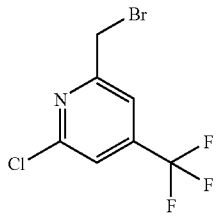

Intermediate 1

2-(bromomethyl)-6-chloro-4-(trifluoromethyl)pyridine. (2-chloro-6-methyl-4-(trifluoromethyl)pyridine (10.0 g, 51 mmol), N-bromosuccinimide (10.9 g, 61 mmol), and 2,2'-azobis(2-methylpropionitrile) (164 mg, 1 mmol) were combined in carbon tetrachloride (200 mL) and heated to reflux. After 16 h, the reaction mixture was cooled to 0° C. and filtered. The filtrate was concentrated and purified by column chromatography on silica gel (100% hexanes) to produce 9.1 g (70%) as a light yellow oil. $^1$H-NMR (CDCl$_3$, 400 MHz) δ 7.59 (s, 1H), 7.47 (s, 1H), 4.52 (s, 2H).

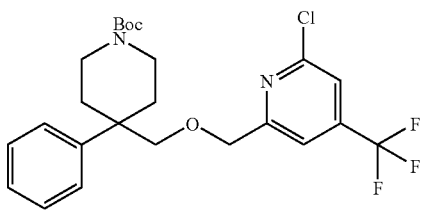

Intermediate 2 tert-butyl 4-(((6-chloro-4-(trifluoromethyl)pyridine-2-yl)methoxy)methyl)-4-phenylpiperidine-1-carboxylate. 2-(bromomethyl)-6-chloro-4-(trifluoromethyl)pyridine (1.1 g, 4.1 mmol) and tert-butyl 4-(hydroxymethyl)-4-phenylpiperidine-1-carboxylate (1.0 g, 3.4 mmol) were combined in tetrahydrofuran (20 mL) and cooled to 0° C. The reaction was treated with potassium tert-butoxide (763 mg, 6.8 mmol) portion wise. The reaction was stirred at 0° C. for 1 hr. The reaction mixture was diluted with water and extracted with ethyl acetate (2×). The organic layers were pooled together, washed with brine (2×), dried over magnesium sulfate, and concentrated. Column chromatography on silica gel (10% ethyl acetate/hexanes) gave 837 mg (52%). $^1$H-NMR (CDCl$_3$, 400 MHz) δ 7.31-7.38 (m, 6H), 7.18 (s, 1H), 4.48 (s, 2H), 3.74-3.79 (m, 2H), 3.50 (s, 2H), 2.99-3.06 (m, 2H), 2.21-2.25 (m, 2H), 1.83-1.86 (m, 2H), 1.42 (s, 9H). Mass spec.: 485.11 (MH)$^+$.

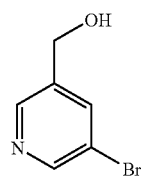

Intermediate 3

(5-bromopyridin-3-yl)methanol. To a cold (0° C.) solution of ethyl-5-bromonicotinate (1.0 g, 4.3 mmoL) in MeOH (15 mL) was added sodium borohydride (650 mg, 17 mmol) portion wise. After 30 min. the reaction was quenched by the addition of water (10 mL). The reaction was then extracted with methylene chloride (3×). The extracts were combined, dried (MgSO$_4$) the filtrate was concentrated and purified by column chromatography on silica gel (0 to 80% ethyl acetate/hexanes) to produce 475 mg (60%) as a clear oil. $^1$H-NMR (CDCl$_3$, 400 MHz) δ 8.57 (s, 1H), 8.49 (s, 1H), 7.91 (s, 1H), 4.73 (s, 2H), 2.51 (s, br, 1H). Mass spec.: 188.12 (MH)$^+$.

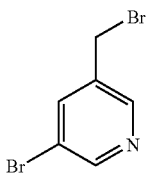

Intermediate 4

3-bromo-5(bromomethyl)pyridine. (5-bromopyridin-3-yl)methanol (475 mg, 2.5 mmol) and triphenylphosphine (1.3 g, 5 mmol) were combined in methylene chloride (20 mL) and cooled to 0° C. carbon tetrabromide (927 mg, 2.8 mmol) was introduced in portions and the reaction was maintained at 0° C. for 1 h. The reaction was concentrated and purified by column chromatography on silica gel (0 to 50% ethyl acetate/hexanes) to produce 254 mg (41%) as a white solid. $^1$H-NMR (D$^6$DMSO, 400 MHz) δ 8.65 (s, br, 2H), 8.18 (s, 1H), 4.73 (s, 2H). Mass spec.: 249.89 (MH)$^+$.

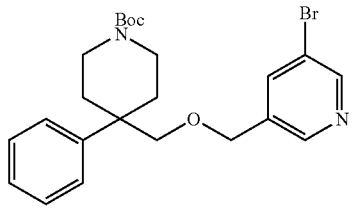

Intermediate 5 tert-butyl 4-(((5-bromopryidin-3-yl)methoxy)methyl)-4-phenylpiperidine-1-carboxylate. 3-bromo-5-(bromomethyl)pyridine (248 mg, 1 mmol) and tert-butyl 4-(hydroxymethyl)-4-phenylpiperidine-1-carboxylate (200 g, 0.7 mmol) were combined in tetrahydrofuran (10 mL) and cooled to 0° C. The reaction was treated with potassium tert-butoxide (156 mg, 1.4 mmol) portion wise. The reaction was stirred at 0° C. for 1 hr. The reaction mixture was diluted with water and extracted with ethyl acetate (2×). The organic layers were pooled together, washed with brine (2×), dried over magnesium sulfate, and concentrated. Column chromatography on silica gel (10% ethyl acetate/hexanes) gave 268 mg (58%).

¹H-NMR (CDCl₃, 400 MHz) δ 8.56 (s, 1H), 8.27 (s, 1H), 7.57 (s, 1H), 7.31-7.36 (m, 5H), 4.34 (s, 2H), 3.72-3.79 (m, 2H), 3.41 (s, 2H), 2.98-3.10 (m, 2H), 2.16-2.20 (m, 2H), 1.76-1.80 (m, 2H), 1.42 (s, 9H). Mass spec.: 462.22 (MH)⁺.

Intermediate 6

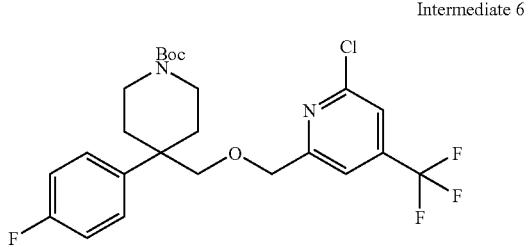

tert-butyl 4-(((6-chloro-4-(trifluoromethyl)pyridine-2-yl)methoxy)methyl)-4-(4-fluorophenyl)piperidine-1-carboxylate. 2-(bromomethyl)-6-chloro-4-(trifluoromethyl)pyridine (301 mg, 1.1 mmol) and tert-butyl 4-(hydroxymethyl)-4-(4-fluorophenyl)piperidine-1-carboxylate (309 mg, 1.0 mmol) were combined in tetrahydrofuran (20 mL) and cooled to 0° C. The reaction was treated with potassium tert-butoxide (244 mg, 2.0 mmol) portion wise. The reaction was stirred at 0° C. for 1 hr. The reaction mixture was diluted with water and extracted with ethyl acetate (2×). The organic layers were pooled together, washed with brine (2×), dried over magnesium sulfate, and concentrated. Column chromatography on silica gel (10% ethyl acetate/hexanes) gave 215 mg (43%). ¹H-NMR (CDCl₃, 400 MHz) δ 7.38 (s, 1H), 7.29-7.36 (m, 2H), 7.14 (s, 1H), 7.01-7.10 (m, 2H), 4.48 (s, 2H), 3.74-3.79 (m, 2H), 3.47 (s, 2H), 2.99-3.06 (m, 2H), 2.21-2.25 (m, 2H), 1.83-1.86 (m, 2H), 1.42 (s, 9H). Mass spec.: 403.08 (MH)⁺.

Intermediate 7

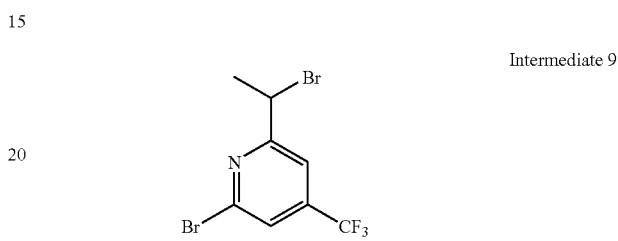

6-hydroxy-4-(trifluoromethyl)picolinaldehyde. 2-chloro-6-methyl-4-(trifluoromethyl)pyridine (2.0 g, 10.2 mmol) and selenium dioxide (3.5 g, 30.6 mmol) were dissolved in dichlorobenzene (40 ml) and heated to 180° C. and mixed for 3 hours. The reaction mixture was allowed to cool to room temperature. The precipitate was removed via vacuum filtration. Column chromatography on silica gel (10%-70% ethyl acetate/hexanes) afforded 1.00 g desired product (51%) ¹HNMR (CDCl₃ 400 MHz) δ 9.58 (s, 1H), 7.13 (s, 1H), 6.87 (s, 1H).

Intermediate 8

6-(1-hydroxyethyl)-4-(trifluoromethyl)pyridin-2-ol. 6-hydroxy-4-(trifluoromethyl)picolinaldehyde (2.00 g, 10.5 mmol) was dissolved in dry THF (20 mL) and cooled to −78° C. Methyl magnesium bromide (24 mmol) was added dropwise over 5 minutes. The mixture was allowed to mix for 15 minutes. The reaction was allowed to warm to room temperature and slowly quenched with saturated ammonium chloride (20 mL). The solution was then extracted with ethyl acetate (3×100 mL). The organic extracts were combined and washed with brine (1×) dried over sodium sulfate and concentrated to yield 1.50 g of desired product (70%). ¹HNMR (CDCl₃ 400 MHz) δ6.70 (s, 1H), 6.28 (s, 1H), 4.80 (m, 1H), 3.46 (q, 1H), 1.55 (d, 3H). Mass Spec.: 208.14 (MH)⁺.

Intermediate 9

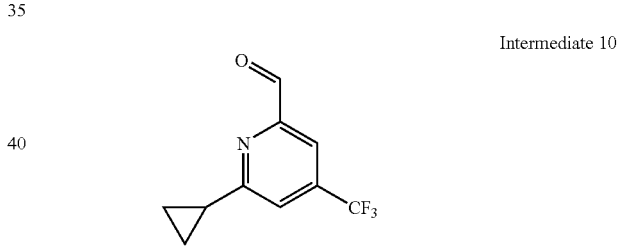

2-bromo-6-(1-bromoethyl)-4-(trifluoromethyl)pyridine. 6-(1-hydroxyethyl)-4-(trifluoromethyl)pyridin-2-ol (500 mg, 2.41 mmol) and POBr₃ (3.5 g, 10 mmol) were combined in toluene (2 mL) and heated to 110° C.° for 3 hours. Upon completion, the reaction was allowed to cool and concentrated in vacuo. Column chromatography on silica gel (99% hexanes/1% ethyl acetate) of the brown oil yielded 600 mg of desired product (75%). ¹HNMR (CDCl₃ 400 MHz) δ7.62 (d, 2H), 5.17 (q, 1H), 2.04 (d, 3H).

Intermediate 10

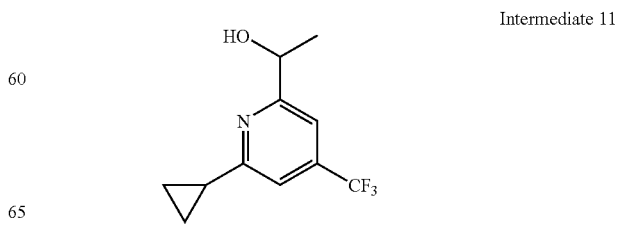

6-cyclopropyl-4-(trifluoromethyl)picolinaldehyde

Was synthesized in the same manner as 2-cyclopropyl-6-(((4-(4-fluorophenyl)-1-methylpiperidin-4-yl)methoxy)methyl)-4-(trifluoromethyl)pyridine starting from 6-bromo-4-(trifluoromethyl)picolinaldehyde. ¹H-NMR (CDCl3, 400 MHz) δ 9.99 (s, 1H), 7.87 (s, 1H), 7.56 (s, 1H) 2.18 (m, 1H), 1.20 (m, 4H). LC: T,=1.84 min, HPLC Method 1. Mass spec.: 216.37 (MH)⁺.

Intermediate 11

1-(6-cyclopropyl-4-(trifluoromethyl)pyridin-2-yl)ethanol

This compound was prepared according to the experimental condition of Intermediate 8 starting from 6-cyclopropyl-4-(trifluoromethyl)picolinaldehyde. $^1$H-NMR (CDCl3, 400 MHz) δ 7.26 (s, 1H), 7.20 (s, 1H), 4.84 (q, 1H) 2.12 (m, 1H), 1.47 (d, 3H), 1.08 (m, 4H). LC: T$_r$=1.84 min, HPLC Method 1. Mass spec.: 232.34 (MH)$^+$.

Intermediate 12

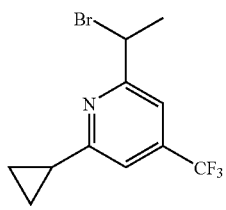

2-(1-bromoethyl)-6-cyclopropyl-4-(trifluoromethyl)pyridine

This compound was prepared according to the experimental condition of Intermediate 9 starting from 1-(6-cyclopropyl-4-(trifluoromethyl)pyridin-2-yl)ethanol. $^1$H-NMR (CDCl3, 400 MHz) δ 7.35 (s, 1H), 7.22 (s, 1H), 5.17 (q, 1H) 2.08 (m, 1H), 2.00 (d, 3H), 1.04 (m, 4H). LC: T$_r$=2.27 min, HPLC Method 1. Mass spec.: 294.32 (MH)$^+$ Intermediate 13

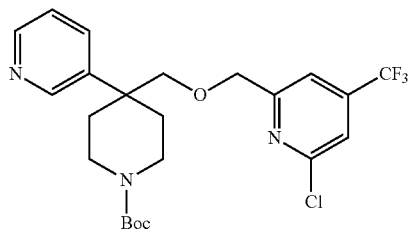

tert-butyl 4-(((6-chloro-4-(trifluoromethyl)pyridin-2-yl)methoxy)methyl)-4-(pyridin-3-yl)piperidine-1-carboxylate Synthesized using the same procedure as Intermediate 2. $^1$H-NMR (CD3OD, 400 MHz) δ 8.60 (s, 1H), 8.46 (d, 1H), 8.14 (d, 1H), 7.62 (m, 2H), 7.30 (s, 1H), 4.53 (s, 2H) 3.67 (m, 4H), 3.20 (m, 2H), 2.14 (m, 2H), 1.99 (m, 2H), 1.43 (s, 9H) LC: T$_r$=2.158 min, HPLC Method 1. Mass spec.: 486.14 (MH)$^+$.

Intermediate 14

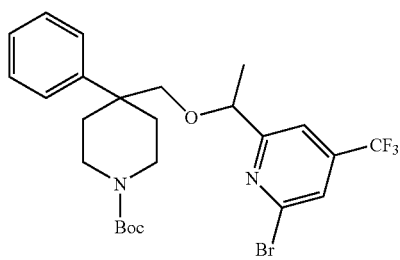

tert-butyl 4-((1-(6-bromo-4-(trifluoromethyl)pyridin-2-yl)ethoxy)methyl)-4-phenylpiperidine-1-carboxylate This compound was prepared according to the experimental condition of Intermediate 2 from 2-bromo-6-(1-bromoethyl)-4-(trifluoromethyl)pyridine and tert-butyl 4-(hydroxymethyl)-4-phenylpiperidine-1-carboxylate to afford the titled compound. $^1$HNMR (CDCl$_3$ 400 MHz) δ7.41 (m, 3H), 7.36 (m, 4H), 5.07 (q, 1H), 4.34 (m, 2H), 3.80 (m, 2H), 3.05 (m, 2H), 2.25 (m, 2H), 1.96 (m, 2H), 1.55 (s, 9H), 1.43 (d, 3H). Mass Spec.: 544.44 (MH)$^+$.

Intermediate 15

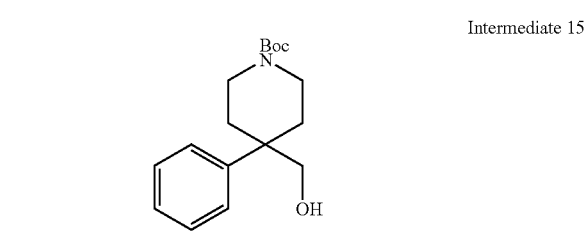

tert-butyl 4-(hydroxymethyl)-4-phenylpiperidine-1-carboxylate. To a suspension of 1-(tert-butoxycarbonyl)-4-phenylpiperidine-4-carboxylic acid (40 g, 131 mmol) in tetrahydrofuran (131 mL) at room temperature was added borane tetrahydrofuran complex (1 M in tetrahydrofuran, 131 mL, 131 mmol). There was effervescence and the substrate quickly went into solution. The reaction was stirred at room temperature for 3 days. The reaction was cooled to 0° C. and quenched by the cautious addition of 1 M sodium hydroxide. The reaction was diluted with ether, washed with water (2×), then brine, dried over magnesium sulfate, and concentrated. Trituration with 10% ethyl acetate/hexanes (300 mL) gave a white powder which was collected by filtration to give 36.9 g (97%). $^1$H-NMR (CD3OD, 300 MHz) δ 7.35-7.43 (m, 4H), 7.24-7.26 (m, 1H), 3.78-3.85 (m, 2H), 3.49 (s, 2H), 2.97 (m, 2H), 2.17-2.21 (m, 2H), 1.77-1.87 (m, 2H), 1.46 (s, 9H). Mass spec.: 292.17 (MH)$^+$.

Intermediate 16

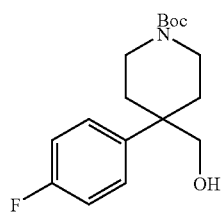

tert-butyl 4-(4-fluorophenyl)-4-(hydroxymethyl)piperidine-1-carboxylate. 1-(tert-butoxycarbonyl)-4-(4-fluorophenyl)piperidine-4-carboxylic acid (9.5 g, 29.3 mmol) was suspended in tetrahydrofuran (60 mL) and cooled to 0° C. To this solution was added borane tetrahydrofuran complex (1 M in tetrahydrofuran, 59 mL, 59 mmol) cautiously over 15 min. The reaction mixture was allowed to warm to room temperature overnight and then heated at reflux for 24 h. The mixture was cooled to 0° C., treated with excess methanol, diluted with ethyl acetate, washed with 1 N sodium hydroxide (2×), then brine (2×), dried over sodium sulfate, and concentrated. Column chromatography on silica gel (40% ethyl acetate/hexanes) gave 6.6 g (72%) as a white powder. $^1$H-NMR (CDCl$_3$, 300 MHz) 7.24-7.29 (m, 2H), 7.00-7.05 (m, 2H), 3.66-3.71 (m, 2H), 3.49 (s, 2H), 2.96-3.05 (m, 2H), 2.06-2.10

(m, 2H), 1.69-1.77 (m, 2H), 1.40 (s, 9H). Mass spec.: 310.21 (MH)+.

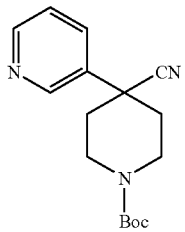

Intermediate 17 tert-butyl 4-cyano-4-(pyridin-3-yl)piperidine-1-carboxylate A flask was charged with sodium hydride (5.08 g, 127 mmol) and DMF (100 ml) at 0° C. under $N_2$. 2-(pyridin-3-yl) acetonitrile (5 g, 42.3 mmol) was added in 25 ml of DMF via addition funnel over 20 minutes. After 20 minutes tert-butyl bis(2-chloroethyl)carbamate (12.81 g, 52.9 mmol) was added in 20 ml of DMF via addition funnel over 20 minutes. The reaction was allowed to stir at 0° C. for 2 hours then at 60° C. for 12 hours. The reaction was quenched with 10% sodium bicarbonate (100 ml) and extracted with ethyl acetate (5×100 mL) The organic fractions were collected, washed with brine, dried over sodium sulfate and conc. in vacuo. The residue was purified via column chromatography (10% MeOH/ammonia 90% $CH_2Cl_2$) to yield the desired product (7.5 g, 49%). Mass Spec.: 288.20 (MH)+. LC $t_r$=1.380 min HPLC Method 1. $^1$H-NMR (CD3OD, 400 MHz) δ 8.79 (s, 1H), 8.57 (d, 1H), 8.05 (d, 1H), 8.00 (s, 1H), 7.53 (t, 1H), 4.32 (d, 2H), 3.21 (m, 2H), 2.19 (d, 2H), 2.08 (m, 2H), 1.51 (s, 9H).

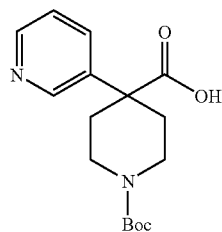

Intermediate 18

1-(tert-butoxycarbonyl)-4-(pyridin-3-yl)piperidine-4-carboxylic acid A flask was charged with tert-butyl 4-cyano-4-(pyridin-3-yl)piperidine-1-carboxylate (7.5 g, 26.1 mmol) and NaOH (100 ml, 50%) in ethanol (100 ml) and heated to reflux for 6 hours. The EtOH was removed, and the resulting solution was acidified to pH=5 using conc. HCl. The desired product was filtered, and dried overnight to yield 4.1 g (51%). Mass Spec.: 307.18 (MH)+. LC tr=1.31 min HPLC Method 1. $^1$H-NMR (CD3OD, 400 MHz) δ 8.60 (s, 1h), 8.44 (d, 1H), 7.92 (m, 1H), 7.43 (m, 1H), 3.95 (m, 2H), 3.09 (s, 2H), 2.51 (d, 2H), 1.83 (m, 2H), 1.44 (s, 9H).

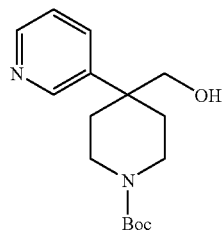

Intermediate 19 tert-butyl 4-(hydroxymethyl)-4-(pyridin-3-yl)piperidine-1-carboxylate. A flask was charged with 1-(tert-butoxycarbonyl)-4-(pyridin-3-yl)piperidine-4-carboxylic acid (4.0 g, 13.06 mmol) and tetrahydrofuran (25 mL). The reaction was placed under $N_2$. To the flask was added Borane/THF (26.1 mL of 1M soln, 26.1 mmol) and set to reflux for 2 hours. The reaction was cooled to 0° C. and quenched with MeOH (100 mL). The solution was then conc. in vacuo. The residue was purified via column chromatography (5% MeOH/95% $CH_2Cl_2$) to yield 3.2 g (84%). Mass Spec.: 293.26 (MH)+. LC: $t_r$=1.65 min HPLC Method 1. $^1$H-NMR (CD3OD, 400 MHz) δ 8.56 (s, 1H), 8.45 (d, 1H), 8.10 (d, 1H), 7.59 (m, 1H), 3.67 (m, 2H), 3.56 (s, 2H), 3.11 (t, 2H), 2.11 (d, 2H), 1.85 (m, 2H), 1.43 (s, 9H).

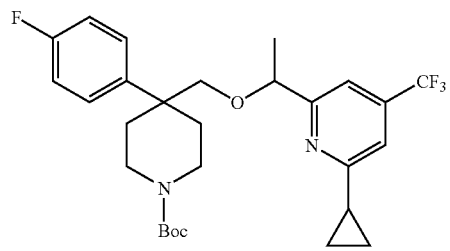

Intermediate 20 tert-butyl 4-((1-(6-cyclopropyl-4-(trifluoromethyl)pyridin-2-yl)ethoxy)methyl)-4-(4-fluorophenyl)piperidine-1-carboxylate. This compound was prepared according to the experimental condition of Intermediate 2 from 2-(1-bromoethyl)-6-cyclopropyl-4-(trifluoromethyl)pyridine. $^1$H-NMR (CDCl3, 400 MHz) δ 7.28 (m, 2H), 7.10 (s, 1H), 7.01 (m, 2H), 6.89 (s, 1H), 4.24 (q, 1H), 3.70 (m, 2H), 3.35 (m, 1H), 3.25 (m, 1H), 3.03 (m, 2H), 2.16 (m, 1H), 2.04 (m, 2H), 1.87 (m, 2H), 1.42 (s, 9H), 1.27 (d, 3H), 0.99 (m, 4H). LC: $T_r$=2.583 min, HPLC Method 1. Mass spec.: 523.67 (MH)+.

Example 1

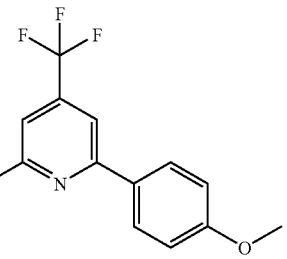

2-(4-methoxyphenyl)-6-(((4-phenylpiperidin-4-yl)methoxy)methyl)-4-(trifluoromethyl)pyridine. tert-butyl 4-(((6-chloro-4-(trifluoromethyl)pyridine-2yl)methoxy)methyl)-4-phenylpiperidine-1-carboxylate (100.0 mg, 0.21 mmol); 4-methoxyphenyl boronic acid (128.0 mg, 0.84 mmol), and tetrakis(triphenylphosphine)palladium(0) (48 mg, 0.04 mmol) were combined in dry tetrahydrofuran (3 mL) in a sealed tube. The mixture was flushed with nitrogen then 0.75 mL of a 1 N potassium hydroxide aqueous solution was introduced. The mixture was heated at 120° C. for 2 h. After cooling to room temperature, the reaction mixture was concentrated and treated with a trifluoroacetic acid/methylene chloride mixture (1:2, 3 mL) for 1 h. The solvent was removed in vacuo and the resulting crude mixture passed through a strong cation exchange column. After washing the column with several volumes of methanol, the product was eluted by washing the column with 2 M ammonia in methanol. Concentration and preparative HPLC afforded 41.0 mg (34%) of the desired compound as its TFA salt. $^1$H-NMR (CD3OD, 400 MHz) δ 7.99 (d, 2H, J=8.0 Hz), 7.86 (s, 1H), 7.31-7.49 (m, 5H), 7.24 (s, 1H), 7.01 (d, 2H, J=8.0 Hz), 4.61 (s, 2H), 3.84 (s, 3H), 3.34 (s, 2H), 3.32-3.60 (m, 2H), 2.85-2.97 (m, 2H), 2.53-2.57 (m, 2H), 2.20-2.26 (m, 2H). Mass spec.: 457.18 (MH)$^+$.

Table 2 describes compounds that were prepared by the method of Example 1. HPLC is method 1; retention time ($t_R$) is in min; NMR (CD$_3$OD, 400 MHz) unless otherwise stated.

TABLE 2

| Example | Structure | MS (MH)$^+$ | HPLC | $^1$H NMR |
|---|---|---|---|---|
| 2 | 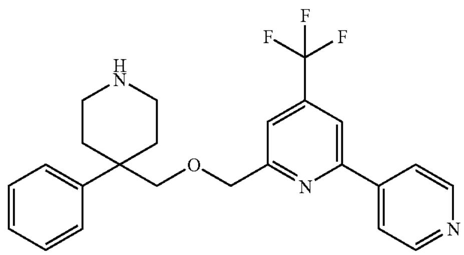 | 428.17 | 1.90 | δ 8.91 (d, 2H, J = 5.6 Hz), 8.68 (d, 2H, J = 5.6 Hz), 8.41 (s, 1H), 7.27-7.54 (m, 6H), 4.71 (s, 2H), 3.64 (s, 2H), 3.28-3.34 (m, 2H), 2.84-2.97 (m, 2H), 2.55-2.59 (m, 2H), 2.16-2.21 (m, 2H). |
| 3 | 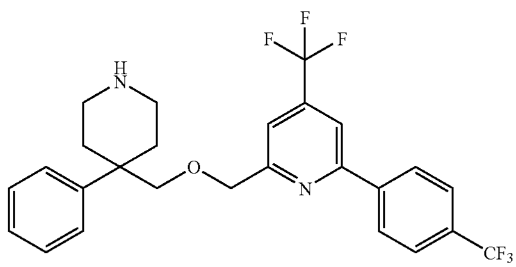 | 495.12 | 2.50 | δ 8.25 (d, 2H, J = 8.4 Hz), 8.06 (s, 1H), 7.77 (d, 2H, J = 8.4 Hz), 7.27-7.54 (m, 6H), 4.71 (s, 2H), 3.64 (s, 2H), 3.28-3.34 (m, 2H), 2.84-2.97 (m, 2H), 2.55-2.59 (m, 2H), 2.17-2.25 (m, 2H). |
| 4 | 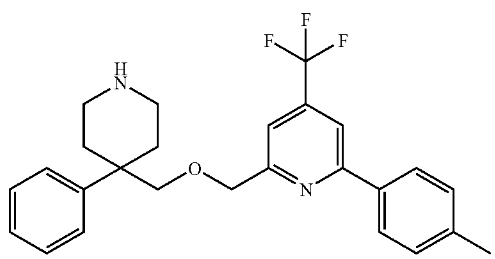 | 441.16 | 2.44 | δ 7.91 (d, 2H, J = 8.4 Hz), 7.31-7.49 (m, 7H), 7.28 (d, 2H, J = 8.4 Hz), 4.62 (s, 2H), 3.61 (s, 2H), 3.28-3.35 (m, 2H), 2.91-2.98 (m, 2H), 2.53-2.56 (m, 2H), 2.38 (s, 3H), 2.17-2.25 (m, 2H). |
| 5 | 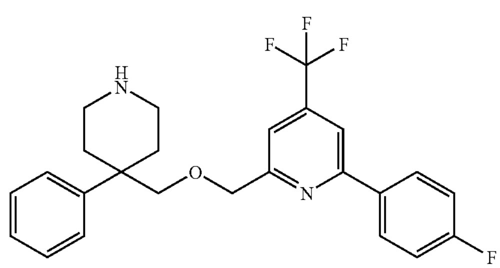 | 445.16 | 2.38 | δ 8.10 (m, 2H), 7.94 (s, 1H), 7.18-7.49 (m, 8H), 4.63 (s, 2H), 3.61 (s, 2H), 3.28-3.34 (m, 2H), 2.84-2.97 (m, 2H), 2.53-2.57 (m, 2H), 2.17-2.25 (m, 2H). |
| 6 | 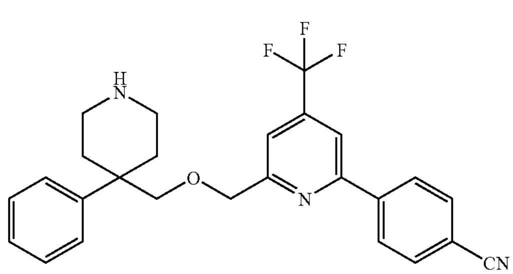 | 452.10 | 2.22 | δ 8.25 (d, 2H, J = 6.8 Hz), 8.09 (s, 1H), 7.83 (d, 2H, J = 6.8 Hz), 7.28-7.49 (m, 6H), 4.65 (s, 2H), 3.62 (s, 2H), 3.28-3.35 (m, 2H), 2.84-2.98 (m, 2H), 2.54-2.58 (m, 2H), 2.17-2.24 (m, 2H). |

TABLE 2-continued

| Example | Structure | MS (MH)+ | HPLC | ¹H NMR |
|---|---|---|---|---|
| 7 | 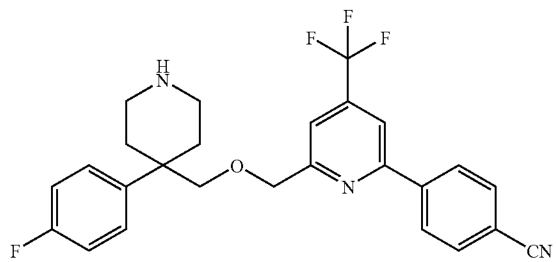 | 470.20 | 2.22 | δ 8.26 (d, 2H, J = 7.2 Hz), 8.09 (s, 1H), 7.85 (d, 2H, J = 7.2 Hz), 7.47-7.51 (m, 2H), 7.34 (s, 1H), 7.10-7.15 (m, 2H), 4.66 (s, 2H), 3.60 (s, 2H), 3.28-3.34 (m, 2H), 2.84-2.97 (m, 2H), 2.50-2.54 (m, 2H), 2.16-2.23 (m, 2H). |
| 8 | 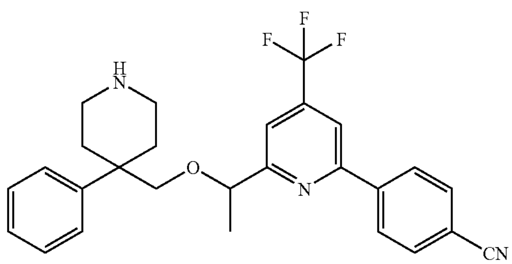 | 466.57 | 2.28 | δ 8.26 (m, 2H), 8.07 (s, 1H), 7.84 (m, 2H), 7.43 (m, 2H), 7.29 (m, 4H), 4.55 (q, 1H), 3.56 (d, 1H), 3.40 (d, 1H), 3.11 (m, 2H), 2.94 (m, 2H), 2.50 (m, 2H), 2.19 (m, 2H), 1.43 (d, 3H). |
| 9 | 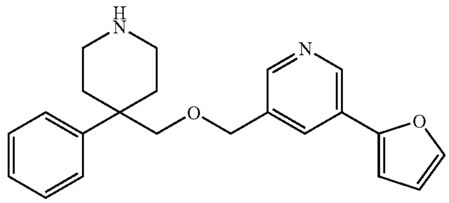 | 349.18 | 1.78 | δ 8.96 (s, 1H), 8.33-8.35 (m, 2H), 7.75 (s, 1H), 7.25-7.46 (m, 6H), 7.15 (s, 1H), 6.65 (s, 1H), 4.59 (s, 2H), 3.58 (s, 2H), 3.28-3.34 (m, 2H), 2.90-2.96 (m, 2H), 2.51-2.55 (m, 2H), 2.14-2.22 (m, 2H). |
| 10 | 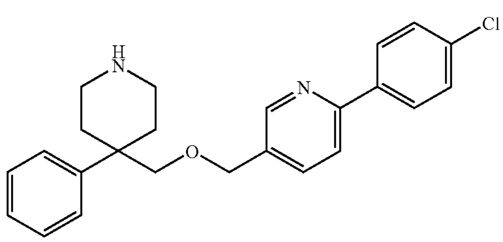 | 393.19 | 2.13 | δ 8.50 (s, 1H), 7.91 (s, 2H), 7.89 (d, 2H, J = 2.8 Hz), 7.57 (d, 2H, J = 2.8 Hz), 7.27-7.40 (m, 5H), 4.55 (s, 2H), 3.54 (s, 2H), 3.28-3.34 (m, 2H), 2.89-2.96 (m, 2H), 2.49-2.53 (m, 2H), 2.16-2.24 (m, 2H). |
| 11 | 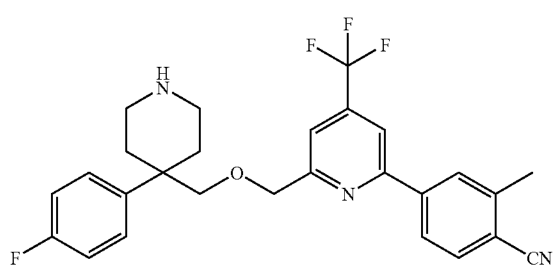 | 484.08 | 2.30 | δ 8.12 (s, 1H), 8.07 (s, 1H), 8.02 (d, 1H, J = 8.0 Hz), 7.76 (d,, 1H, J = 8.0 Hz), 7.47-7.51 (m, 2H), 7.39 (s, 1H), 7.10-7.16 (m, 2H), 4.66 (s, 2H), 3.60 (s, 2H), 3.29-3.34 (m, 2H), 2.91-2.97 (m, 2H), 2.59 (s, 3H), 2.49-2.53 (m, 2H), 2.16-2.23 (m, 2H). |
| 12 | 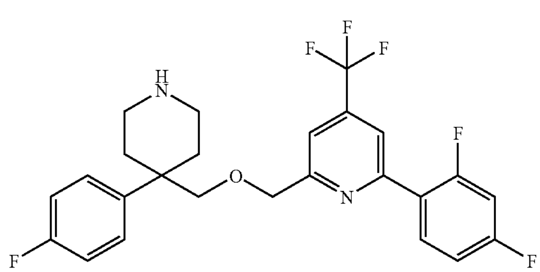 | 481.00 | 2.41 | (CDCl₃) δ 9.20 (br s, 1H), 7.92-7.98 (m, 1H), 7.92 (s, 1H), 6.88-7.30 (m, 7H), 4.60 (s, 2H), 3.51 (s, 2H), 3.30-3.34 (m, 2H), 2.92-2.95 (m, 2H), 2.45-2.48 (m, 2H), 2.18-2.25 (m, 2H). |

TABLE 2-continued

| Example | Structure | MS (MH)+ | HPLC | 1H NMR |
|---|---|---|---|---|
| 102 | 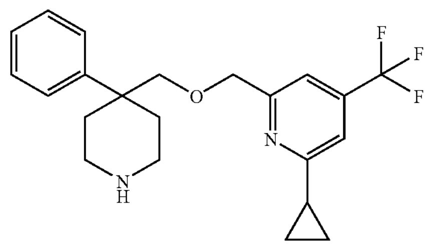 | 391.44 | 2.99 | 1H NMR (400 MHz, MeOD) δ ppm 0.88-1.08 (m, 4H) 2.03-2.27 (m, 3H) 2.52 (d, J = 15.11 Hz, 2H) 2.79-3.03 (m, 2H) 3.54 (s, 2H) 4.46 (s, 2H) 7.10 (s, 1H) 7.28 (t, J = 7.18 Hz, 1H) 7.32 (s, 1H) 7.39 (t, J = 7.68 Hz, 2+NLH) 7.42-7.46 (m, 2H) |

Example 13

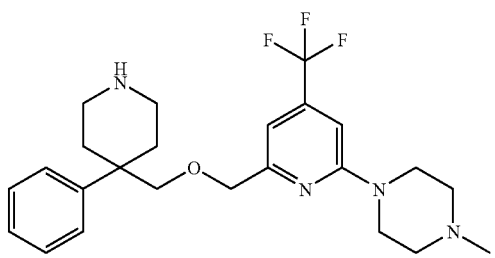

1-methyl-4-(6-(((4-phenylpiperidin-4-yl)methoxy)methyl)-4-(trifluoromethyl)pyridine-2-yl)piperazine. tert-butyl 4-(((6-chloro-4-(trifluoromethyl)pyridine-2yl)methoxy)methyl)-4-phenylpiperidine-1-carboxylate (100 mg, 0.21 mmol), sodium tert-butoxide (22 mg, 0.23 mmol), N-methyl piperizine (18 mg, 0.18 mmol), (+/−) 2,2'-bis(diphenylphosphino)-1-1'-binaphthyl (93 mg, 0.15 mmol), and tris(dibenzylideneacetone)dipalladium (0) (7.0 mg, 0.007 mmol) were combined in dry toluene (2 mL) and dimethylformamide (0.5 mL) in a sealed tube. The mixture was then heated at 120° C. for 2 h. After cooling to room temperature, the reaction mixture was concentrated and treated with a trifluoroacetic acid/methylene chloride mixture (1:2, 2 mL) for 1 h. The solvent was removed in vacuo and the resulting crude mixture passed through a strong cation exchange column. After washing the column with several volumes of methanol, the product was eluted by washing the column with 2 M ammonia in methanol. Concentration and preparative HPLC afforded 31.0 mg (26%) of the desired compound as its TFA salt. $^1$H-NMR (CD3OD, 400 MHz) δ 7.27-7.46 (m, 5H), 6.99 (s, 1H), 6.74 (s, 1H), 4.40-4.53 (m, 2H), 4.40 (s, 2H), 3.50-3.55 (m, 4H), 3.10-3.50 (m, 6H), 2.83-2.96 (m, 5H), 2.51-2.55 (m, 2H), 2.15-2.22 (m, 2H), Mass spec.: 449.24 (MH)+.

Table 3 describes compounds prepared by the method of Example 13. HPLC is method 1; retention time ($t_R$) is in min; NMR (CD$_3$OD, 400 MHz).

TABLE 3

| Example | Structure | MS (MH)+ | HPLC | 1H-NMR |
|---|---|---|---|---|
| 14 | 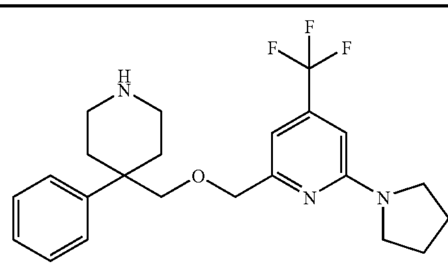 | 420.20 | 2.36 | δ 7.26-7.45 (m, 5H), 6.75 (s, 1H), 6.59 (s, 1H), 4.84 (s, 2H), 3.55 (s, 2H), 3.33-3.49 (m, 4H), 3.28-3.34 (m, 2H), 2.84-2.96 (m, 2H), 2.50-2.54 (m, 2H), 2.13-2.21 (m, 2H), 2.03-2.14 (m, 4H). |
| 15 | 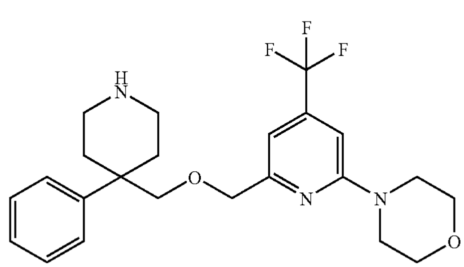 | 437.21 | 2.03 | δ 7.27-7.47 (m, 5H), 6.81 (s, 1H), 6.64 (s, 1H), 4.37 (s, 2H), 3.72-3.75 (m, 4H), 3.49-3.52 (m, 6H), 3.28-3.34 (m, 2H), 2.84-2.96 (m, (m, 2H), 2.50-2.54 (m, 2H), 2.16-2.24 (m, 2H). |

TABLE 3-continued

| Example | Structure | MS (MH)+ | HPLC | 1H-NMR |
|---|---|---|---|---|
| 16 | 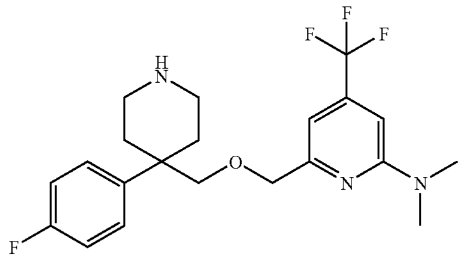 | 412.17 | 1.59 | δ 7.20-7.49 (m, 2H), 7.12-7.20 (m, 2H), 6.85 (s, 1H), 6.53 (s, 2H), 4.42 (s, 2H), 3.58 (s, 2H), 3.43-3.49 (m, 2H), 3.10 (s, 6H), 2.88-2.97 (m, 2H), 2.27-2.50 (m, 2H), 1.43-1.49 (m, 2H). |
| 17 | 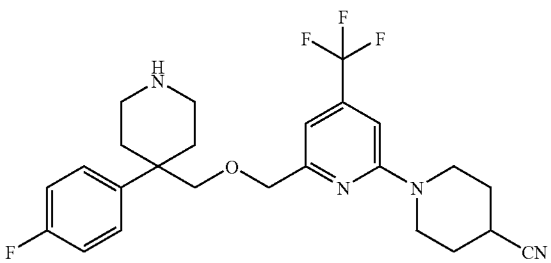 | 477.08 | 2.12 | δ 7.44-7.50 (m, 2H), 7.09-7.14 (m, 2H), 6.84 (s, 1H), 6.55 (s, 1H), 4.37 (s, 2H), 3.85-3.90 (m, 2H), 3.87 (s, 2H), 3.41-3.86 (m, 2H), 2.90-3.04 (m, 6H), 2.46-2.49 (m, 2H), 2.15-2.21 (m, 2H), 1.92-1.98 (m, 2H), 1.77-1.80 (m, 2H). |
| 18 | 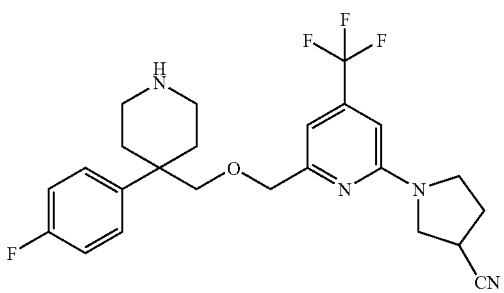 | 463.09 | 2.09 | δ 7.44-7.46 (m, 2H), 7.09-7.14 (m, 2H), 6.55-6.57 (m, 2H), 4.39 (s, 2H), 3.42-3.80 (m, 8H), 2.85-2.99 (m, 3H), 2.12-2.51 (m, 7H). |
| 19 | 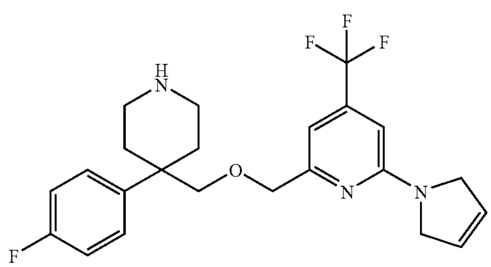 | 436.10 | 2.23 | δ 7.44-7.48 (m, 2H), 7.09-7.13 (m, 2H), 6.54-6.56 (m, 2H), 5.97 (s, 2H), 4.41 (s, 2H), 4.22 (s, 4H), 3.53 (s, 2H), 3.28-3.34 (m, 2H), 2.90-2.96 (m, 2H), 2.15-2.22 (m, 2H). |
| 20 | 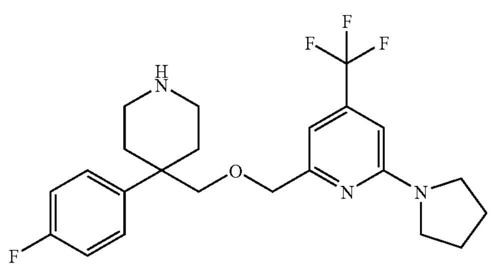 | 438.15 | 2.28 | δ 7.43-7.47 (m, 2H), 7.09-7.13 (m, 2H), 6.77 (s, 1H), 6.54 (s, 1H), 4.44 (s, 2H), 3.54 (s, 2H), 3.47-3.50 (m, 4H), 3.28-3.34 (m, 2H), 2.84-2.95 (m, 2H), 2.46-2.50 (m, 2H), 2.02-2.20 (m, 6H). |

TABLE 3-continued

| Example | Structure | MS (MH)+ | HPLC | 1H-NMR |
|---|---|---|---|---|
| 21 | 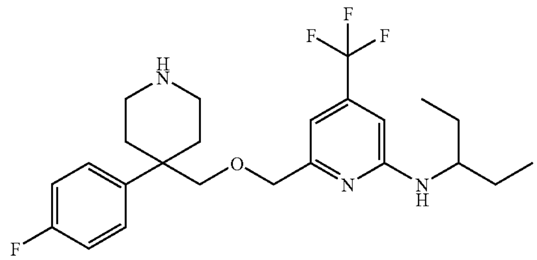 | 454.26 | 2.24 | δ 7.48-7.51 (m, 2H), 7.13-7.17 (m, 2H), 6.79 (s, 1H), 6.48 (s, 1H), 4.86 (s, 2H), 3.78-3.80 (m, 1H), 3.57 (s, 2H), 3.32-3.36 (m, 2H), 2.94-2.99 (m 2H), 2.49-2.52 (m, 2H), 2.18-2.24 (m, 2H), 1.63-1.67 (m, 2H), 1.53-1.63 (m, 2H) 0.93 (t, 6H, J = 7 Hz). |
| 22 | 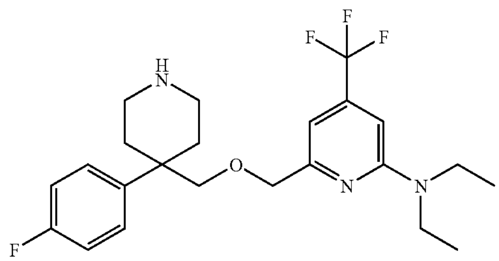 | 440.34 | 2.26 | (CDCl$_3$) δ 9.0 (br s, 1H), 7.26-7.45 (m, 2H), 7.03-7.09 (m, 2H), 6.55 (s, 1H), 6.43 (s, 1H), 4.41 (s, 2H), 3.49-3.55 (m, 4H), 3.46 (s, 2H), 3.31-3.34 (m, 2H), 2.82-2.95 (m, 2H), 2.39-2.44 (m, 2H), 2.19-2.24 (m, 2H), 1.18 (t, 6H, J = 6 Hz). |
| 23 | 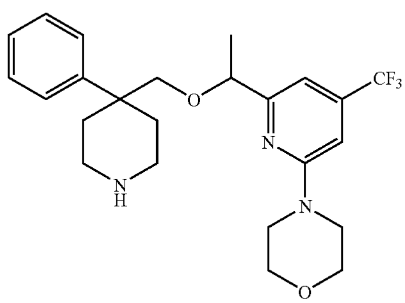 | 450.41 | 3.00 | δ 7.28-7.41 (m, 5H), 6.79 (s, 1H), 6.56 (s, 1H), 4.22 (q, 1H), 3.75 (m, 4H), 3.52 (m, 4H), 3.30 (m, 2H), 2.93 (m, 2H), 2.49 (m, 2H), 2.18 (m, 2H), 1.30 (d, 3H). |

Example 24

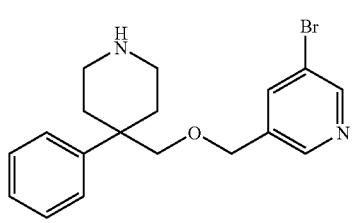

3-bromo-5-(((4-phenylpiperidin-4-yl)methoxy)methyl) pyridine. A solution of tert-butyl 4-(((5-bromopryidin-3-yl)methoxy)methyl)-4-phenylpiperidine-1-carboxylate (100 mg, 0.2 mmoL) in methylene chloride (2 mL) was treated with TFA (0.5 mL). After 1 h, the reaction was concentrated, and the resulting residue was evaporated from methylene chloride (2×). Preparative HPLC afforded 88.0 mg (92%) of the desired compound as its TFA salt. $^1$H-NMR (CDCl$_3$, 400 MHz) δ 8.65 (s, 1H), 8.52 (s, 1H), 7.84 (s, 1H), 7.24-7.43 (m, 5H), 6.85 (s, br, 1H), 4.46 (s, 2H), 3.45 (s, 2H), 3.33-3.38 (m, 2H), 2.91-2.95 (m, 2H), 2.43-2.48 (m, 2H), 2.22-2.30 (m, 2H). Mass spec.: 362.99 (MH)+.

Example 25

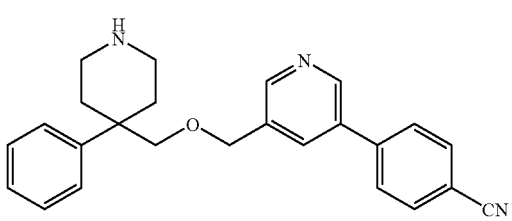

4-(5-(((4-phenylpiperidin-4-yl)methoxy)methyl)pyridine-3yl)benzonitrile. This compound was prepared according to the experimental condition of Example 1 method A from 3-bromo-5-(((4-phenylpiperidin-4-yl)methoxy)methyl)pyridine (75 mg, 0.16 mmoL), and 4-cyanobenzene boronic acid (90 mg, 0.64 mmol) to afford 50.0 mg (64%) of the desired compound as its TFA salt. $^1$H-NMR (CD3OD, 400 MHz) δ 8.99 (s, 1H), 8.52 (s, 1H), 8.25 (s, 1H), 7.92 (d, 2H, J=7.2 Hz), 7.83 (d, 2H, J=7.2 Hz), 7.21-7.46 (m, 5H), 4.64 (s, 2H), 3.58 (s, 2H), 3.32-3.60 (m, 2H), 2.89-2.96 (m, 2H), 2.51-2.56 (m, 2H), 2.21-2.22 (m, 2H). Mass spec.: 384.14 (MH)⁻.

Example 26

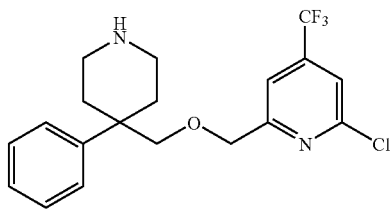

2-chloro-5-(((4-phenylpiperidin-4-yl)methoxy)methyl-4-(trifluoromethyl))pyridine. A solution tert-butyl 4-(((6-chloro-4-(trifluoromethyl)pyridine-2-yl)methoxy)methyl)-4-phenylpiperidine-1-carboxylate (50 mg, 0.1 mmoL) in methylene chloride (2 mL) was treated with TFA (0.5 mL). After 1 h, the reaction was concentrated, and the resulting residue was evaporated from methylene chloride (2×). Preparative HPLC afforded 18.0 mg (35%) of the desired compound as its TFA salt. ¹H-NMR (CD3OD, 500 MHz) δ 7.65 (s, 1H), 7.49 (d, 2H, J=8.0 Hz), 7.31-7.44 (m, 4H), 4.55 (s, 2H), 3.62 (s, 2H), 3.33-3.38 (m, 2H), 2.94-2.99 (m, 2H), 2.54-2.58 (m, 2H), 2.19-2.25 (m, 2H). Mass spec.: 385.12 (MH)⁺.

Example 27

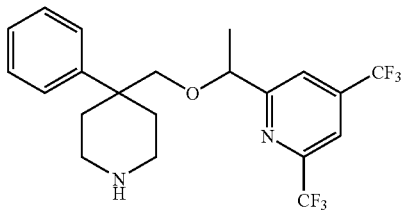

2-(1-((4-phenylpiperidin-4-yl)methoxy)ethyl)-4,6-bis(trifluoromethyl)pyridine. Tert-butyl 4-((1-(6-bromo-4-(trifluoromethyl)pyridin-2-yl)ethoxy)methyl)-4-phenylpiperidine-1-carboxylate (100 mg, 0.18 mmol), trimethyl (trifluoromethyl)silane (70 mg, 0.46 mmol), potassium fluoride (70 mg, 1.2 mmol) and Copper(I) Iodide (100 mg, 0.525 mmol) were combined in dry dimethylformamide (1 mL) and dry N-Methyl-2-pyrrolidinone (1 mL) in a sealed tube. The mixture was heated to 110° C. for 2 hours. After cooling the reaction mixture was quenched with the addition of ammonia hydroxide (6M, 15 mL). The reaction was diluted with ether, washed with brine, dried over sodium sulfate, filtered and concentrated in vacuo. The resulting oil was redissolved in methanol (2 mL) and treated with HCl (g) for 30 seconds. The solvent was evaporated and preparatory HPLC afforded 14 mg (15%) of desired product as the TFA salt. ¹H-NMR (CD3OD, 400 MHz) δ 7.92 (s, 1H), 7.24-7.57 (m, 6H), 4.54 (q, 1H), 3.91 (d, 1H), 3.57 (m, 1H), 2.82-3.03 (m, 2H), 2.51-2.77 (m, 2H), 2.34-2.48 (m, 2H), 2.03-2.22 (m, 2H), 1.38 (d, 3H). LC: T$_r$=1.785 min, HPLC Method 1. Mass spec.: 433.35 (MH)⁺.

Example 28

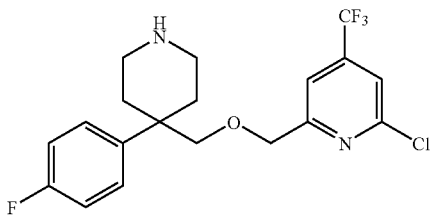

2-chloro-6-(((4-(4-fluororphenyl)piperidin-4-yl)methoxy)methyl-4-(trifluoromethyl))pyridine. A solution of tert-butyl 4-(((6-chloro-4-(trifluoromethyl)pyridine-2-yl)methoxy)methyl)-4-(4-fluorophenyl)piperidine-1-carboxylate (70 mg, 0.14 mmoL) in methylene chloride (1.5 mL) was treated with TFA (0.5 mL). After 1 h, the reaction was concentrated, and the resulting residue was evaporated from methylene chloride (2×) to afford 72.0 mg (100%) of the desired compound as its TFA salt. ¹H-NMR (CD3OD, 400 MHz) δ 7.63 (s, 1H), 7.46-7.49 (m, 2H), 7.26 (s, 1H), 7.10-7.14 (m, 2H), 4.53 (s, 2H), 3.57 (s, 2H), 3.28-3.35 (m, 2H), 2.90-2.97 (m, 2H), 2.47-2.52 (m, 2H), 2.14-2.21 (m, 2H). Mass spec.: 403.09 (MH)⁺.

Example 29

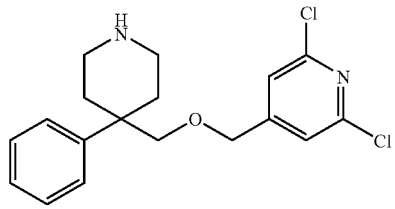

2,6-dichloro-4(((4-phenylpiperidin-4-yl)methoxy)methyl)pyridine. This compound was prepared according to the experimental condition of intermediate 5 from 4-(bromomethyl-2,6-dichloro)pyridine (131 mg, 0.55 mmoL), and tert-butyl 4-(hydroxymethyl)-4-phenylpiperidine-1-carboxylate (145 mg, 0.50 mmol) to afford 50.0 mg (22%) of the desired compound. The resulting residue was taken directly towards deprotection following the procedure outlined in Example 28 to afford 10 mg (5% overall) of the desired compound as the TFA salt. ¹H-NMR (CD3OD, 400 MHz) δ 7.34-7.48 (m, 5H), 7.10 (s, 2H), 4.43 (s, 2H), 3.49 (s, 2H), 3.29-3.40 (m, 2H), 2.89-2.96 (m, 2H), 2.50-2.56 (m, 2H), 2.15-2.19 (m, 2H). Mass spec.: 351.10 (MH)+.

Example 30

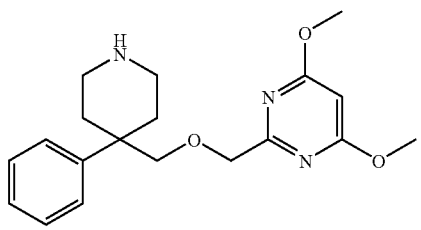

4,6-dimethoxy-2(((4-phenylpiperidin-4-yl)methoxy)methyl)pyrimidine. This compound was prepared according to the experimental condition of intermediate 5 from (4,6-dimethoxypyrimidin-2-yl)methyl chloride (281 mg, 1.5 mmoL), and tert-butyl 4-(hydroxymethyl)-4-phenylpiperidine-1-carboxylate (291 mg, 1.0 mmol) to afford 490 mg of the desired intermediate. The resulting residue was taken directly towards deprotection following the procedure outlined in Example 28 to afford 145 mg (32% overall) of the desired compound as the TFA salt. 1H-NMR (CD3OD, 400 MHz) δ 7.44 (d, 2H, J=8.0 Hz), 7.24-7.38 (m, 6H), 4.39 (s, 2H), 3.88 (s, 6H), 3.59 (s, 2H), 3.33-3.40 (m, 2H), 2.90-2.97 (m, 2H), 2.43-2.47 (m, 2H), 2.25-2.31 (m, 2H). Mass spec.: 344.21 (MH)+.

Example 31

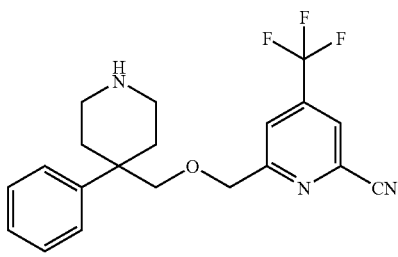

6-(((4-phenylpiperidin-4-yl)methoxy)methyl)-4-(trifluoromethyl)pyridine-2-yl)picolinonitrile. tert-butyl 4-(((6-chloro-4-(trifluoromethyl)pyridine-2yl)methoxy)methyl)-4-phenylpiperidine-1-carboxylate (200 mg, 0.40 mmol), zinc chloride (49 mg, 0.40 mmol), 1,1'-bis(diphenylphosphino)-ferrocene (27 mg, 0.05 mmol), and tris(dibenzylideneacetone)dipalladium (0) (18 mg, 0.002 mmol) were combined in H2O (0.3 mL) and dimethylformamide (3.0 mL) in a sealed tube. The mixture was then heated at 120° C. for 6 h. After cooling to room temperature, the reaction mixture was concentrated and treated with a trifluoroacetic acid/methylene chloride mixture (1:2, 2 mL) for 1 h. The solvent was removed in vacuo and the resulting crude mixture passed through a strong cation exchange column. After washing the column with several volumes of methanol, the product was eluted by washing the column with 2 M ammonia in methanol. Concentration and preparative HPLC afforded 42.0 mg (28%) of the desired compound as its TFA salt. 1H-NMR (CD3OD, 400 MHz) δ 8.09 (s, 1H), 7.58 (s, 1H), 7.27-7.47 (m, 5H), 4.79 (s, 2H), 3.60 (s, 2H), 3.28-3.34 (m, 2H), 2.84-2.97 (m, 2H), 2.52-2.56 (m, 2H), 2.13-2.21 (m, 2H), Mass spec.: 376.15 (MH)+.

Example 32

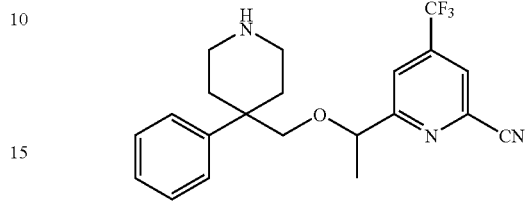

6-1-((4-phenylpiperidin-4-yl)methoxy)ethyl)-4-(trifluoromethyl)picolinonitrile. This compound was prepared according to the experimental condition of Example 33 from 2-bromo-6-(1-((4-phenylpiperidin-4-yl)methoxy)ethyl)-4-(trifluoromethyl)pyridine (100 mg, 0.18 mmoL), to afford 18 mg (20% overall) of the desired compound as the TFA salt. 1H-NMR (CD3OD, 400 MHz) δ 8.10 (s, 1H), 7.24-7.39 (m, 6H), 4.50 (q, 1H, J=7.5 Hz), 4.20 (s, 1H), 3.56 (d, 1H, J=8.0 Hz), 3.36 (d, 1H, J=8.0 Hz), 3.30-3.35 (m, 2H), 2.90-2.97 (m, 2H), 2.55-2.60 (m, 2H), 2.25-2.31 (m, 2H), 1.37 (d, 3H, J=6.5 Hz). Mass spec.: 390.17. (MH)+.

Example 33

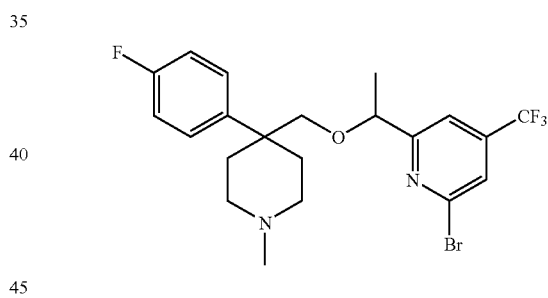

2-bromo-6-(1-((4-(4-fluorophenyl)-1-methylpiperidin-4-yl)methoxy)ethyl)-4-(trifluoromethyl)p Tert-butyl 4-((1-(6-bromo-4-(trifluoromethyl)pyridin-2-yl)ethoxy)methyl)-4-(4-fluorophenyl)piperidine-1-carboxylate (500 mg, 0.891 mmol) was dissolved in methanol (5.00 ml) and bubbled through HCl(g) for 30 seconds. The solvent was then evaporated in vacuo. The remaining tan oil was redissovled in dichloromethane (5 ml) and formaldehyde (1 ml, 36.3 mmol) under nitrogen at 0° C. and allowed to stir vigorously for 20 minutes. The reaction was then treated with sodiumtriacetoxyborohydride (755 mg, 3.56 mmol) and allowed to warm to room temperature and stir for an additional 2 hours. The reaction was quenched with 5 ml 1N NaOH, diluted with ethyl acetate, and extracted. The organic layer was washed with brine, dried over sodium sulfate, filtered, and conc. in vacuo to yield the desired product (371 mg, 88%) as a tan oil. 1H-NMR (CD3OD, 400 MHz) δ 7.71 (s, 1H), 7.58 (s, 1H), 7.41 (m, 2H), 7.06 (m, 2H), 4.36 (q, 1H), 3.94 (s, 2H), 3.53

Example 34

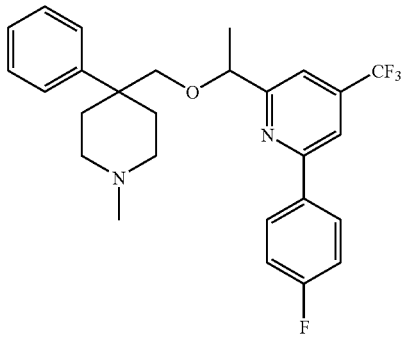

2-(4-fluorophenyl)-6-(1-(((1-methyl-4-phenylpiperidin-4-yl)methoxy)ethyl)-4-(trifluoromethyl)pyridine. 2-(4-fluorophenyl)-6-(1-((4-phenylpiperidin-4-yl)methoxy)ethyl)-4-(trifluoromethyl)pyridine (40 mg, 0.08 mmol), and formaldehyde (37 wt. % solution in water, 0.2 mL, 7.5 mmol) were combined in dichloromethane (2.0 mL) and cooled to 0° C. The reaction was treated with sodium triacetoxyborohydride (74 mg, 0.3 mmol) and a drop of acetic acid. The reaction was stirred at 0° C. for 30 min and at room temperature for 1 h. The solvent was removed in vacuo and the resulting crude mixture was concentrated and purified by preparative HPLC which afforded 10.0 mg (27%) $^1$H-NMR (CD3OD, 400 MHz) δ 8.09 (m, 1H), 7.93 (m, 1H), 7.14-7.58 (m, 9H), 4.51 (q, 1H), 3.36-3.52 (m, 2H), 2.80-2.93 (m, 2H), 2.59-2.79 (m, 5H), 2.04-2.24 (m, 2H), 1.42 (d, 3H), LC: $T_r$=1.952 min HPLC Method 1. Mass spec.: 473.36 (MH)$^+$.

Example 35

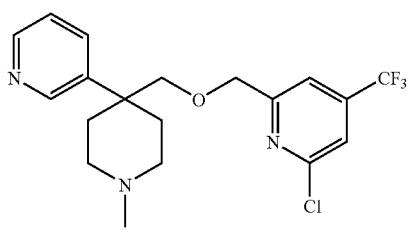

2-chloro-6-(((1-methyl-4-(pyridin-3-yl)piperidin-4-yl)methoxy)methyl)-4-(trifluoromethyl)pyridine. Synthesized in the same manner as 2-bromo-6-(1-((4-(4-fluorophenyl)-1-methylpiperidin-4-yl)methoxy)ethyl)-4-(trifluoromethyl)pyridine. $^1$H-NMR (CD3OD, 400 MHz) δ 9.00 (d, 1H), 8.82 (dd, 1H), 8.70 (d, 1H), 8.04 (s, 1H), 7.66 (d, 1H), 7.38 (d, 1H), 4.64 (s, 1H), 4.55 (s, 1H), 3.98 (s, 1H), 3.61 (s, 1H), 3.49 (m, 2H), 2.64 (m, 2H), 2.22 (m, 5H), 1.95 (m, 2H), 1.32 (d, 3H), LCMS: $T_r$=1.908, HPLC Method 1. Mass Spec: 475.44 (MH$^+$).

2H), 3.38, (m, 1H), 2.85 (m, 2H), 2.77 (s, 3H), 2.63 (m, 1H) 2.21 (m, 2H). LC: $T_r$=1.573 min, HPLC Method 1. Mass spec.: 400.14 (MH)$^+$.

Example 36

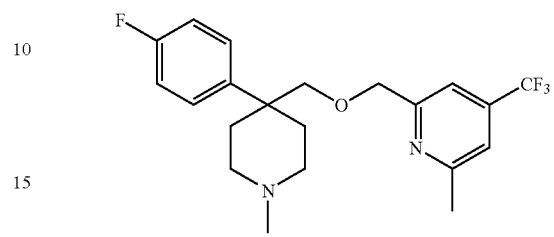

2-(((4-(4-fluorophenyl)-1-methylpiperidin-4-yl)methoxy)methyl)-6-methyl-4-(trifluoromethyl)pyridine. 2-chloro-6-(((4-(4-fluorophenyl)-1-methylpiperidin-4-yl)methoxy)methyl)-4-(trifluoromethyl)pyridine (80 mg, 0.192 mmol), tetrakis(triphenylphsophine)palladium(O) (22.18 mg, 0.019 mmol), and 2,4,6-trimethyl-1,3,5,2,4,6-trioxatriborinane (72.3 mg, 0.576 mmol) were combined in tetrahydrofuran (1.5 mL). The reaction was then treated with potassium hydroxide (0.392 ml, 0.392 mmol) and heated to 100° C. for 2 hours. After cooling, the solution was diluted with ethyl acetate (25 mL), washed with water (10 mL) and brine (10 mL). The organics were dried over sodium sulfate, filtered, and concentrated in vacuo. The resulting oil was purified via preparatory HPLC to yield the desired product (30.23 mg, 0.076 mmol, 39.7%) as the TFA salt. $^1$H-NMR (CDCl3, 400 MHz) δ 10.02 (s, 1H), 8.09 (s, 1H), 7.93 (s, 1H). LC: $T_r$=1.920 min, HPLC Method 1. Mass spec.: 397.03 (MH)$^+$.

Example 37

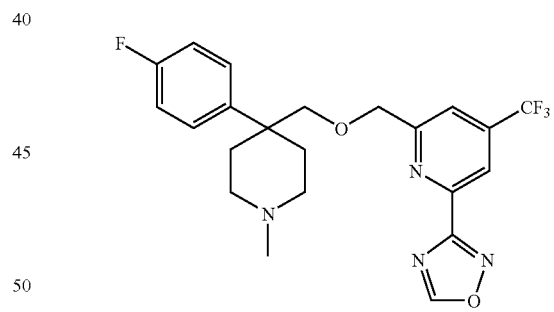

3-(6-(((4-(4-fluorophenyl)-1-methylpiperidin-4-yl)methoxy)methyl)-4-(trifluoromethyl)pyridin-2-yl)-1,2,4-oxadiazole. 6-(((4-(4-fluorophenyl)-1-methylpiperidin-4-yl)methoxy)methyl)-4-(trifluoromethyl)picolinonitrile (66 mg, 0.162 mmol) was dissolved in ethanol (1 mL) and treated with hydroxylamine (2 ml, 0.364 mmol), heated to reflux and allowed to stir for 2 hours. After cooling, the solvents were evaporated in situ. The resulting sold was dried under vacuum. The white solid was then redissolved in dichloromethane (2 mL), and treated with triethyl orthoformate (0.108 mL, 0.648 mmol) under nitrogen. The solution was then treated with boron trifluoride etherate (2.053 μL, 0.016 mmol) and allowed to stir for 2 hours at room temperature. Upon completion the reaction was concentrated in vacuo and purified via preparatory HPLC to yield the desired product (19.8 mg, 27.1%) as the TFA salt. $^1$H-NMR (CD3OD, 400 MHz) δ 9.48 (s, 1H), 8.29 (s, 1H), 7.58 (m, 3H), 7.18 (m, 2H), 4.73 (s, 2H), 3.59 (s, 2H), 3.50 (m, 2H), 2.89 (t, 2H), 2.79 (s, 3H), 2.75 (d, 2H), 2.22 (t, 2H), LC: T$_r$=1.736 min HPLC Method 1. Mass spec.: 451.46 (MH)$^+$.

Example 38

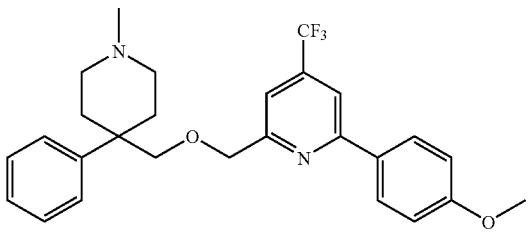

2-(4-methoxyphenyl)-6-(((1-methyl-4-phenylpiperidin-4-yl)methoxy)methyl)-4-(trifluoromethyl)pyridine. 2-(4-methoxyphenyl)-6-(((4-phenylpiperidin-4-yl)methoxy)methyl)-4-(trifluoromethyl)pyridine (23 mg, 0.05 mmol) and formaldehyde (37 wt. % solution in water, 0.2 mL, 7.5 mmol) were combined in acetonitrile (4.0 mL) and cooled to 0° C. The reaction was treated with sodium cyanoborohydride (16 mg, 0.25 mmol) and a drop of acetic acid. The reaction was stirred at 0° C. for 30 min and at room temperature for 1 h. The solvent was removed in vacuo and the resulting crude mixture was concentrated and purified by preparative HPLC which afforded 15.0 mg (51%). $^1$H-NMR (CD3 OD, 400 MHz) δ 7.99 (d, 2H, J=8.5 Hz), 7.87 (s, 1H), 7.26-7.48 (m, 6H), 7.02 (d, 2H, J=8.5 Hz), 4.61 (s, 2H), 3.83 (s, 3H), 3.54 (s, 2H), 3.32-3.60 (m, 2H), 2.73-2.89 (m, 2H), 2.59-2.69 (m, 5H), 2.20-2.26 (m, 2H). Mass spec.: 471.20 (MH)$^+$.

Table 4 describes compounds that were prepared by the method of Example 38. HPLC is method 1; retention time (t$_R$) is in min; NMR (CD$_3$OD, 400 MHz) unless otherwise stated.

TABLE 4

| Example | Structure | MS (MH)$^+$ | HPLC | $^1$H NMR |
|---|---|---|---|---|
| 39 | 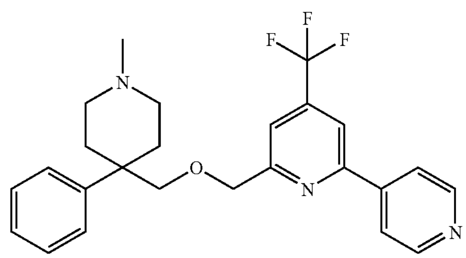 | 442.19 | 1.94 | δ 8.80 (d, 2H, J = 6.8 Hz), 8.44 (d, 2H, J = 6.5 Hz), 8.32 (s, 1H), 7.30-7.53 (m, 6H), 4.69 (s, 2H), 3.58 (s, 2H), 3.34-3.50 (m, 2H), 2.84-2.93 (m, 2H), 2.74 (s, 3H), 2.71-2.74 (m, 2H), 2.15-2.23 (m, 2H). |
| 40 | 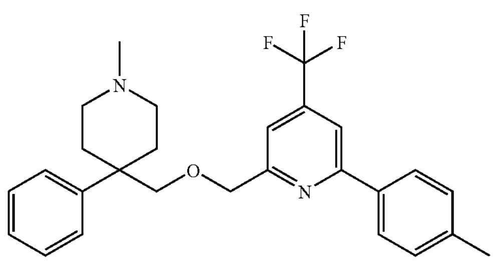 | 455.20 | 2.52 | δ 7.96 (d, 2H, J = 6.4 Hz), 7.29-7.54 (m, 9H), 4.68 (s, 2H), 3.59 (s, 2H), 3.33-3.49 (m, 2H), 2.86-2.93 (m, 2H), 2.73 (s, 3H), 2.61-2.66 (m, 2H), 2.42 (s, 3H), 2.12-2.27 (m, 2H). |
| 41 | 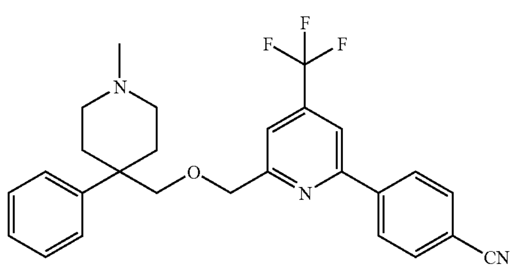 | 466.20 | 2.02 | δ 8.26 (d, 2H, J = 6.8 Hz), 8.09 (s, 1H), 7.84 (d, 2H, J = 6.8 Hz), 7.30-7.50 (m, 6H), 4.66 (s, 2H), 3.56 (s, 2H), 3.40-3.46 (m, 2H), 2.84-2.91 (m, 2H), 2.75 (s, 3H), 2.71-2.74 (m, 2H), 2.15-2.24 (m, 2H). |
| 42 | 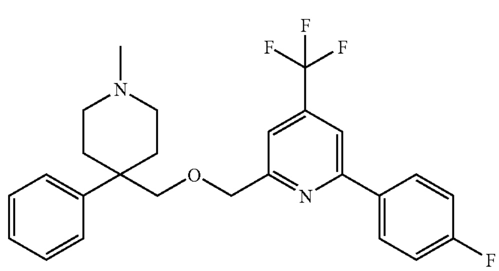 | 459.17 | 2.37 | δ 8.10 (m, 2H), 7.95 (s, 1H), 7.17-7.50 (m, 8H), 4.63 (s, 2H), 3.55 (s, 2H), 3.45-3.47 (m, 2H), 2.83-2.90 (m, 2H), 2.74 (s, 3H), 2.71-2.74 (m, 2H), 2.16-2.28 (m, 2H). |

TABLE 4-continued
| Example | Structure | MS (MH)+ | HPLC | ¹H NMR |
|---|---|---|---|---|
| 43 | 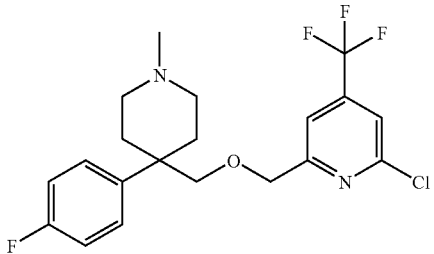 | 417.15 | 2.03 | δ 7.63 (s, 1H), 7.63 (s, 1H), 7.41-7.50 (m, 2H), 7.30 (s, 1H), 7.07-7.16 (m, 2H), 4.53 (s, 2H), 3.84 (s, 2H), 3.31-3.39 (m, 2H), 2.84-2.87 (m, 2H), 2.74 (s, 3H), 2.59-2.69 (m, 2H), 2.11-2.19 (m, 2H). |
| 44 | 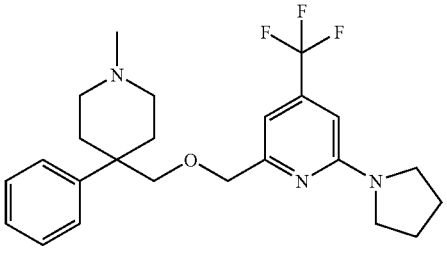 | 434.22 | 2.25 | δ 7.28-7.47 (m, 5H), 6.70 (s, 1H), 6.60 (s, 1H), 4.56 (s, 2H), 3.42-3.83 (m, 8H), 2.80-2.87 (m, 2H), 2.73 (s, 3H), 2.66-2.70 (m, 2H), 2.10-2.22 (m, 2H), 2.02-2.10 (m, 4H). |
| 45 | 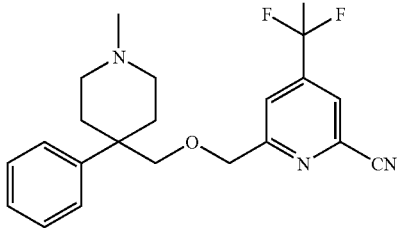 | 390.16 | 1.99 | δ 8.09 (s, 1H), 7.61 (s, 1H), 7.30-7.49 (m, 5H), 4.63 (s, 2H), 3.54 (s, 2H), 3.43-3.46 (m, 2H), 2.73-2.88 (m, 2H), 2.73 (s, 3H), 2.65-2.69 (m, 2H), 2.13-2.21 (m, 2H). |
| 46 | 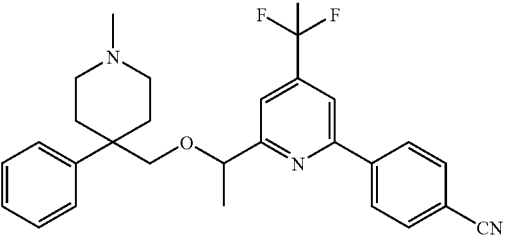 | 480.64 | 3.02* | δ 8.25 (m, 2H), 8.05 (s, 1H), 7.84 (m, 2H), 7.41 (m, 2H), 7.35 (m, 1H), 7.23 (m, 3H), 4.50 (q, 1H), 3.56 (d, 1H), 3.39 (d, 1H), 2.91 (m, 2H), 2.49 (m, 2H), 2.40 (s, 1H), 2.37 (m, 2H), 1.40 (d, 3H). |
| 47 | 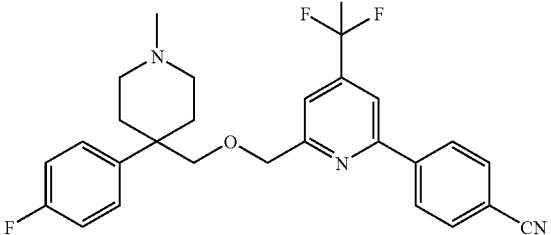 | 484.23 | 2.23 | δ 8.83 (d, 2H, J = 6.0 Hz), 8.09 (s, 1H), 7.83 (d, 2H, J = 6.0 Hz), 7.08-7.51 (m, 5H), 4.67 (s, 2H), 3.54 (s, 2H), 3.43-3.49 (m, 2H), 2.82-2.88 (m, 2H), 2.75 (s, 3H), 2.67-2.74 (m, 2H), 2.14-2.22 (m, 2H). |

TABLE 4-continued

| Example | Structure | MS (MH)+ | HPLC | ¹H NMR |
|---|---|---|---|---|
| 48 | 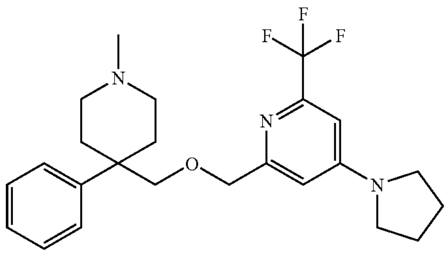 | 434.26 | 2.16 | δ 7.28-7.48 (m, 5H), 6.90 (s, 1H), 6.51 (s, 1H), 4.79 (s, 2H), 3.48 (s, 2H), 3.42-3.45 (m, 6H), 2.82 (s, 3H), 2.82-2.85 (m, 2H), 2.67-2.73 (m, 2H), 2.06-2.17 (m, 6H). |
| 49 | 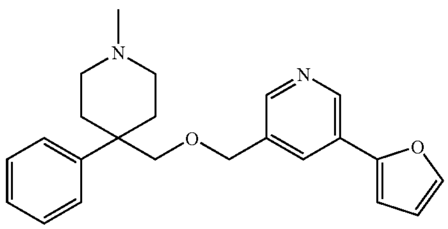 | 363.16 | 1.83 | δ 8.95 (s, 1H), 8.29 (s, 1H), 8.20 (s, 1H), 7.72 (s, 1H), 7.27-7.46 (m, 5H), 7.07 (s, 1H), 6.63 (s, 1H), 4.57 (s, 2H), 3.45 (s, 2H), 3.28-3.34 (m, 2H), 2.83-2.93 (m, 2H), 2.71 (s, 3H), 2.51-2.55 (m, 2H), 2.12-2.20 (m, 2H). |
| 50 | 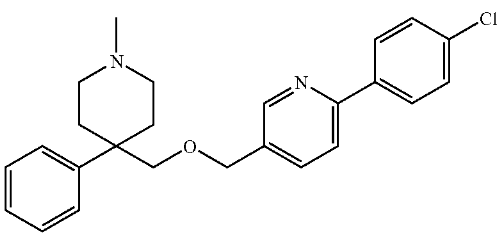 | 407.21 | 2.20 | δ 8.65 (s, 1H), 7.91 (s, 2H), 7.89 (d, 2H, J = 2.8 Hz), 7.56 (d, 2H, J = 2.8 Hz), 7.29-7.43 (m, 5H), 4.56 (s, 2H), 3.48 (s, 2H), 3.42-3.45 (m, 2H), 2.81-2.87 (m, 2H), 2.73 (s, 3H), 2.65-2.68 (m, 2H), 2.16-2.25 (m, 2H). |
| 51 | 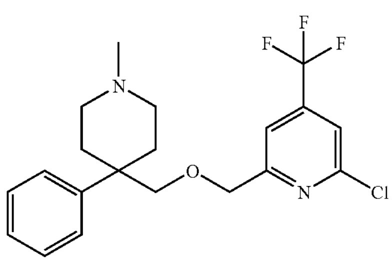 | 399.17 | 2.13 | δ 7.61 (s, 1H), 7.32-7.49 (m, 5H), 7.29 (s, 1H), 4.55 (s, 2H), 3.73 (s, 2H), 3.51 (s, 3H) 3.43-3.49 (m, 2H), 2.73-2.93 (m, 2H), 2.73-2.91 (m, 2H), 2.13-2.21 (m, 2H). |
| 52 | 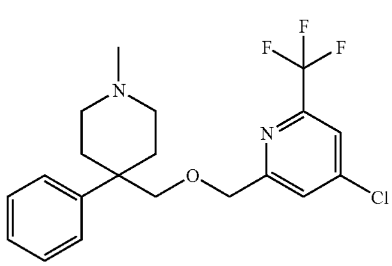 | 399.17 | 2.12 | δ 7.73 (s, 1H), 7.31-7.49 (m, 6H), 4.55 (s, 2H), 3.50 (s, 2H), 3.43-3.49 (m, 2H), 2.74-2.88 (m, 2H), 2.71 (s, 3H), 2.68-2.82 (m, 2H), 2.15-2.23 (m, 2H). |
| 53 | 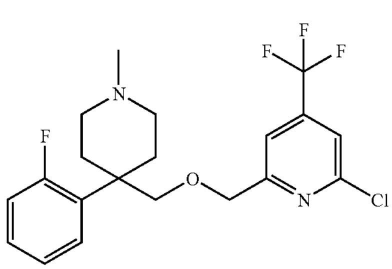 | 417.01 | 2.18 | (CDCl$_3$) δ 7.42 (s, 1H), 7.10-7.41 (m, 5H), 4.55 (s, 2H), 3.65 (s, 2H), 3.55-3.58 (m, 2H), 2.73-2.83 (m, 2H), 3.51 (s, 3H), 2.24-2.39 (m, 4H). |

TABLE 4-continued

| Example | Structure | MS (MH)+ | HPLC | ¹H NMR |
|---|---|---|---|---|
| 54 | 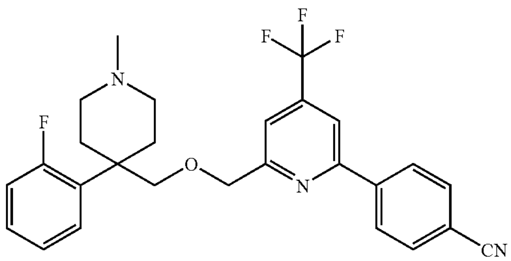 | 484.11 | 2.25 | (CDCl₃) δ 8.09 (d, 2H, J = 7.5 Hz), 7.42-7.80 (m, 3H), 7.10-7.37 (m, 5H), 4.62 (s, 2H), 3.97-4.19 (m, 2H), 3.68 (s, 2H), 3.61-3.64 (m, 2H), 2.69-2.84 (m, 5H), 2.22-2.30 (m, 2H). |
| 55 | 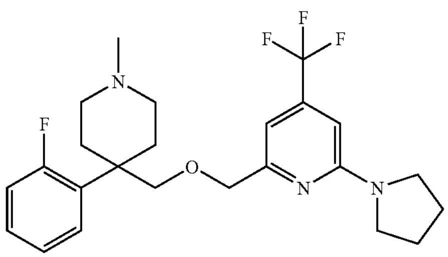 | 452.17 | 2.35 | (CDCl₃) δ 6.98-7.35 (m, 4H), 6.65 (s, 1H), 6.51 (s, 1H), 3.52-3.94 (m, 12H), 2.56-2.83 (m, 5H), 2.27-2.33 (m, 2H), 2.04-2.09 (m, 4H). |
| 56 | 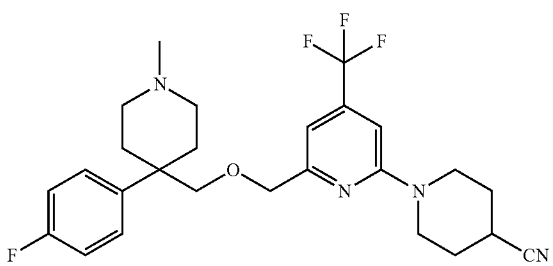 | 419.64 | 2.20 | δ 7.41-7.59 (m, 2H), 7.11-7.15 (m, 2H), 6.85 (s, 1H), 6.58 (s, 1H), 4.40 (s, 2H), 3.85-3.91 (m, 2H), 3.44-3.47 (m, 4H), 2.63-3.00 (m, 10H), 2.14-2.21 (m, 2H), 1.76-1.98 (m, 4H). |
| 57 | 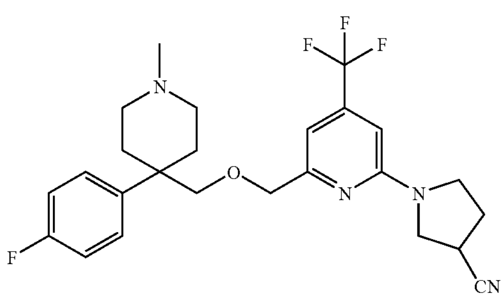 | 477.18 | 2.10 | δ 7.42-7.48 (m, 2H), 7.07-7.15 (m, 2H), 6.54-6.60 (m, 2H), 4.39 (s, 2H), 3.41-3.79 (m, 8H), 2.84-2.91 (m, 8H), 2.12-2.51 (m, 4H). |
| 58 | 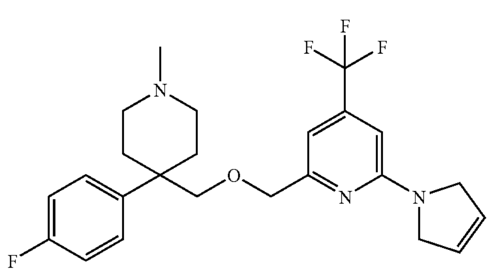 | 450.12 | 2.27 | δ 7.39-7.49 (m, 2H), 7.04-7.15 (m, 2H), 6.57 (s, 2H), 5.97 (s, 2H), 4.44 (s, 2H), 4.22 (s, 4H), 3.47 (s 2H), 3.31-3.46 (m, 2H), 2.74-2.86 (m, 2H), 2.66 (s, 3H), 2.63-2.66 (m, 2H), 2.13-2.20 (m, 2H). |

TABLE 4-continued

| Example | Structure | MS (MH)+ | HPLC | ¹H NMR |
|---|---|---|---|---|
| 59 | 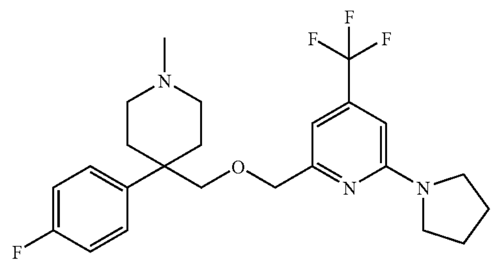 | 452.14 | 2.27 | δ 7.39-7.48 (m, 2H), 7.05-7.15 (m, 2H), 6.72 (s, 1H), 6.55 (s, 1H), 4.45 (s, 2H), 3.47 (s, 2H), 3.29-3.46 (m, 4H), 2.83-2.86 (m, 2H), 2.79 (s, 3H), 2.67-2.74 (m, 2H), 2.02-2.19 (m, 8H). |
| 60 | 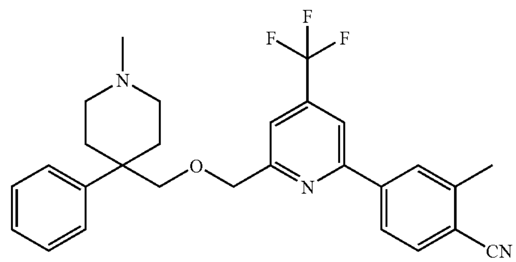 | 480.14 | 2.32 | δ 8.12 (s, 1H), 8.07 (s, 1H), 8.02 (d, 1H, J = 8.0 Hz), 7.76 (d,, 1H) J = 8.0 Hz), 7.27-7.51 (m, 6H), 4.66 (s, 2H), 3.56 (s, 2H), 3.31-3.46 (m, 2H), 3.15-3.28 (m, 2H), 2.91-2.97 (m, 2H), 2.70 (s, 3H), 2.57 (s, 3H), 2.16-2.23 (m, 2H). |
| 61 | 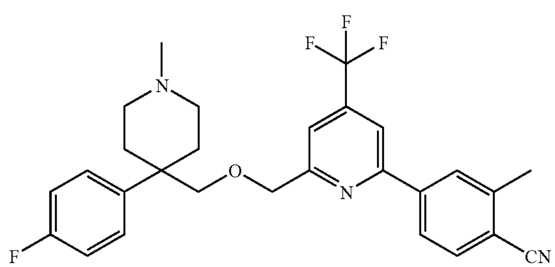 | 498.06 | 2.27 | δ 8.11 (s, 1H), 8.06 (s, 1H), 8.03 (d, 1H, J = 8.0 Hz), 7.73 (d,, 1H, J = 8.0 Hz), 7.42-7.52 (m, 2H), 7.35 (s, 1H), 7.10-7.20 (m, 2H), 4.68 (s, 2H), 3.54 (s, 2H), 3.43-3.46 (m, 2H), , 2.75-2.91 (m, 2H), 2.71 (s, 3H), 2.59-2.67 (m, 2H), 2.58 (s, 3H), 2.14-2.21 (m, 2H). |
| 62 | 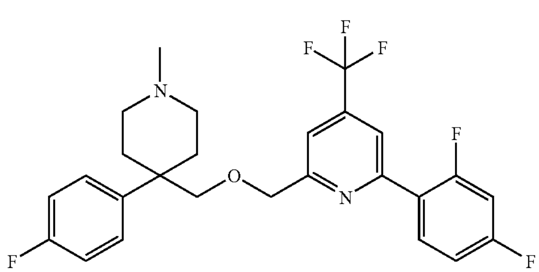 | 495.13 | 2.43 | (CDCl₃) δ 7.84-7.92 (m, 1H), 7.80 (s, 1H), 6.88-7.31 (m, 7H), 4.59 (s, 2H), 3.58-3.62 (m, 2H), 3.48 (s, 2H), 2.83 (s, 3H), 2.27-2.83 (m, 4H), 2.19-2.27 (m, 2H). |
| 63 | 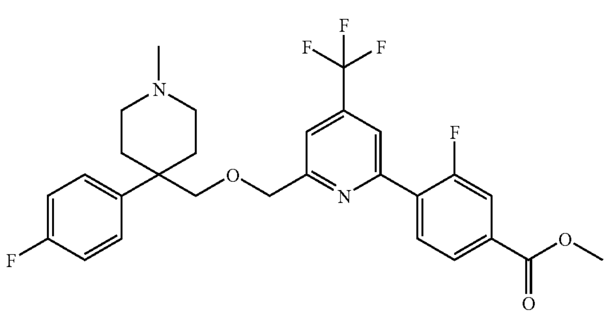 | 535.29 | 1.96* | (CDCl₃) δ 8.02-8.05 (m, 1H), 7.91-7.93 (m, 3H), 7.82 (d, 1H, J = 2.2 Hz) 7.30-7.33 (m, 2H), 7.10-7.14 (m, 3H), 4.60 (s, 2H), 3.95 (s, 3H), 3.50-3.58 (m, 2H), 3.43 (s, 2H), 2.68 (s, 3H), 2.54-2.65 (m, 2H), 2.30-2.37 (m, 2H). |

TABLE 4-continued

| Example | Structure | MS (MH)+ | HPLC | 1H NMR |
|---|---|---|---|---|
| 64 | 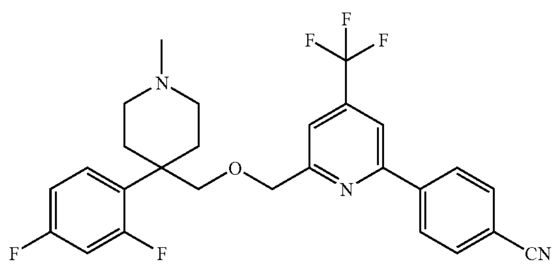 | 502.08 | 2.09 | δ 8.25 (d, 2H, J = 8.0 Hz), 8.11 (s, 1H), 7.85 (d, 2H, J = 8.0 Hz), 7.37-7.48 (m, 1H), 7.37 (s, 1H), 6.95-7.05 (m, 2H), 4.69 (s, 2H), 3.69 (s, 2H), 3.37-4.50 (m, 2H) 2.81-3.92 (m, 4H), 2.79 (s, 3H), 2.07-2.14 (m, 2H). |
| 65 | 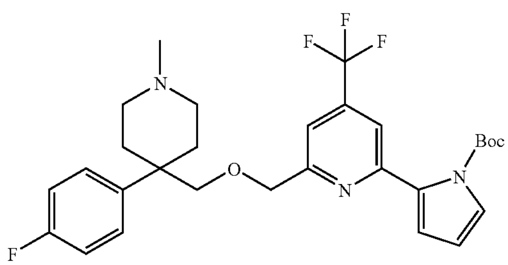 | 548.17 | 2.61 | (CDCl$_3$) δ 7.31-7.41 (m, 3H), 7.15 (s, 1H), 7.00-7.05 (m, 3H), 6.43 (s, 1H), 6.22 (s, 1H), 4.52 (s, 2H), 3.49 (s, 2H), 2.52-2.59 (m, 2H), 2.23 (s, 3H), 2.00-2.22 (m, 2H), 1.58 (s, 9H), 1.12-1.36 (m, 2H), 0.83-1.09 (m, 2H). |
| 66 | 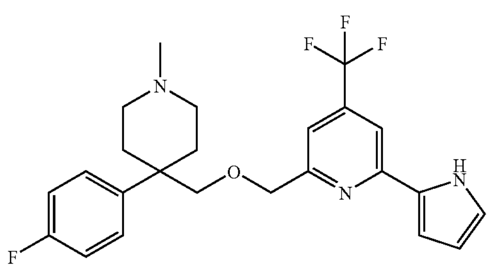 | 448.15 | 2.04 | (CDCl$_3$) δ 7.59 (s, 1H), 7.28-7.31 (m, 2H), 6.99-7.05 (m, 2H), 7.00 (s, 1H), 6.84-6.91 (m, 2H), 6.32 (s, 1H), 4.56 (s, 2H), 3.54-3.62 (m, 2H), 3.49-3.54 (m, 2H), 3.47 (s, 2H), 2.70 (s, 3H), 2.62-2.69 (m, 2H), 2.50-2.54 (m, 2H), 2.31-2.39 (m, 2H). |
| 67 | 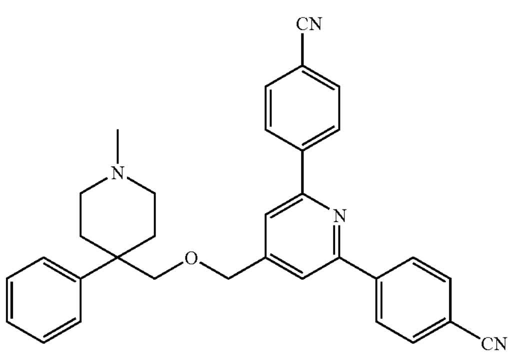 | 499.34 | 2.29 | δ 810 (d, 4H, J = 8.0 Hz), 7.76 (d, 4H, J = 8.0 Hz), 7.33-7.57 (m, 7H), 4.53 (s, 2H), 3.54-3.57 (m, 2H), 3.47 (s, 2H), 3.33-3.42 (m, 2H), 2.69 (s, 3H), 2.56-2.60 (m, 2H), 2.37-2.40 (m, 2H). |
| 68 | 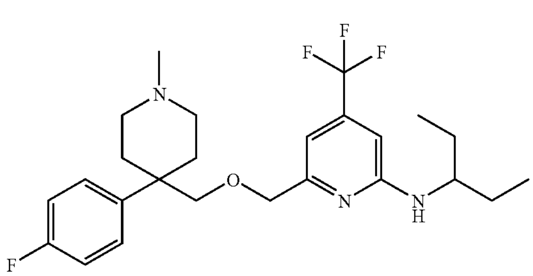 | 468.27 | 2.23 | δ 7.44-7.47 (m, 2H), 7.08-7.13 (m, 2H), 6.50 (s, 1H), 6.36 (s, 1H), 4.31 (s, 2H), 3.78-3.80 (m, 1H), 3.51 (s, 2H), 3.32-3.36 (m, 2H), 2.94-2.99 (m 2H), 2.70 (s, 3H), 2.49-2.52 (m, 2H), 2.20-2.26 (m, 2H), 1.54-1.59 (m, 2H), 1.39-1.46 (m, 2H) 0.87 (t, 6H, J = 12 Hz).. |

TABLE 4-continued

| Example | Structure | MS (MH)+ | HPLC | $^1$H NMR |
|---|---|---|---|---|
| 69 | 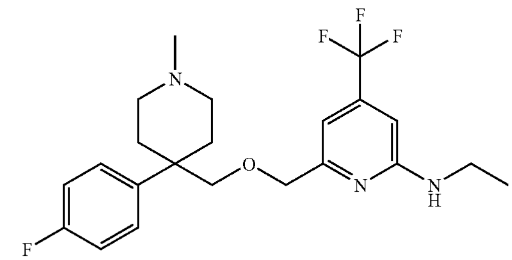 | 426.25 | 1.76 | δ, 8.49 (s, 2H), 7.46-7.49 (m, 2H), 7.09-7.13 (m, 2H), 4.64 (s, 2H), 3.59 (s, 2H), 3.29-3.32 (m, 4H), 2.84-2.88 (m 2H), 2.69 (s, 3H), 2.47-2.51 (m, 2H), 2.21-2.26 (m, 2H), 1.93 (m, 3H). |
| 70 | 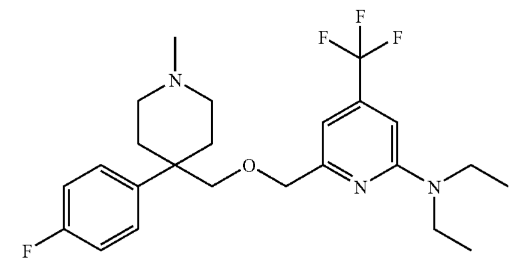 | 454.22 | 2.20* | (CDCl$_3$) δ 7.26-7.31 (m, 2H), 7.02-7.12 (m, 2H), 6.49 (s, 1H), 6.33 (s, 1H), 4.32 (s, 2H), 3.44-3.57 (m, 4H), 3.43 (s, 2H), 2.79-2.83 (m, 2H), 2.68 (s, 3H), 2.51-2.63 (m, 2H), 2.33-2.36 (m, 2H), 2.27-2.30 (m, 2H), 1.16 (t, 6H, J = 6 Hz). |
| 71 | 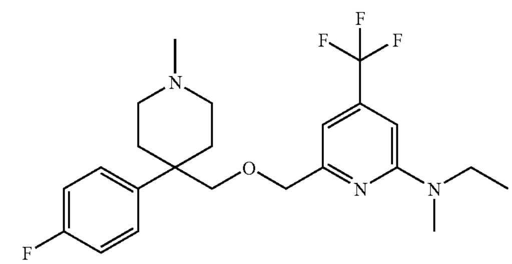 | 440.32 | 2.17 | (CDCl$_3$) δ 7.26-7.31 (m, 2H), 7.02-7.12 (m, 2H), 6.53 (s, 1H), 6.35 (s, 1H), 4.37 (s, 2H), 3.51-3.64 (m, 2H), 3.42 (s, 2H), 3.09 (s, 3H), 2.79-2.83 (m, 2H), 2.67 (s, 3H), 2.50-2.60 (m, 2H), 2.27-2.33 (m, 2H), 1.13 (t, 6H, J = 6 Hz). |
| 72 | 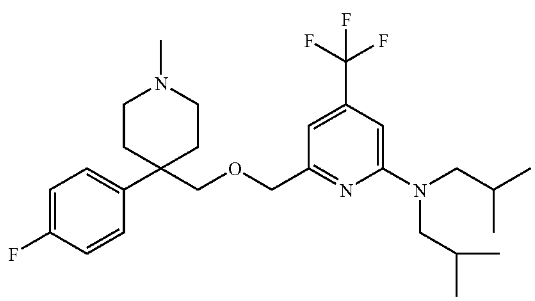 | 510.32 | 2.60* | (CDCl$_3$) δ 7.29-7.31 (m, 2H), 7.02-7.12 (m, 2H), 6.45 (s, 1H), 6.27 (s, 1H), 4.33 (s, 2H), 3.42 (s, 2H), 3.35-3.52 (m, 4H), 3.27 (d, 4H, J = 7.2 Hz), 2.76-2.86 (m, 2H), 2.55 (s, 3H), 2.24-2.31 (m, 2H), 1.99-2.02 (m, 2H), 1.13 (d, 12H, J = 6.8 Hz). |
| 73 | 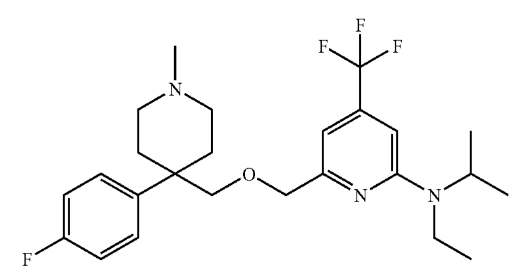 | 468.21 | 2.30* | (CDCl$_3$) δ 7.27-7.31 (m, 2H), 7.00-7.08 (m, 2H), 6.55 (s, 1H), 6.35 (s, 1H), 4.67-4.70 (m, 1H), 4.38 (s, 2H), 3.52-3.55 (m, 2H), 3.44 (s, 2H), 3.35-3.46 (m, 2H), 2.74-2.83 (m, 2H), 2.67 (s, 3H), 2.50-2.64 (m, 2H), 2.26-2.33 (m 2H), 1.15-1.23 (m, 9H). |

TABLE 4-continued

| Example | Structure | MS (MH)+ | HPLC | ¹H NMR |
|---|---|---|---|---|
| 74 | 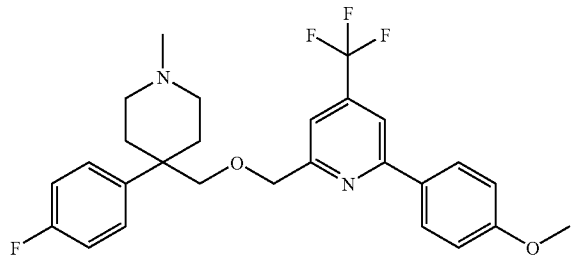 | 490.39 | 2.14 | (CDCl₃) δ 7.92 (d, 2H, J = 12 Hz), 7.66 (s, 1H), 6.95-7.33 (m, 7H), 4.64 (s, 2H), 3.86 (s, 3H), 3.52-3.55 (m, 2H), 3.48 (s, 2H), 2.73-2.84 (m, 2H), 2.64 (s, 3H), 2.53-2.61 (m, 2H), 2.27-2.34 (m, 2H). |
| 75 | 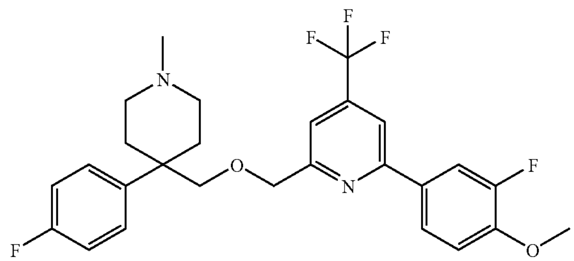 | 507.14 | 2.17 | (CDCl₃) δ 7.65-7.77 (m, 3H), 7.30-7.33 (m, 2H), 6.99-7.14 (m, 4H), 4.64 (s, 2H), 3.94 (s, 3H), 3.53-3.56 (m, 2H), 3.48 (s, 2H), 2.73-2.84 (m, 2H), 2.69 (s, 3H), 2.53-2.61 (m, 2H), 2.33-2.37 (m, 2H). |
| 76 | 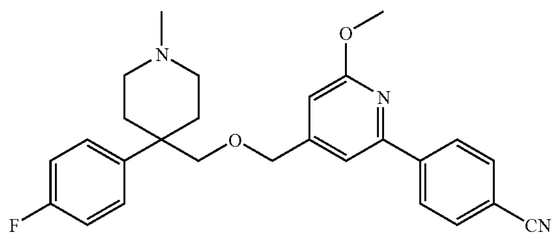 | 446.34 | 2.09 | (CDCl₃) δ 8.00 (d, 2H, J = 7.0 Hz), 7.71 (d, 2H, J = 7.0 Hz), 7.28-7.30 (m, 2H), 7.07-7.09 (m, 2H), 6.95 (s, 1H), 6.44 (s, 1H), 4.37 (s, 2H), 4.00 (s, 3H), 3.48-3.52 (m, 2H), 3.37 (s, 2H), 2.78-2.84 (m, 2H), 2.66 (s, 3H), 2.34-2.65 (m, 4H). |
| 77 | 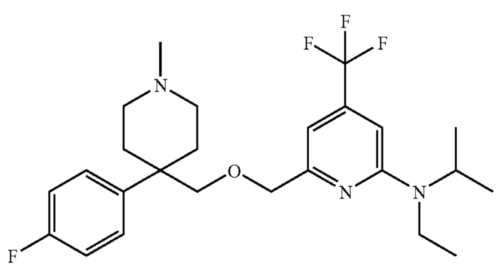 | 450.32 | 2.27* | (CDCl₃) δ 7.27-7.43 (m, 5H), 6.42 (s, 1H), 6.29 (s, 1H), 4.67-4.70 (m, 1H), 4.36 (s, 2H), 3.49-3.51 (m, 2H), 3.46 (s, 2H), 3.29-3.34 (m, 2H), 2.55-2.67 (m, 5H), 2.50-2.55 (m, 2H), 2.26-2.32 (m, 2H), 1.11-1.18 (m, 9H). |
| 78 | 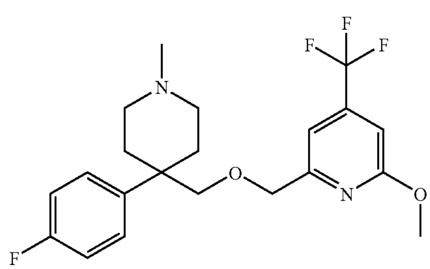 | 413.28 | 2.03 | (CDCl₃) δ 7.25-7.32 (m, 2H), 7.09-7.13 (m, 2H), 6.76 (s, 1H), 6.64 (s, 1H), 4.39 (s, 2H), 3.90 (s, 3H), 3.52-3.55 (m, 2H), 3.45 (s, 2H), 2..67 (s 3H), 2.64-2.67 (m, 2H), 2.52-2.64 (m, 2H), 2.27-2.23 (m, 2H). |
| 79 | 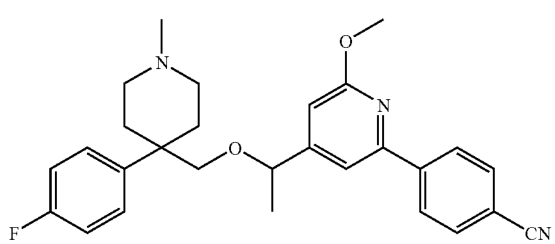 | 460.33 | 2.21 | (CDCl₃) δ 7.96 (d, 2H, J = 8.0 Hz), 7.70 (d, 2H, J = 8.0 Hz), 7.22-7.26 (m, 2H), 7.04-7.08 (m, 2H), 6.86 (s, 1H), 6.33 (s, 1H), 4.18-4.20 (m, 1H), 4.96 (s, 3H), 3.49-3.53 (m, 2H), 3.17-3.24 (m, 2H), 2.65 (s, 3H), 2.57-2.61 (m, 2H), 2.31-2.36 (m, 4H), 1.31 (d, 3H, J = 6.5 Hz). |

TABLE 4-continued

| Example | Structure | MS (MH)+ | HPLC | 1H NMR |
|---------|-----------|----------|------|--------|
| 80 | 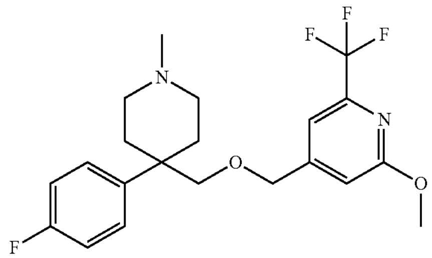 | 413.34 | 2.07 | (CDCl3) δ 7.25-7.29 (m, 2H), 7.10-7.14 (m, 2H), 6.85 (s, 1H), 6.55 (s, 1H), 4.42 (s, 2H), 3.93 (s, 3H), 3.50-3.53 (m, 2H), 3.37 (s, 2H), 2.35-2.50 (m, 5H), 2.34-2.37 (m, 2H), 2.28-2.32 (m, 2H). |
| 81 | 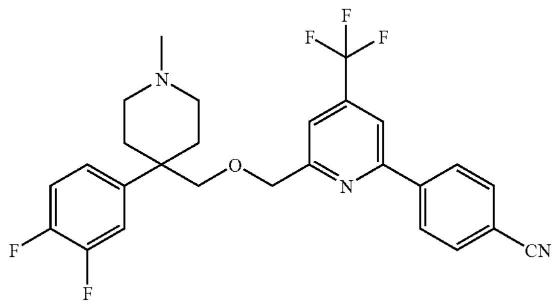 | 502.16 | 3.08* | δ 8.09 (d, J = 8.0 Hz, 2H), 7.78 (s, 1H), 7.76 (d, J = 8.0 Hz, 2H), 7.09-7.24 (m, 4H), 4.61 (s, 2H), 3.53 (s, 2H), 2.28-2.52 (br m, 9H), 1.49-1.56 (br m, 2H). |
| 82 | 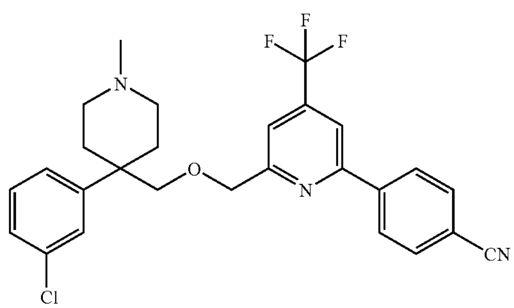 | 500.09 | 1.72* | δ 8.09 (d, J = 8.0 Hz, 2H), 7.77 (s, 1H), 7.76 (d, J = 8.0 Hz, 2H), 7.36 (s, 1H), 7.21-7.32 (br m, 4H), 4.60 (s, 2H), 3.54 (s, 2H), 2.69 (br m, 2H), 2.28 (br m, 7H), 2.08 (br m, 2H). |
| 83 | 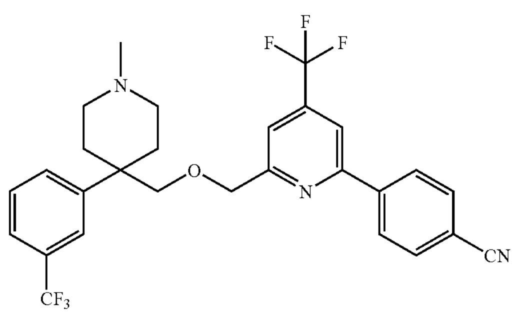 | 534.08 | 1.73* | δ 8.07 (d, J = 6.0 Hz, 2H), 7.74 (m, 3H), 7.45-7.62 (m, 4H), 7.22 (s, 1H), 4.58 (s, 2H), 3.56 (s, 2H), 2.64 (br m, 2H), 2.18-2.34 (br m, 7H), 2.05-2.12 (br m, 2H). |
| 84 | 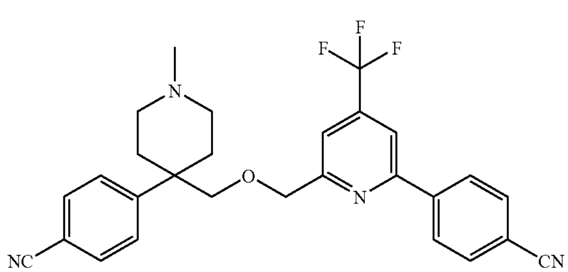 | 491.14 | 2.29* | δ 8.09 (d, J = 8.0 Hz, 2H), 7.78 (s, 1H), 7.76 (d, J = 8.0 Hz, 2H), 7.65 (d, J = 8.0 Hz, 2H), 7.51 (d, J = 8.0 Hz, 2H), 7.18 (s, 1H), 4.59 (s, 2H), 3.57 (s, 2H), 2.59 (br m, 2H), 2.23 (br m, 7H), 2.04 (br m, 2H). |

TABLE 4-continued

| Example | Structure | MS (MH)+ | HPLC | ¹H NMR |
|---|---|---|---|---|
| 85 | 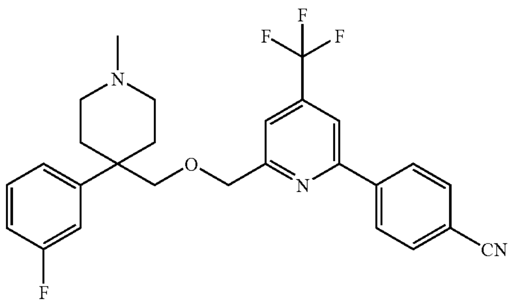 | 484.13 | 1.65* | δ 8.09 (d, J = 8.0 Hz, 2H), 7.76 (m, 3H), 7.34 (m, 1H), 7.25 (s, 1H), 7.16 (m, 1H), 7.09 (m, 1H), 6.96 (m, 1H), 4.60 (s, 2H), 3.55 (s, 2H), 2.70 (br m, 2H), 2.31-2.34 (br m, 7H), 2.13 (m, 2H). |
| 86 | 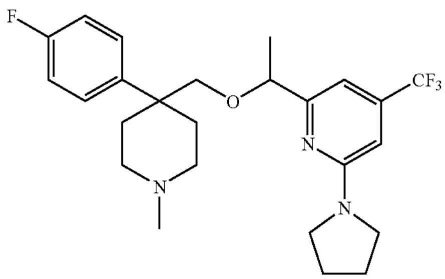 | 466.15 | 1.86 | δ 7.46 (m, 2H), 7.16 (m, 2H), 6.52 (s, 1H), 6.44 (s, 1H), 4.29 (q, 1H), 3.46 (m, 6H), 2.59-2.98 (m, 10H), 2.78, (s, 3H), 2.19 (m, 2H), 1.36 (d, 3H) |
| 87 | 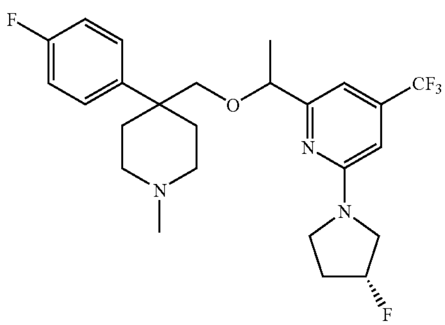 | 484.63 | 1.86 | δ 7.47 (m, 2H), 7.13 (m, 2H), 6.57 (d, 2H), 5.43 (m, 1H), 5.30 (s, 1H) 4.25 (m, 1H), 3.80 (m, 2H), 3.67 (m, 2H), 3.46 (m, 3H), 2.83 (t, 2H), 2.74 (s, 3H), 2.63 (m, 2H), 2.34 (m, 2H), 2.18 (m, 2H), 1.32 (d, 3H) |
| 88 | 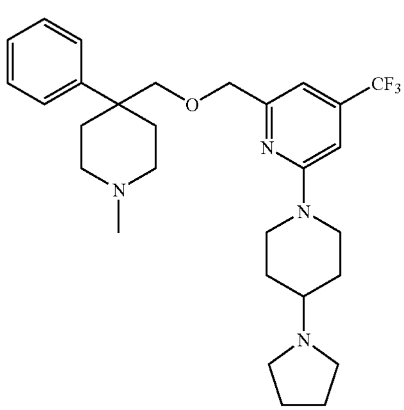 | 517.44 | 1.59 | δ 7.50 (m, 5H), 6.93 (s, 1H), 6.70 (s, 1H), 4..55 (d, 2H), 4.41 (m, 2H), 3.86 (1H, s), 3.67 (s, 2H), 3.17 (m, 2H), 2.96 (m, 6H), 2.19 (m, 5H), 2.21 (m, 8H), 2.00 (m, 2H), 1.65 (m, 2H). |

TABLE 4-continued

| Example | Structure | MS (MH)+ | HPLC | ¹H NMR |
|---|---|---|---|---|
| 89 | 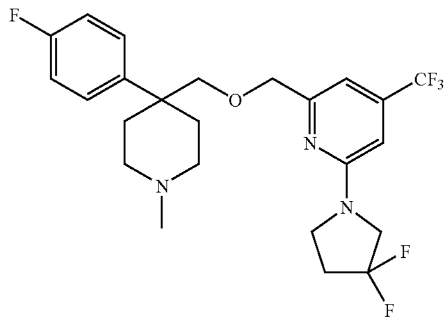 | 488.14 | 1.87 | δ 7.52 (m, 2H), 7.17 (m, 2H), 6.67 (s, 1H), 6.60 (s, 1H), 4.44 (m, 2H), 3.84 (m, 2H), 3.69 (m, 2H), 3.26-3.38 (m, 4H), 2.89 (t, 2H), 2.78 (s, 3H), 2.67 (d, 2H), 2.53 (m, 2H), 2.21 (m, 2H). |
| 90 | 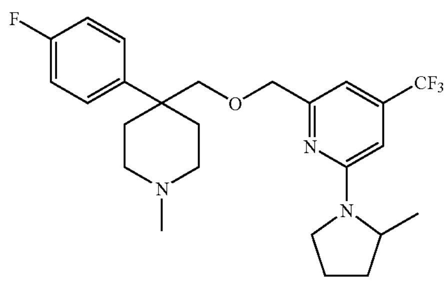 | 466.17 | 1.78 | δ 7.46 (m, 2H), 7.14 (m, 2H), 6.58 (s, 1H), 6.52 (s, 1H), 4.40 (s, 2H) 4.18 (m, 1H), 3.40-3.57 (m, 5H), 3.26-3.37 (m, 2H), 2.84 (t, 2H), 2.74 (s, 3H), 2.63 (d, 2H), 1.96-2.24 (m, 5H), 1.16 (d, 3H). |
| 91 | 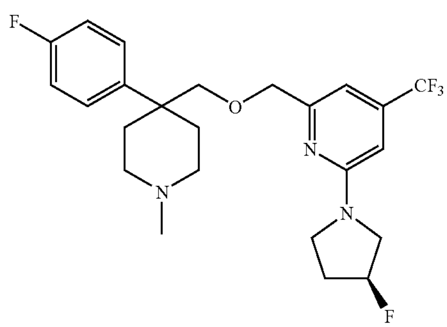 | 470.18 | 1.71 | δ 7.47 (m, 2H), 7.13 (m, 2H), 6.57 (d, 2H), 5.43 (m, 1H), 5.30 (s, 1H) 4.41 (d, 2H), 3.80 (m, 2H), 3.67 (m, 2H), 3.46 (m, 3H), 2.83 (t, 2H), 2.74 (s, 3H), 2.63 (m, 2H), 2.34 (m, 2H), 2.18 (m, 2H). |
| 92 | 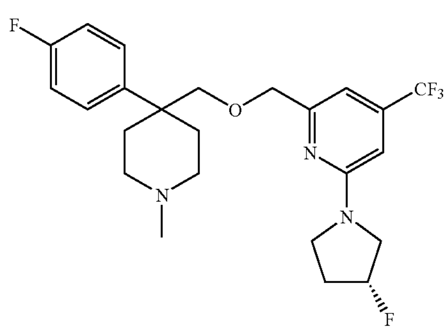 | 470.18 | 1.69 | δ 7.47 (m, 2H), 7.13 (m, 2H), 6.57 (d, 2H), 5.43 (m, 1H), 5.30 (s, 1H) 4.41 (d, 2H), 3.80 (m, 2H), 3.67 (m, 2H), 3.46 (m, 3H), 2.83 (t, 2H), 2.74 (s, 3H), 2.63 (m, 2H), 2.34 (m, 2H), 2.18 (m, 2H). |
| 93 | 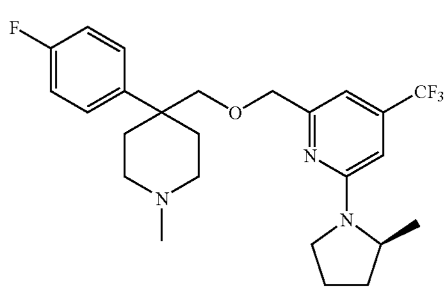 | 466.13 | 1.80 | δ 7.46 (m, 2H), 7.14 (m, 2H), 6.51 (d, 2H), 4.40 (s, 2H) 4.18 (m, 1H), 3.40-3.57 (m, 5H), 3.26-3.37 (m, 2H), 2.84 (t, 2H), 2.74 (s, 3H), 2.63 (d, 2H), 1.96-2.24 (m, 5H), 1.16 (d, 3H). |

TABLE 4-continued

| Example | Structure | MS (MH)+ | HPLC | ¹H NMR |
|---|---|---|---|---|
| 94 | 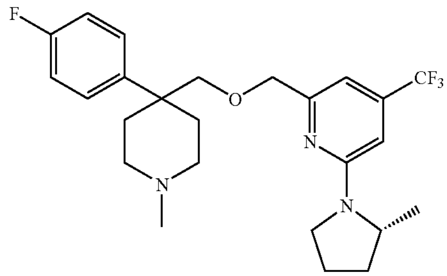 | 466.24 | 1.78 | δ 7.46 (m, 2H), 7.14 (m, 2H), 6.50 (d, 2H), 4.40 (s, 2H) 4.18 (m, 1H), 3.40-3.57 (m, 5H), 3.26-3.37 (m, 2H), 2.84 (t, 2H), 2.74 (s, 3H), 2.63 (d, 2H), 1.96-2.24 (m, 5H), 1.16 (d, 3H) |
| 95 | 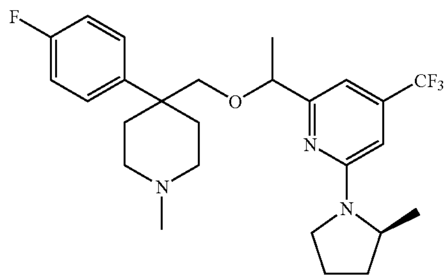 | 480.31 | 1.98 | δ 7.48 (m, 2H), 7.16 (m, 2H), 6.48 (d, 1H), 6.43 (d, 1H), 4.16-4.33 (m, 2H), 3.46 (m, 3H), 3.27 (m, 2H), 2.59-2.96 (m, 4H), 2.78 (s, 3H), 2.12 (m, 5H), 1.77 (m, 2H), 1.37 (m, 3H), 1.21 (d, 3H). |
| 96 | 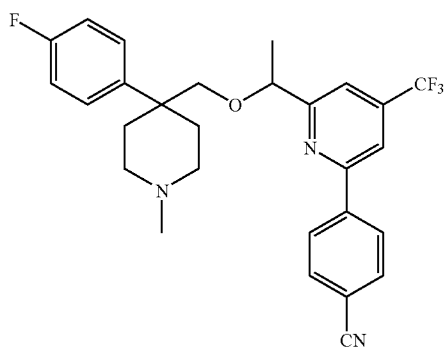 | 498.31 | 1.88 | δ 8.10 (m, 2H), 7.77 (m, 2H), 7.30 (m, 3H), 7.19 (s, 1H), 7.03 (m, 2H), 4.45 (q, 1H), 3.46 (d, 1H), 3.30 (d, 1H), 2.69 (m, 2H), 1.98-2.37 (m, 7H), 1.62 (m, 2H), 1.40 (d, 3H). |
| 97 | 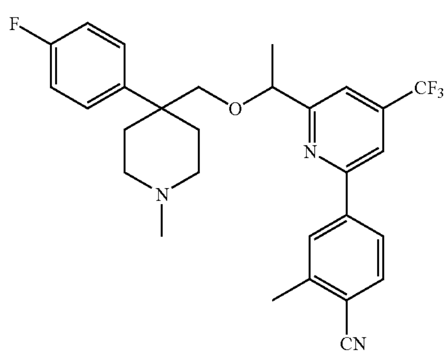 | 512.26 | 1.98 | δ 8.12 (s, 1H), 8.04 (s, 2H), 7.76 (d, 2H), 7.44 (q, 2H), 7.19 (s, 1H), 7.10 (t, 2H), 4.54 (q, 1H), 3.24-3.41 (m, 2H), 2.90 (m, 2H), 2.71 (s, 3H), 2.59 (s, 3H), 2.41 (m, 2H), 2.18 (m, 2H), 1.42 (d, 3H). |

TABLE 4-continued

| Example | Structure | MS (MH)+ | HPLC | ¹H NMR |
|---|---|---|---|---|
| 98 | 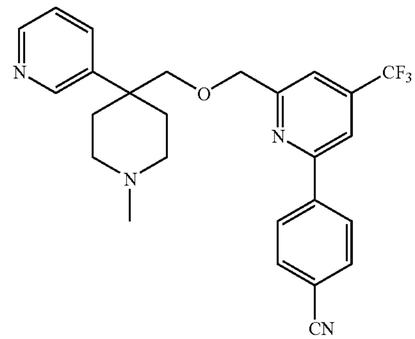 | 467.14 | 1.36 | δ 8.95 (d, 1H), 8.75 (dd, 1H), 8.59 (d, 1H), 8.23 (d, 2H), 8.13 (s, 1H), 7.96 (m, 1H), 7.86 (d, 2H), 7.40 (d, 1H), 4.75 (s, 1H), 4.68 (s, 1H), 4.01 (s, 1H), 3.65 (s, 1H), 3.53 (m, 2H), 3.31, (m, 2H), 2.85 (m, 2H), 2.78 (s, 3H), 2.20 (m, 2H). |
| 103 | 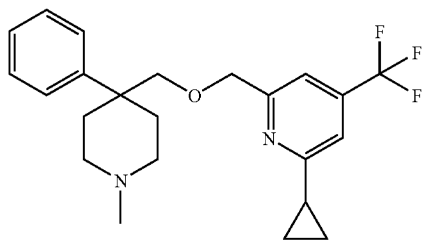 | 405.47 | 2.626 | 1H NMR (400 MHz, MeOD) δ ppm 0.92-1.01 (m, 4H) 2.04-2.20 (m, 3+NLH) 2.32-2.49 (m, 5H) 2.55 (t, J = 10.20 Hz, 2H) 2.98 (d, J = 12.09 Hz, 2H) 4.41 (s, 2H) 4.62 (s, 2H) 7.03-7.08 (m, 1H) 7.21 (t, J = 7.18 Hz, 1H) 7.27 (s, 1H) 7.34 (t, J = 7.81 Hz, 2H) 7.38-7.44 (m, 2H) |

HPLC method 1: Xterra C18 2.0×50 mm, A=95% H₂O/5% ACN, B=95% ACN/5% H₂O, Modifier 10 mM NH₄OAC, Flow rate=4.0 mL/min, 0-100% B, Gradient. Time=3 min.

Phenomenex C18 4.6×50 mm, 10% MeOH/90% H₂O/0.1% TFA→90% MeOH/10% H₂O/0.1% TFA, Gradient time=4 min., Flow rate=4 mL/min.

Example 99

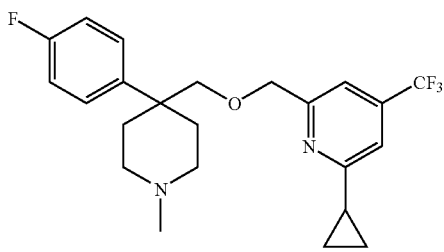

2-cyclopropyl-6-(((4-(4-fluorophenyl)-1-methylpiperidin-4-yl)methoxy)methyl)-4-(trifluoromethyl)pyridine. 2-chloro-6-(((4-(4-fluorophenyl)-1-methylpiperidin-4-yl)methoxy)methyl)-4-(trifluoromethyl)pyridine (50 mg, 0.120 mmol), cyclopropylboronic acid (30.9 mg, 0.360 mmol) PdCl2(dppf)-CH2Cl2Adduct (9.80 mg, 0.012 mmol), cesium carbonate (121 mg, 0.372 mmol) were combined in toluene (1 ml). The reaction was flushed with nitrogen and heated to 100° C. for 2 hours. After cooling, the reaction was quenched with 10 ml saturated sodium bicarbonate, and diluted with ethyl acetate. The organics were then washed with brine, dried over sodium sulfate, filtered, and concentrated in vacuo. The resulting oil was purified via preparatory HPLC and the desired product (34.8 mg, 0.082 mmol, 68.7%) was submitted as the TFA salt. ¹H-NMR (CD3OD, 400 MHz) δ 7.48 (m, 2H), 7.33 (m, 1H), 7.14 (t, 2H), 7.08 (m, 1H), 4.47 (m, 2H), 3.46 (m, 4H), 2.84 (m, 2H), 2.74 (s, 3H), 2.67 (m, 2H), 2.13 (m, 3H), 0.97 (m, 4H). LC: T$_r$=1.850 min, HPLC Method 1. Mass spec.: 423.27 (MH)⁺.

| Example | Structure | MS (MH)+ | HPLC | ¹H NMR |
|---|---|---|---|---|
| 100 | 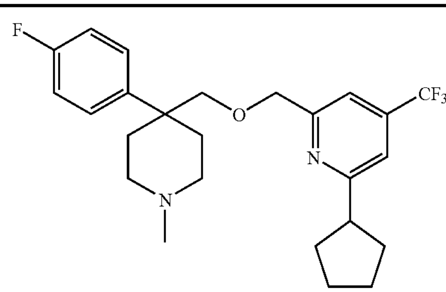 | 451.12 | 1.970 | δ 7.48 (m, 2H), 7.37 (m, 1H), 7.14 (m, 3H), 4.54 (m, 2H), 3.45 (m, 4H), 2.85 (m, 2H), 2.75 (s, 3H), 2.67 (m, 2H), 2.17 (m, 2H), 2.03 (m, 3H), 1.71 (m, 6H). |

| Example | Structure | MS (MH)+ | HPLC | 1H NMR |
|---|---|---|---|---|
| 101 | 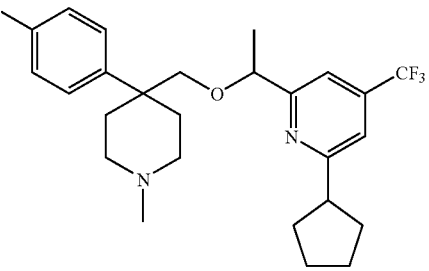 | 523.67 | 2.58 | δ 7.44 (m, 2H), 7.30 (s, 1H), 7.13 (m, 2H), 6.94 (s, 1H), 4.33 (q, 1H), 3.40 (m, 3H), 3.25 (m, 3H), 2.55-2.88 (m, 2H), 2.74 (s, 3H), 2.12 (m, 3H), 1.30 (d, 3H), 0.99 (m, 4H). |

We claim:

1. A compound of Formula I

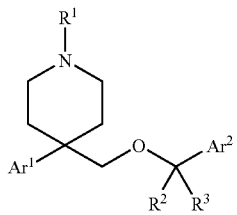

where:

R¹ is hydrogen or alkyl;

R² is hydrogen or alkyl;

R³ is hydrogen or alkyl;

R⁵ is hydrogen or alkyl;

Ar¹ is phenyl or pyridinyl and is substituted with 0-3 substituents selected from the group consisting of halo, alkyl, haloalkyl, and cyano;

Ar² is pyridinyl or pyrimidinyl and is substituted with 1 cycloalkyl substituent and 1 haloalkyl substituent; and or a pharmaceutically acceptable salt thereof.

2. A compound of claim 1 where:

R¹ is hydrogen or alkyl;

R² is hydrogen or alkyl;

R³ is hydrogen or alkyl;

Ar¹ is phenyl substituted with 0-2 substituents selected from the group consisting of halo, alkyl, haloalkyl, and cyano;

Ar² is 2-cyclopropyl-4-trifluoromethyl-pyridin-6-yl or a pharmaceutically acceptable salt thereof.

3. A compound of claim 2 where R¹ is hydrogen.

4. A compound of claim 2 where R¹ is methyl.

5. A compound of claim 2 where R² and R³ are hydrogen.

6. A compound of claim 2 where R² is methyl and R³ is hydrogen.

7. A compound of claim 2 where Ar¹ is phenyl.

8. A compound of claim 1 selected from the group consisting of

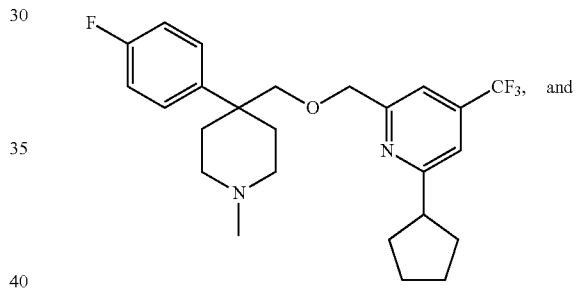 and

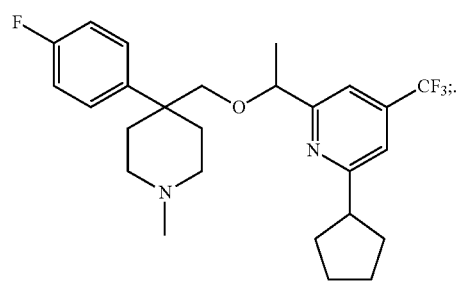

or a pharmaceutically acceptable salt thereof.

9. A compound of claim 2 selected from
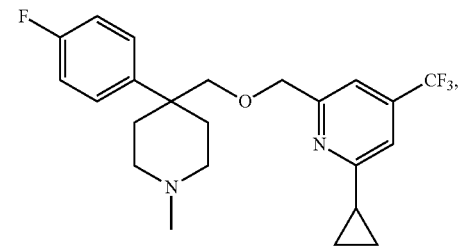
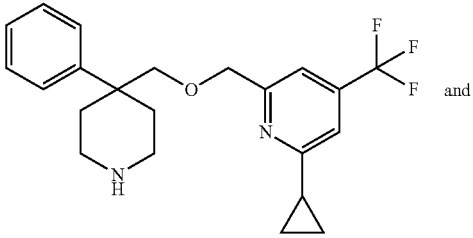
and
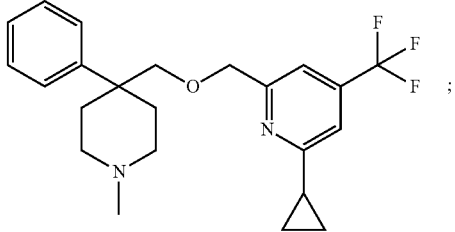
or a pharmaceutically acceptable salt thereof.
10. A composition comprising a pharmaceutically acceptable amount of a compound of claim 1 and a pharmaceutically acceptable carrier.
* * * * *

UNITED STATES PATENT AND TRADEMARK OFFICE
CERTIFICATE OF CORRECTION

| | | |
|---|---|---|
| PATENT NO. | : 8,071,778 B2 | Page 1 of 2 |
| APPLICATION NO. | : 12/019994 | |
| DATED | : December 6, 2011 | |
| INVENTOR(S) | : Michael E. Parker et al. | |

It is certified that error appears in the above-identified patent and that said Letters Patent is hereby corrected as shown below:

On the Title Page:

Item (56), References Cited, under OTHER PUBLICATIONS:

Column 2, Kramer, M.S. et al. reference, change "Distant" to -- Distinct --.

The reference should read:

-- Kramer, M.S., et al., "Distinct Mechanism for Antidepressant Activity by Blockade of Central Substance P Receptors", *Science*, 281 (1998) 1640-1645. --.

Column 2, first Stevenson, G.I. et al. reference, change "Antagoinists" to -- Antagonists --.

The reference should read:

-- Stevenson, G.I., et al., "4,4-Disubstituted Piperidines: A New Class of $NK_1$ Antagonists", *J. Med. Chem.*, 38 (1995) 1264-1266. --.

Column 2, second Stevenson, G.I. et al. reference, change "Antagoinists" to -- Antagonists --.

The reference should read:

-- Stevenson, G.I., et al., "4,4-Disubstituted Piperidine High-Affinity $NK_1$ Antagonists: Structure-Activity Relationships and in Vivo Activity", *J. Med. Chem.*, 41 (1998) 4623-4635. --.

Claim 1:

Column 101, line 46, delete "$R^5$ is hydrogen or alkyl;".

Column 101, line 54, after "substituent;", delete "and".

Signed and Sealed this
Twenty-eighth Day of August, 2012

David J. Kappos
*Director of the United States Patent and Trademark Office*

CERTIFICATE OF CORRECTION (continued)
U.S. Pat. No. 8,071,778 B2

Claim 2:

Column 101, line 66, after "-yl", insert -- ; --.

Claim 8:

Column 102, line 28, below "ing of", insert

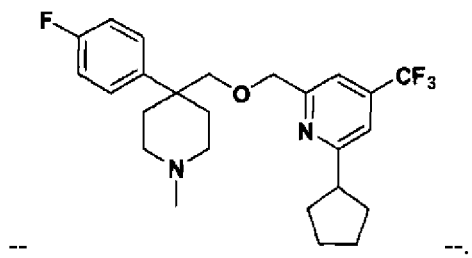

-- --.

Column 102, lines 54 to 63, after

"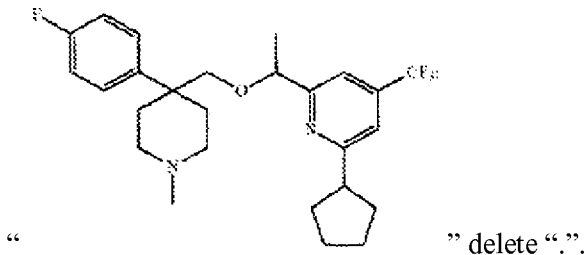" delete ".".